(12) United States Patent
Tateno et al.

(10) Patent No.: US 11,098,299 B2
(45) Date of Patent: Aug. 24, 2021

(54) MUTANT NITRILE HYDRATASE, NUCLEIC ACID CODING SAID MUTANT NITRILE HYDRATASE, EXPRESSION VECTOR AND TRANSFORMANT INCLUDING SAID NUCLEIC ACID, PRODUCTION METHOD FOR SAID MUTANT NITRILE HYDRATASE, AND PRODUCTION METHOD FOR AMIDE COMPOUND

(71) Applicant: Mitsui Chemicals, Inc., Tokyo (JP)

(72) Inventors: Toshihiro Tateno, Mobara (JP); Junko Tokuda, Chiba (JP); Keiichirou Kai, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 16/473,041

(22) PCT Filed: Dec. 27, 2017

(86) PCT No.: PCT/JP2017/047127
§ 371 (c)(1),
(2) Date: Jun. 24, 2019

(87) PCT Pub. No.: WO2018/124247
PCT Pub. Date: Jul. 5, 2018

(65) Prior Publication Data
US 2019/0367897 A1 Dec. 5, 2019

(30) Foreign Application Priority Data

Dec. 28, 2016 (JP) .............................. JP2016-256050

(51) Int. Cl.
*C12N 9/88* (2006.01)
*C12N 15/70* (2006.01)
*C12P 13/02* (2006.01)

(52) U.S. Cl.
CPC .............. *C12N 9/88* (2013.01); *C12N 15/70* (2013.01); *C12P 13/02* (2013.01); *C12Y 402/01084* (2013.01)

(58) Field of Classification Search
CPC ....................................................... C12N 9/88
See application file for complete search history.

(56) References Cited

U.S. PATENT DOCUMENTS

| 8,871,484 B2 | 10/2014 | Matsumoto et al. |
| 2003/0104586 A1 | 6/2003 | Abe et al. |
| 2007/0009985 A1 | 1/2007 | Yamaki et al. |
| 2011/0212506 A1 | 9/2011 | Matsumoto et al. |

FOREIGN PATENT DOCUMENTS

| EP | 0790310 A2 | 8/1997 |
| JP | H09275978 A | 10/1997 |
| JP | 2001270857 A | 10/2001 |
| JP | 2004194588 A | 7/2004 |
| JP | 2005160403 A | 6/2005 |
| JP | 2007143409 A | 6/2007 |
| JP | 2008253182 A | 10/2008 |
| KR | 20110084442 A | 7/2011 |
| WO | 2004056990 A1 | 7/2004 |
| WO | 2010055666 A1 | 5/2010 |

OTHER PUBLICATIONS

Airaksinen et al., "Modified base compositions at degenerate positions of a mutagenic oligonucleotide enhance randomness in site-saturation mutagenesis", Nucleic Acids Research, 1998, vol. 26, No. 2, pp. 576-581.*
Folz et al., "Substrate Specificity of Eukaryotic Signal Peptidase", JBC, 1988, vol. 263, No. 4, pp. 2070-2078.*
A. Miyanaga, et al., "Mutational and structural analysis of cobalt-containing nitrile hydratase on substrate and metal binding," Eur. J. Biochem. 271, 429-438 (2004).
International Search Report (with English translation) and Written Opinion issued in corresponding International Patent Application No. PCT/JP2017/047127, 10 pages (dated Mar. 27, 2018).
Amit Pratush et al., "Purification and characterization of nitrile hydratase of mutant 4D of Rhodococcus rhodochrous PA-34", 3 Biotech (2013) 3:165-171.
Korean Office Action dated Jun. 10, 2020, by the Korean Intellectual Property Office in corresponding Korean Patent Application No. 10-2019-7017583, with a partial English translation of the Office Action (11 pages).

* cited by examiner

*Primary Examiner* — Suzanne M Noakes
(74) *Attorney, Agent, or Firm* — Buchanan, Ingersoll & Rooney PC

(57) ABSTRACT

A mutant nitrile hydratase that is derived from *Pseudonocardia thermophila* and has an α subunit and a β subunit, wherein a specific amino acid residue has been substituted for the amino acid residue in at least one position selected from the group consisting of the 40th and 43rd residues from the N terminal of the α subunit, and the 205th, 206th, and 215th residues from the N terminal of the β subunit.

17 Claims, No Drawings

Specification includes a Sequence Listing.

SEQUENCE LISTING

```
<160> NUMBER OF SEQ ID NOS: 75

<210> SEQ ID NO 1
<211> LENGTH: 205
<212> TYPE: PRT
<213> ORGANISM: Pseudonocardia thermophila

<400> SEQUENCE: 1

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
                20                  25                  30

Ile Leu Thr Thr Ser Met Ile Asp Arg Met Ala Glu Ile Tyr Glu Asn
            35                  40                  45

Glu Val Gly Pro His Leu Gly Ala Lys Val Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
```

```
                    85                  90                  95
Glu Asn Thr Asp Glu Val His His Val Val Cys Thr Leu Cys Ser
                    100                 105                 110

Cys Tyr Pro Trp Pro Val Leu Gly Leu Pro Pro Asn Trp Phe Lys Glu
            115                 120                 125

Pro Gln Tyr Arg Ser Arg Val Val Arg Glu Pro Arg Gln Leu Leu Lys
    130                 135                 140

Glu Phe Gly Phe Glu Val Pro Pro Ser Lys Glu Ile Lys Val Trp
145                 150                 155                 160

Asp Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
            195                 200                 205

<210> SEQ ID NO 2
<211> LENGTH: 233
<212> TYPE: PRT
<213> ORGANISM: Pseudonocardia thermophila

<400> SEQUENCE: 2

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
                100                 105                 110

Pro Glu Leu Ile Glu Phe Val Asn Gln Ala Val Tyr Gly Gly Leu Pro
            115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
    195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230

<210> SEQ ID NO 3
<211> LENGTH: 618
```

```
<212> TYPE: DNA
<213> ORGANISM: Pseudonocardia thermophila

<400> SEQUENCE: 3
atgaccgaga acatcctgcg caagtcggac gaggagatcc agaaggagat cacggcgcgg      60
gtcaaggccc tggagtcgat gctcatcgaa cagggcatcc tcaccacgtc gatgatcgac     120
cggatggccg agatctacga gaacgaggtc ggcccgcacc tcggcgcgaa ggtcgtcgtg     180
aaggcctgga ccgacccgga gttcaagaag cgtctgctcg ccgacggcac cgaggcctgc     240
aaggagctcg gcatcggcgg cctgcagggc gaggacatga tgtgggtgga aacaccgac      300 gaggtccacc acgtcgtcgt gtgcacgctc tgctcctgct accgtggcc ggtgctgggg      360 ctgccgccga actggttcaa ggagccgcag taccgctccc gcgtggtgcg tgagccccgg     420
cagctgctca aggaggagtt cggcttcgag gtcccgccga gcaaggagat caaggtctgg     480
gactccagct ccgagatgcg cttcgtcgtc ctcccgcagc gccccgcggg caccgacggg     540
tggagcgagg aggagctcgc caccctcgtc accgcgagt cgatgatcgg cgtcgaaccg      600
gcgaaggcgg tcgcgtga                                                    618

<210> SEQ ID NO 4
<211> LENGTH: 702
<212> TYPE: DNA
<213> ORGANISM: Pseudonocardia thermophila

<400> SEQUENCE: 4
atgaacggcg tgtacgacgt cggcggcacc gatgggctgg gcccgatcaa ccggcccgcg      60
gacgaaccgg tcttccgcgc cgagtgggag aaggtcgcgt tcgcgatgtt cccggcgacg     120
ttccgggccg gcttcatggg cctggacgag ttccggttcg gcatcgagca gatgaacccg     180
gccgagtacc tcgagtcgcc gtactactgg cactggatcc gcacctacat ccaccacggc     240
gtccgcaccg gcaagatcga tctcgaggag ctggagcgcc gcacgcagta ctaccgggag     300
aaccccgacg ccccgctgcc cgagcacgag cagaagccgg agttgatcga gttcgtcaac     360
caggccgtct acggcgggct gcccgcaagc cgggaggtcg accgaccgcc caagttcaag     420
gagggcgacg tggtgcggtt ctccaccgcg agcccgaagg ccacgcccg gcgcgcgcgg     480 tacgtgcgcg gcaagaccgg gacggtggtc aagcaccacg gcgcgtacat ctacccggac     540
accgccggca acggcctggg cgagtgcccc gagcacctct acaccgtccg cttcacggcc     600
caggagctgt gggggccgga agggacccg aactccagcg tctactacga ctgctgggag     660
ccctacatcg agctcgtcga cacgaaggcg gccgcggcat ga                        702

<210> SEQ ID NO 5
<211> LENGTH: 24
<212> TYPE: DNA
<213> ORGANISM: Artificial
<220> FEATURE:
<223> OTHER INFORMATION: Primer

<400> SEQUENCE: 5
cagggcgagg agatgatgtg ggtg                                              24

<210> SEQ ID NO 6
<211> LENGTH: 21
<212> TYPE: DNA
<213> ORGANISM: Artificial
<220> FEATURE:
<223> OTHER INFORMATION: Primer
```

```
<400> SEQUENCE: 6
atcctcacct ggtcgatgat c                                              21

<210> SEQ ID NO 7
<211> LENGTH: 21
<212> TYPE: DNA
<213> ORGANISM: Artificial
<220> FEATURE:
<223> OTHER INFORMATION: Primer

<400> SEQUENCE: 7
gtcgatgatc aaccggatgg c                                              21

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
accggatggt cgagatctac                                                20

<210> SEQ ID NO 9
<211> LENGTH: 21
<212> TYPE: DNA
<213> ORGANISM: Artificial
<220> FEATURE:
<223> OTHER INFORMATION: Primer

<400> SEQUENCE: 9
gagctgtggg tgccggaagg g                                              21

<210> SEQ ID NO 10
<211> LENGTH: 21
<212> TYPE: DNA
<213> ORGANISM: Artificial
<220> FEATURE:
<223> OTHER INFORMATION: Primer

<400> SEQUENCE: 10
ctgtgggggc aggaagggga c                                              21

<210> SEQ ID NO 11
<211> LENGTH: 21
<212> TYPE: DNA
<213> ORGANISM: Artificial
<220> FEATURE:
<223> OTHER INFORMATION: primer

<400> SEQUENCE: 11
ctccagcgtc aactacgact g                                              21

<210> SEQ ID NO 12
<211> LENGTH: 17
<212> TYPE: DNA
<213> ORGANISM: Artificial
<220> FEATURE:
<223> OTHER INFORMATION: Primer

<400> SEQUENCE: 12
gttttcccag tcacgac                                                   17

<210> SEQ ID NO 13
<211> LENGTH: 17
```

```
<212> TYPE: DNA
<213> ORGANISM: Artificial
<220> FEATURE:
<223> OTHER INFORMATION: Primer

<400> SEQUENCE: 13
caggaaacag ctatgac                                                   17

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ggccagtgcc tagcttacat                                                20

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
gctgtgggtg caggaagggg                                                20

<210> SEQ ID NO 16
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 16
```

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Met Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Val Cys Thr Leu Cys Ser
            100                 105                 110

Cys Tyr Pro Trp Pro Val Leu Gly Leu Pro Pro Asn Trp Phe Lys Glu
        115                 120                 125

Pro Gln Tyr Arg Ser Arg Val Val Arg Glu Pro Arg Gln Leu Leu Lys
    130                 135                 140

Glu Glu Phe Asp Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Glu Leu Ala Thr Leu Val Thr Arg
            180                 185                 190

```
Glu Ser Met Ile Gly Val Glu Pro Ala Lys Ala Arg Ala
            195                 200                 205

<210> SEQ ID NO 17
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 17

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Met Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Glu Met Met Trp Val
                85                  90                  95

Glu Asn Thr Asp Glu Val His His Val Val Val Cys Thr Leu Cys Ser
            100                 105                 110

Cys Tyr Pro Trp Pro Val Leu Gly Leu Pro Pro Asn Trp Phe Lys Glu
        115                 120                 125

Pro Gln Tyr Arg Ser Arg Val Val Arg Glu Pro Arg Gln Leu Leu Lys
    130                 135                 140

Glu Glu Phe Asp Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Arg Ala
        195                 200                 205

<210> SEQ ID NO 18
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 18

Met Thr Glu Asn Ile Thr Arg Lys Ser Asp Glu Glu Ile Gln Lys Glu
1               5                   10                  15

Ile Thr Val Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95
```

Glu Asn Thr Asp Glu Val His His Val Val Cys Thr Leu Cys Ser
            100                 105                 110

Cys Tyr Pro Trp Pro Val Leu Gly Leu Pro Pro Asn Trp Tyr Lys Glu
            115                 120                 125

Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 19
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 19

Met Thr Glu Asn Ile Thr Arg Lys Ser Asp Glu Glu Ile Gln Lys Glu
1               5                   10                  15

Ile Thr Val Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Lys Ala Trp Thr
50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Ile Trp Val
                85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Tyr Lys Glu
            115                 120                 125

Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 20
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 20

Met Thr Glu Asn Ile Ala Arg Lys Ser Asp Glu Glu Ile Gln Lys Glu
1               5                   10                  15

Ile Thr Val Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Tyr Lys Glu
            115                 120                 125

Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 21
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 21

Met Thr Glu Asn Ile Leu Arg Lys Ser Asp Glu Glu Ile Gln Lys Glu
1               5                   10                  15

Ile Thr Val Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys His Leu Leu Ala Asp Gly Thr Glu Ala Cys
65                  70                  75                  80

Lys Glu Leu Gly Ile Gly Gly Leu Gln Gly Asp Met Met Trp Val
                85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Tyr Lys Glu
            115                 120                 125

Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp

```
            145                 150                 155                 160
Asp Ser Ser Glu Met Arg Phe Val Val Leu Pro Gln Arg Pro Ala
                165                 170                 175
Gly Thr Asp Gly Trp Ser Glu Glu Leu Ala Thr Leu Val Thr Arg
                180                 185                 190
Glu Ser Met Ile Gly Val Glu Pro Ala Lys Ala Val Ala
                195                 200                 205

<210> SEQ ID NO 22
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 22

Met Thr Glu Asn Ile Leu Arg Lys Ser Asp Glu Glu Leu Gln Lys Glu
1               5                   10                  15
Ile Thr Val Arg Val Lys Ala Leu Glu Ser Met Leu Ile Glu Gln Gly
                20                  25                  30
Ile Leu Thr Thr Ser Met Ile Asp Arg Met Ala Glu Ile Tyr Glu Asn
                35                  40                  45
Glu Val Gly Pro His Leu Gly Ala Lys Val Val Lys Ala Trp Thr
    50                  55                  60
Asp Pro Glu Phe Lys Lys His Leu Leu Ala Asp Gly Thr Glu Ala Cys
65                  70                  75                  80
Lys Glu Leu Gly Ile Gly Gly Leu Gln Gly Glu Asp Met Met Trp Val
                85                  90                  95
Glu Asn Thr Asp Glu Val His His Val Val Val Cys Thr Leu Cys Ser
                100                 105                 110
Cys Tyr Pro Trp Pro Val Leu Gly Leu Pro Pro Asn Trp Tyr Lys Glu
            115                 120                 125
Pro Gln Tyr Arg Ser Arg Val Val Arg Glu Pro Arg Gln Leu Leu Lys
            130                 135                 140
Glu Glu Phe Gly Phe Glu Val Pro Pro Ser Lys Glu Ile Lys Val Trp
145                 150                 155                 160
Asp Ser Ser Ser Glu Met Arg Phe Val Val Leu Pro Gln Arg Pro Ala
                165                 170                 175
Gly Thr Asp Gly Trp Ser Glu Glu Leu Ala Thr Leu Val Thr Arg
                180                 185                 190
Glu Ser Met Ile Gly Val Glu Pro Ala Lys Ala Val Ala
                195                 200                 205

<210> SEQ ID NO 23
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 23

Met Thr Glu Asn Ile Thr Arg Lys Ser Asp Glu Glu Ile Gln Lys Glu
1               5                   10                  15
Ile Thr Ala Arg Val Lys Ala Leu Glu Ser Met Leu Ile Glu Gln Gly
                20                  25                  30
Ile Leu Thr Met Ser Met Ile Asp Arg Met Ala Glu Ile Tyr Glu Asn
                35                  40                  45
```

-continued

```
Glu Val Gly Pro His Leu Gly Ala Lys Val Val Lys Ala Trp Thr
 50                  55                  60

Asp Pro Glu Phe Lys Lys Arg Leu Leu Ala Asp Gly Thr Glu Ala Cys
 65                  70                  75                  80

Lys Glu Leu Gly Ile Gly Gly Leu Gln Gly Glu Asp Met Met Trp Val
                 85                  90                  95

Glu Asn Thr Asp Glu Val His His Val Val Cys Thr Leu Cys Ser
                100                 105                 110

Cys Tyr Pro Trp Pro Val Leu Gly Leu Pro Pro Asn Trp Tyr Lys Glu
                115                 120                 125

Pro Gln Tyr Arg Ser Arg Val Val Arg Glu Pro Arg Gln Leu Leu Lys
    130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                    165                 170                 175

Gly Thr Asp Gly Trp Ser Glu Glu Leu Ala Thr Leu Val Thr Arg
                180                 185                 190

Glu Ser Met Ile Gly Val Glu Pro Ala Lys Ala Val Ala
            195                 200                 205

<210> SEQ ID NO 24
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 24

Met Thr Glu Asn Ile Thr Arg Lys Ser Asp Glu Glu Ile Gln Lys Glu
 1                   5                  10                  15

Ile Thr Ala Arg Val Lys Ala Leu Glu Ser Ile Leu Ile Glu Gln Gly
                 20                  25                  30

Ile Leu Thr Met Ser Met Ile Asp Arg Met Ala Glu Ile Tyr Glu Asn
             35                  40                  45

Glu Val Gly Pro His Leu Gly Ala Lys Val Val Lys Ala Trp Thr
 50                  55                  60

Asp Pro Glu Phe Lys Lys Arg Leu Leu Ala Asp Gly Thr Glu Ala Cys
 65                  70                  75                  80

Lys Glu Leu Gly Ile Gly Gly Leu Gln Gly Glu Asp Met Met Trp Val
                 85                  90                  95

Glu Asn Thr Asp Glu Val His His Val Val Cys Thr Leu Cys Ser
                100                 105                 110

Cys Tyr Pro Trp Pro Val Leu Gly Leu Pro Pro Asn Trp Tyr Lys Glu
                115                 120                 125

Pro Gln Tyr Arg Ser Arg Val Val Arg Glu Pro Arg Gln Leu Leu Lys
    130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                    165                 170                 175

Gly Thr Asp Gly Trp Ser Glu Glu Leu Ala Thr Leu Val Thr Arg
                180                 185                 190

Glu Ser Met Ile Gly Val Glu Pro Ala Lys Ala Val Ala
            195                 200                 205
```

```
<210> SEQ ID NO 25
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 25

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
                20                  25                  30

Ile Leu Thr Thr Ser Met Ile Asp Arg Met Ala Glu Ile Tyr Glu Asn
                35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Met Met Trp Val
                85                  90                  95

Glu Asn Thr Asp Glu Val His His Val Val Cys Thr Leu Cys Ser
                100                 105                 110

Cys Tyr Pro Trp Pro Val Leu Gly Leu Pro Pro Asn Trp Phe Lys Glu
                115                 120                 125

Pro Gln Tyr Arg Ser Arg Val Val Arg Glu Pro Arg Gln Leu Leu Lys
                130                 135                 140

Glu Glu Phe Asp Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
                180                 185                 190

Glu Ser Met Ile Gly Val Glu Pro Ala Lys Ala Arg Ala
                195                 200                 205

<210> SEQ ID NO 26
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 26

Met Thr Glu Asn Ile Leu Arg Lys Ser Asp Glu Glu Leu Gln Lys Glu
1               5                   10                  15

Ile Thr Val Arg Val Lys Ala Leu Glu Ser Ile Leu Ile Glu Gln Gly
                20                  25                  30

Ile Leu Thr Thr Ser Met Ile Asp Arg Met Ala Glu Ile Tyr Glu Asn
                35                  40                  45

Glu Val Gly Pro His Leu Gly Ala Lys Val Val Lys Ala Trp Thr
    50                  55                  60

Asp Pro Glu Phe Lys Lys His Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Cys Thr Leu Cys Ser
                100                 105                 110
```

Cys Tyr Pro Trp Pro Val Leu Gly Leu Pro Pro Asn Trp Tyr Lys Glu
            115                 120                 125

Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp
145                 150                 155                 160

Asp Ser Ser Glu Met Arg Phe Val Val Leu Pro Gln Arg Pro Ala
            165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 27
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 27

Met Thr Glu Asn Ile Leu Arg Lys Ser Asp Glu Glu Leu Gln Lys Glu
1               5                   10                  15

Ile Thr Ala Arg Val Lys Ala Leu Glu Ser Ile Leu Ile Glu Gln Gly
            20                  25                  30

Ile Leu Thr Thr Ser Met Ile Asp Arg Met Ala Glu Ile Tyr Glu Asn
            35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
            85                  90                  95

Glu Asn Thr Asp Glu Val His His Val Val Val Cys Thr Leu Cys Ser
            100                 105                 110

Cys Tyr Pro Trp Pro Val Leu Gly Leu Pro Pro Asn Trp Phe Lys Glu
            115                 120                 125

Pro Gln Tyr Arg Ser Arg Val Val Arg Glu Pro Arg Gln Leu Leu Lys
        130                 135                 140

Glu Glu Phe Gly Phe Glu Val Pro Pro Ser Lys Glu Ile Lys Val Trp
145                 150                 155                 160

Asp Ser Ser Glu Met Arg Phe Val Val Leu Pro Gln Arg Pro Ala
            165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
        195                 200                 205

<210> SEQ ID NO 28
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 28

Met Thr Glu Asn Ile Leu Arg Lys Ser Asp Glu Glu Leu Gln Lys Glu

```
            1               5                  10                 15
Ile Thr Ala Arg Val Lys Ala Leu Glu Ser Met Leu Ile Glu Gln Gly
            20                 25                 30

Ile Leu Thr Thr Ser Met Ile Asp Arg Met Ala Glu Ile Tyr Glu Asn
            35                 40                 45

Glu Val Gly Pro His Leu Gly Ala Lys Val Val Lys Ala Trp Thr
        50                 55                 60

Asp Pro Glu Phe Lys Lys Arg Leu Leu Ala Asp Gly Thr Glu Ala Cys
65                  70                 75                  80

Lys Glu Leu Gly Ile Gly Gly Leu Gln Gly Glu Asp Met Met Trp Val
                85                 90                 95

Glu Asn Thr Asp Glu Val His His Val Val Cys Thr Leu Cys Ser
            100                105                110

Cys Tyr Pro Trp Pro Val Leu Gly Leu Pro Pro Asn Trp Phe Lys Glu
            115                120                125

Pro Gln Tyr Arg Ser Arg Val Val Arg Glu Pro Arg Gln Leu Leu Lys
            130                135                140

Glu Glu Phe Gly Phe Glu Val Pro Pro Ser Lys Glu Ile Lys Val Trp
145                 150                155                160

Asp Ser Ser Ser Glu Met Arg Phe Val Val Leu Pro Gln Arg Pro Ala
                165                170                175

Gly Thr Asp Gly Trp Ser Glu Glu Leu Ala Thr Leu Val Thr Arg
            180                185                190

Glu Ser Met Ile Gly Val Glu Pro Ala Lys Ala Val Ala
            195                200                205

<210> SEQ ID NO 29
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 29

Met Thr Glu Asn Ile Leu Arg Lys Ser Asp Glu Glu Ile Gln Lys Glu
1               5                  10                 15

Ile Thr Ala Arg Val Lys Ala Leu Glu Ser Met Leu Ile Glu Gln Gly
            20                 25                 30

Ile Leu Thr Thr Ser Met Ile Asp Arg Met Ala Glu Ile Tyr Glu Asn
            35                 40                 45

Glu Val Gly Pro His Leu Gly Ala Lys Val Val Lys Ala Trp Thr
        50                 55                 60

Asp Pro Glu Phe Lys Lys Arg Leu Leu Ala Asp Gly Thr Glu Ala Cys
65                  70                 75                  80

Lys Glu Leu Gly Ile Gly Gly Leu Gln Gly Glu Asp Met Met Trp Val
                85                 90                 95

Glu Asn Thr Asp Glu Val His His Val Val Cys Thr Leu Cys Ser
            100                105                110

Cys Tyr Pro Trp Pro Val Leu Gly Leu Pro Pro Asn Trp Phe Lys Glu
            115                120                125

Pro Gln Tyr Arg Ser Arg Val Val Arg Glu Pro Arg Gln Leu Leu Lys
            130                135                140

Glu Glu Phe Gly Phe Glu Val Pro Pro Ser Lys Glu Ile Lys Val Trp
145                 150                155                160

Asp Ser Ser Ser Glu Met Arg Phe Val Val Leu Pro Gln Arg Pro Ala
```

165                 170                 175

Gly Thr Asp Gly Trp Ser Glu Glu Leu Ala Thr Leu Val Thr Arg
            180                 185                 190

Glu Ser Met Ile Cys Val Glu Pro Ala Lys Ala Val Ala
            195                 200                 205

<210> SEQ ID NO 30
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 30

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Asn
        35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Met Met Trp Val
                85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Phe Lys Glu
        115                 120                 125

Pro Gln Tyr Arg Ser Arg Val Val Arg Glu Pro Arg Gln Leu Leu Lys
    130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
            195                 200                 205

<210> SEQ ID NO 31
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 31

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
            20                  25                  30

Ile Leu Thr Thr Ser Met Ile Asp Arg Met Ala Glu Ile Tyr Glu Glu
        35                  40                  45

Glu Val Gly Pro His Leu Gly Ala Lys Val Val Lys Ala Trp Thr
    50                  55                  60

```
Asp Pro Glu Phe Lys Lys Arg Leu Leu Ala Asp Gly Thr Glu Ala Cys
 65                  70                  75                  80

Lys Glu Leu Gly Ile Gly Gly Leu Gln Gly Glu Asp Met Met Trp Val
                 85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Phe Lys Glu
            115                 120                 125

Pro Gln Tyr Arg Ser Arg Val Val Arg Glu Pro Arg Gln Leu Leu Lys
            130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Cys Val Glu Pro Ala Lys Ala Val Ala
            195                 200                 205
```

<210> SEQ ID NO 32
<211> LENGTH: 205
<212> TYPE: PRT
<213> ORGANISM: Artificial
<220> FEATURE:
<223> OTHER INFORMATION: Modified nitrile hydratase alpha-subunit

<400> SEQUENCE: 32

```
Met Thr Glu Asn Ile Leu Arg Lys Ser Asp Glu Glu Ile Gln Lys Glu
  1               5                  10                  15

Ile Thr Ala Arg Val Lys Ala Leu Glu Ser Met Leu Ile Glu Gln Gly
             20                  25                  30

Ile Leu Thr Ser Ser Met Ile Asp Arg Met Ala Glu Ile Tyr Glu Asn
             35                  40                  45

Glu Val Gly Pro His Leu Gly Ala Lys Val Val Lys Ala Trp Thr
 50                  55                  60

Asp Pro Glu Phe Lys Lys Arg Leu Leu Ala Asp Gly Thr Glu Ala Cys
 65                  70                  75                  80

Lys Glu Leu Gly Ile Gly Gly Leu Gln Gly Glu Glu Met Met Trp Val
                 85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Phe Lys Glu
            115                 120                 125

Pro Gln Tyr Arg Ser Arg Val Val Arg Glu Pro Arg Gln Leu Leu Lys
            130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
            195                 200                 205
```

<210> SEQ ID NO 33
<211> LENGTH: 233

```
<212> TYPE: PRT
<213> ORGANISM: Artificial
<220> FEATURE:
<223> OTHER INFORMATION: Modified nitrile hydratase beta-subunit

<400> SEQUENCE: 33

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Ile Arg Ala Gly Phe Met Gly Leu
        35                  40                  45

Asp Glu Val Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Asp His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala Ala
225                 230

<210> SEQ ID NO 34
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 34

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Lys Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95
```

```
Tyr Tyr Arg Glu Asn Pro Asp Ala Pro Leu Pro Arg His Glu Gln Lys
            100                 105                 110

Pro Glu Leu Ile Glu Phe Val Asn Gln Ala Val Tyr Gly Gly Leu Pro
            115                 120                 125

Ala Ser Arg Glu Val Asp Arg Pro Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
            195                 200                 205

Asp Pro Asn Tyr Ser Val Tyr Tyr Asp Cys Trp Glu Pro Tyr Ile Glu
            210                 215                 220

Leu Val Asp Thr Lys Ala Ala Ala
225                 230

<210> SEQ ID NO 35
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 35

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Ser Pro
            115                 120                 125

Ala Ser Arg Glu Val Asp Arg Pro Pro Lys Phe Lys Glu Gly Asp Val
130                 135                 140

Val Arg Phe Ser Thr Ala Ser Pro Lys Gly His Ala Arg Arg Ala Trp
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Arg Gly Glu Cys Pro Glu His
            180                 185                 190

Leu Tyr Thr Val Arg Phe Thr Ala Gln Glu Leu Trp Gly Pro Glu Gly
            195                 200                 205

Asp Pro Asn Ser Ser Val Tyr Tyr Asp Cys Trp Glu Pro Tyr Ile Glu
            210                 215                 220
```

Leu Val Asp Thr Lys Ala Ala Ala Ala
225                 230

<210> SEQ ID NO 36
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 36

Met Asn Gly Met Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Ser Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Trp
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Arg Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala Ala
225                 230

<210> SEQ ID NO 37
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 37

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Leu Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Asp His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Glu Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230

<210> SEQ ID NO 38
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 38

Met Asn Gly Val Tyr Asp Val Ala Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Leu Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Asp His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His

```
                180                 185                 190
Leu Tyr Thr Val Arg Phe Thr Glu Gln Glu Leu Trp Gly Pro Glu Gly
            195                 200                 205

Asp Pro Asn Ser Ser Val Tyr Tyr Asp Cys Trp Glu Pro Tyr Ile Glu
        210                 215                 220

Leu Val Asp Thr Lys Ala Ala Ala
225                 230

<210> SEQ ID NO 39
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 39

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Val Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Asp His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Glu Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230

<210> SEQ ID NO 40
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 40

Met Asn Gly Val Tyr Asp Val Gly Gly Thr Asp Gly Leu Gly Pro Ile
1               5                   10                  15
```

Asn Arg Pro Ala Asp Glu Pro Val Phe Arg Ala Glu Trp Glu Lys Val
            20                  25                  30

Ala Phe Ala Met Val Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
 50                  55                  60

Glu Ser Pro Tyr Tyr Trp His Trp Ile Arg Thr Tyr Ile His Asn Gly
 65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Asp His Glu Gln Lys
                100                 105                 110

Pro Glu Leu Ile Glu Phe Val Asn Gln Ala Val Tyr Gly Gly Leu Pro
                115                 120                 125

Ala Ser Arg Glu Val Asp Arg Pro Pro Lys Phe Lys Glu Gly Asp Val
            130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Glu Gln Glu Leu Trp Gly Pro Glu Gly
            195                 200                 205

Asp Pro Asn Ser Ser Val Tyr Tyr Asp Cys Trp Glu Pro Tyr Ile Glu
 210                 215                 220

Leu Val Asp Thr Lys Ala Ala Ala
225                 230

<210> SEQ ID NO 41
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 41

Met Asn Gly Val Tyr Asp Val Gly Gly Thr Asp Gly Leu Gly Pro Ile
 1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Val
            35                  40                  45

Asp Glu Phe Arg Phe Gly Ile Glu Gln Met Asn Pro Ala Glu Tyr Leu
 50                  55                  60

Glu Ser Pro Tyr Tyr Trp His Trp Ile Arg Thr Tyr Ile His Gly
 65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Arg His Glu Gln Lys
                100                 105                 110

Pro Glu Leu Ile Glu Phe Val Asn Gln Ala Val Tyr Gly Gly Leu Pro
                115                 120                 125

Ala Ser Arg Glu Val Asp Arg Pro Pro Lys Phe Lys Glu Gly Asp Val
            130                 135                 140

```
Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Tyr Ser Val Tyr Tyr Asp Cys Trp Glu Pro Tyr Ile Glu
    210                 215                 220

Leu Val Asp Thr Lys Ala Ala Ala
225                 230

<210> SEQ ID NO 42
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 42

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Val
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Arg
                85                  90                  95

Tyr Tyr Arg Glu Asn Pro Asp Ala Pro Leu Pro Arg His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Tyr Ser Val Tyr Tyr Asp Cys Trp Glu Pro Tyr Ile Glu
    210                 215                 220

Leu Val Asp Thr Lys Ala Ala Ala
225                 230

<210> SEQ ID NO 43
<211> LENGTH: 233
<212> TYPE: PRT
<213> ORGANISM: Artificial
<220> FEATURE:
```

<223> OTHER INFORMATION: Modified nitrile hydratase beta-subunit

<400> SEQUENCE: 43

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Val Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Met Asp His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Glu Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230
```

<210> SEQ ID NO 44
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 44

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Leu Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Arg
                85                  90                  95

Tyr Tyr Arg Glu Asn Pro Asp Ala Pro Leu Pro Asp His Glu Gln Lys
            100                 105                 110
```

```
Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
                180                 185                 190

Leu Tyr Thr Val Arg Phe Thr Glu Gln Glu Leu Trp Gly Pro Glu Gly
        195                 200                 205

Asp Pro Asn Ser Ser Val Tyr Tyr Asp Cys Trp Glu Pro Tyr Ile Glu
        210                 215                 220

Leu Val Asp Thr Lys Ala Ala Ala Ala
225                 230

<210> SEQ ID NO 45
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 45

Met Asn Gly Val Tyr Asp Val Gly Gly Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Val Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
                180                 185                 190

Leu Tyr Thr Val Arg Phe Thr Glu Gln Glu Leu Trp Gly Pro Glu Gly
        195                 200                 205

Asp Pro Asn Ser Ser Val Tyr Tyr Asp Cys Trp Glu Pro Tyr Ile Glu
        210                 215                 220

Leu Val Asp Thr Lys Ala Ala Ala Ala
225                 230
```

<210> SEQ ID NO 46
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 46

Met Asn Gly Val Tyr Asp Val Gly Gly Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Met Glu His Glu Gln Lys
            100                 105                 110

Pro Glu Leu Ile Glu Val Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Glu Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230

<210> SEQ ID NO 47
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 47

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly

```
                65                  70                  75                  80
Val Arg Thr Gly Lys Ile Asp Leu Glu Glu Leu Glu Arg Arg Thr Gln
                    85                  90                  95

Tyr Tyr Arg Glu Asn Pro Asp Ala Pro Leu Pro Asp His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Glu Gln Glu Leu Trp Gly Pro Glu Gly
        195                 200                 205

Asp Pro Asn Ser Ser Val Tyr Tyr Asp Cys Trp Glu Pro Tyr Ile Glu
        210                 215                 220

Leu Ile Asp Thr Lys Ala Ala Ala
225                 230

<210> SEQ ID NO 48
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 48

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Val
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His Asn Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Arg His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
```

```
                195                 200                 205
Asp Pro Asn Tyr Ser Val Tyr Tyr Asp Cys Trp Glu Pro Tyr Ile Glu
    210                 215                 220
Leu Val Asp Thr Lys Glu Ala Ala Ala
225                 230

<210> SEQ ID NO 49
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 49

Met Asn Gly Val Tyr Asp Val Gly Gly Asp Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Val Val Asn Gln Ala Val Tyr Gly Gly Leu Pro
        115                 120                 125

Ala Ser Arg Glu Val Asp Arg Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Glu Gln Glu Leu Trp Gly Leu Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Glu Ala Ala Ala
225                 230

<210> SEQ ID NO 50
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 50

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30
```

```
Ala Phe Ala Met Phe Pro Ala Thr Ile Arg Ala Gly Phe Met Gly Leu
            35                  40                  45

Asp Glu Val Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Asp His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
        130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Leu Glu Gly
        195                 200                 205

Asp Pro Asn Ser Ser Val Tyr Tyr Asp Cys Trp Glu Pro Tyr Ile Glu
        210                 215                 220

Leu Val Asp Thr Lys Glu Ala Ala Ala
225                 230

<210> SEQ ID NO 51
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 51

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Asn Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
        130                 135                 140

Val Arg Phe Ser Thr Ala Ser Pro Lys Gly His Ala Arg Arg Ala Arg
145                 150                 155                 160
```

```
Tyr Val Arg Gly Lys Thr Gly Thr Val Val Lys His His Gly Ala Tyr
            165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
            195                 200                 205

Asp Pro Asn Ser Ser Val Tyr Tyr Asp Cys Trp Glu Pro Tyr Ile Glu
            210                 215                 220

Leu Val Asp Thr Lys Ala Ala Ala
225                 230

<210> SEQ ID NO 52
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 52

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Lys Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Arg His Asn Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
            165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
            195                 200                 205

Asp Pro Asn Tyr Ser Val Tyr Tyr Asp Cys Trp Glu Pro Tyr Ile Glu
            210                 215                 220

Leu Val Asp Thr Lys Ala Ala Ala
225                 230

<210> SEQ ID NO 53
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 53
```

Met Asn Gly Val Tyr Asp Val Gly Gly Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Val Val Asn Gln Ala Val Tyr Gly Gly Leu Pro
            115                 120                 125

Ala Ser Arg Glu Val Asp Arg Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Glu Gln Glu Leu Trp Gly Leu Glu Gly
            195                 200                 205

Asp Pro Asn Ser Ser Val Tyr Tyr Asp Cys Trp Glu Pro Tyr Ile Glu
210                 215                 220

Leu Ile Asp Thr Lys Ala Ala Ala
225                 230

<210> SEQ ID NO 54
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 54

Met Asn Gly Met Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
            115                 120                 125

```
Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Leu Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230
```

<210> SEQ ID NO 55
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 55

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Ile Arg Ala Gly Phe Met Gly Leu
        35                  40                  45

Asp Glu Val Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Met Asp His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Glu Ala Ala Ala
225                 230
```

<210> SEQ ID NO 56

<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 56

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Val
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His Asn Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Arg His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Tyr Ser Val Tyr Tyr Asp Cys Trp Glu Pro Tyr Ile Glu
    210                 215                 220

Leu Val Asp Thr Lys Glu Val Ala Ala
225                 230
```

<210> SEQ ID NO 57
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 57

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Lys Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His Asn Gly
65                  70                  75                  80

Val Arg Thr Gly Lys Ile Asp Leu Glu Glu Leu Glu Arg Arg Thr Gln
```

Tyr Tyr Arg Glu Asn Pro Asp Ala Pro Leu Pro Arg His Glu Gln Lys
                85                  90                  95
            100                 105                 110

Pro Glu Leu Ile Glu Phe Val Asn Gln Ala Val Tyr Gly Gly Leu Pro
            115                 120                 125

Ala Ser Arg Glu Val Asp Arg Pro Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
                180                 185                 190

Leu Tyr Thr Val Arg Phe Thr Ala Gln Glu Leu Trp Gly Pro Glu Gly
                195                 200                 205

Asp Pro Asn Tyr Ser Val Tyr Tyr Asp Cys Trp Glu Pro Tyr Ile Glu
                210                 215                 220

Leu Val Asp Thr Lys Glu Val Ala Ala
225                 230

<210> SEQ ID NO 58
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 58

Met Asn Gly Val Tyr Asp Val Gly Gly Thr Asp Gly Leu Gly Pro Ile
1               5                   10                  15

Asn Arg Pro Ala Asp Glu Pro Ile Phe Arg Ala Glu Trp Glu Lys Val
                20                  25                  30

Ala Phe Ala Met Phe Pro Ala Thr Ile Arg Ala Gly Phe Met Gly Leu
            35                  40                  45

Asp Glu Val Arg Phe Gly Ile Glu Gln Met Asn Pro Ala Glu Tyr Leu
50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Asp His Glu Gln Lys
            100                 105                 110

Pro Glu Leu Ile Glu Phe Val Asn Gln Ala Val Tyr Gly Gly Leu Pro
            115                 120                 125

Ala Ser Arg Glu Val Asp Arg Pro Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
                180                 185                 190

Leu Tyr Thr Val Arg Phe Thr Ala Gln Glu Leu Trp Gly Pro Glu Gly
                195                 200                 205

Asp Pro Asn Ser Ser Val Tyr Tyr Asp Cys Trp Glu Pro Tyr Ile Glu

Leu Ile Asp Thr Lys Ala Ala Ala
225             230

<210> SEQ ID NO 59
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 59

Met Asn Gly Val Tyr Asp Val Gly Gly Thr Asp Gly Leu Gly Pro Ile
1               5                   10                  15

Asn Arg Pro Ala Asp Glu Pro Ile Phe Arg Ala Glu Trp Glu Lys Val
                20                  25                  30

Ala Phe Ala Met Phe Pro Ala Thr Ile Arg Ala Gly Phe Met Gly Leu
            35                  40                  45

Asp Glu Val Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Met Asp His Glu Gln Lys
                100                 105                 110

Pro Glu Leu Ile Glu Phe Val Asn Gln Ala Val Tyr Gly Gly Leu Pro
            115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Glu Ala Ala Ala
225                 230

<210> SEQ ID NO 60
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 60

Met Asn Gly Val Tyr Asp Val Gly Gly Thr Asp Gly Leu Gly Pro Ile
1               5                   10                  15

Asn Arg Pro Ala Asp Glu Pro Ile Phe Arg Ala Glu Trp Glu Lys Val
                20                  25                  30

Ala Phe Ala Met Phe Pro Ala Thr Phe Arg Ala Gly Phe Met Gly Leu
            35                  40                  45

```
Asp Glu Phe Arg Phe Gly Ile Glu Gln Met Asn Pro Ala Glu Tyr Leu
 50                  55                  60

Glu Ser Pro Tyr Tyr Trp His Trp Ile Arg Thr Tyr Ile His His Gly
 65                  70                  75                  80

Val Arg Thr Gly Lys Ile Asp Leu Glu Glu Leu Glu Arg Arg Thr Gln
                 85                  90                  95

Tyr Tyr Arg Glu Asn Pro Asp Ala Pro Leu Met Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
130                 135                 140

Val Gly Phe Ser Thr Ala Ser Pro Lys Gly His Ala Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
210                 215                 220

Leu Val Asp Thr Lys Glu Ala Ala Ala
225                 230

<210> SEQ ID NO 61
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 61

Met Asn Gly Val Tyr Asp Val Gly Gly Thr Asp Gly Leu Gly Pro Ile
  1               5                  10                  15

Asn Arg Pro Ala Asp Glu Pro Ile Phe Arg Ala Glu Trp Glu Lys Val
                 20                  25                  30

Ala Phe Ala Met Phe Pro Ala Thr Phe Arg Ala Gly Phe Met Gly Val
             35                  40                  45

Asp Glu Phe Arg Phe Gly Ile Glu Gln Met Asn Pro Ala Glu Tyr Leu
 50                  55                  60

Glu Ser Pro Tyr Tyr Trp His Trp Ile Arg Thr Tyr Ile His Asn Gly
 65                  70                  75                  80

Val Arg Thr Gly Lys Ile Asp Leu Glu Glu Leu Glu Arg Arg Thr Gln
                 85                  90                  95

Tyr Tyr Arg Glu Asn Pro Asp Ala Pro Leu Pro Arg His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
130                 135                 140

Val Arg Phe Ser Thr Ala Ser Pro Lys Gly His Ala Arg Ala Arg
145                 150                 155                 160

Tyr Val Arg Gly Lys Thr Gly Thr Val Val Lys His His Gly Ala Tyr
                165                 170                 175
```

```
Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Tyr Ser Val Tyr Tyr Asp Cys Trp Glu Pro Tyr Ile Glu
        210                 215                 220

Leu Val Asp Thr Lys Glu Val Ala Ala
225                 230

<210> SEQ ID NO 62
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 62

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Val Phe Ala Met Phe Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
        210                 215                 220

Leu Val Asp Thr Lys Ala Ala Ala Ala
225                 230

<210> SEQ ID NO 63
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 63

Met Asn Gly Val Tyr Asp Val Gly Gly Thr Asp Gly Leu Gly Pro Ile
1               5                   10                  15
```

Asn Arg Pro Ala Asp Glu Pro Val Phe Arg Ala Glu Trp Glu Lys Val
            20                  25                  30

Ala Phe Ala Met Phe Pro Ala Ile Phe Arg Ala Gly Phe Met Gly Leu
        35                  40                  45

Asp Glu Phe Arg Phe Gly Ile Glu Gln Met Asn Pro Val Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
                100                 105                 110

Pro Glu Leu Ile Glu Phe Val Asn Gln Ala Val Tyr Gly Gly Leu Pro
            115                 120                 125

Ala Ser Arg Glu Val Asp Arg Pro Lys Phe Lys Glu Gly Asp Val
130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Ala Ala Ala
225                 230

<210> SEQ ID NO 64
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 64

Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Ile Arg Ala Gly Phe Met Gly Leu
        35                  40                  45

Asp Glu Val Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Asp His Glu Gln Lys
                100                 105                 110

Pro Glu Leu Ile Glu Phe Val Asn Gln Ala Val Tyr Gly Gly Leu Pro
            115                 120                 125

Ala Ser Arg Glu Val Asp Arg Pro Lys Phe Lys Glu Gly Asp Val
130                 135                 140

```
Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Ile Asp Thr Lys Ala Ala Ala Ala
225                 230
```

<210> SEQ ID NO 65
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 65

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Leu Glu Tyr Leu
        50                  55                  60

Glu Ser Pro Tyr Tyr Trp His Trp Ile Arg Thr Tyr Ile His His Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Ile
                100                 105                 110

Pro Glu Leu Ile Glu Phe Val Asn Gln Ala Val Tyr Gly Gly Leu Pro
            115                 120                 125

Ala Ser Arg Glu Val Asp Arg Pro Pro Lys Phe Lys Glu Gly Asp Val
        130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Ile Asp Thr Lys Ala Ala Ala Ala
225                 230
```

<210> SEQ ID NO 66
<211> LENGTH: 233
<212> TYPE: PRT
<213> ORGANISM: Artificial

<220> FEATURE:
<223> OTHER INFORMATION: Modified nitrile hydratase beta-subunit

<400> SEQUENCE: 66

| Met | Asn | Gly | Met | Tyr | Asp | Val | Gly | Gly | Thr | Asp | Gly | Leu | Gly | Pro | Ile |
|---|---|---|---|---|---|---|---|---|---|---|---|---|---|---|---|
| 1 | | | | 5 | | | | | 10 | | | | | 15 | |

| Asn | Arg | Pro | Ala | Asp | Glu | Pro | Val | Phe | Arg | Ala | Glu | Trp | Glu | Lys | Val |
| | | | 20 | | | | | 25 | | | | | 30 | | |

| Ala | Phe | Ala | Met | Phe | Pro | Ala | Thr | Phe | Arg | Ala | Gly | Phe | Met | Gly | Leu |
| | | 35 | | | | | 40 | | | | | 45 | | | |

| Asp | Glu | Val | Arg | Phe | Gly | Ile | Glu | Gln | Met | Asn | Pro | Ala | Glu | Tyr | Leu |
| | 50 | | | | | 55 | | | | | 60 | | | | |

| Glu | Ser | Pro | Tyr | Tyr | Trp | His | Trp | Ile | Arg | Thr | Tyr | Ile | His | His | Gly |
| 65 | | | | 70 | | | | | 75 | | | | | 80 | |

| Val | Arg | Thr | Gly | Lys | Ile | Asp | Leu | Glu | Glu | Leu | Glu | Arg | Arg | Thr | Gln |
| | | | | 85 | | | | | 90 | | | | | 95 | |

| Tyr | Tyr | Arg | Glu | Asn | Pro | Asp | Ala | Pro | Leu | Pro | Asp | His | Glu | Gln | Lys |
| | | | 100 | | | | | 105 | | | | | 110 | | |

| Pro | Glu | Leu | Ile | Glu | Phe | Val | Asn | Gln | Ala | Val | Tyr | Gly | Gly | Leu | Pro |
| | | 115 | | | | | 120 | | | | | 125 | | | |

| Ala | Ser | Arg | Glu | Val | Asp | Arg | Pro | Pro | Lys | Phe | Lys | Glu | Gly | Asp | Val |
| | 130 | | | | | 135 | | | | | 140 | | | | |

| Val | Arg | Phe | Ser | Thr | Ala | Ser | Pro | Lys | Gly | His | Ala | Arg | Arg | Ala | Arg |
| 145 | | | | | 150 | | | | | 155 | | | | | 160 |

| Tyr | Val | Arg | Gly | Lys | Thr | Gly | Thr | Val | Val | Lys | His | His | Gly | Ala | Tyr |
| | | | | 165 | | | | | 170 | | | | | 175 | |

| Ile | Tyr | Pro | Asp | Thr | Ala | Gly | Asn | Gly | Leu | Gly | Glu | Cys | Pro | Glu | His |
| | | | 180 | | | | | 185 | | | | | 190 | | |

| Leu | Tyr | Thr | Val | Arg | Phe | Thr | Ala | Gln | Glu | Leu | Trp | Gly | Leu | Glu | Gly |
| | | 195 | | | | | 200 | | | | | 205 | | | |

| Asp | Pro | Asn | Ser | Ser | Val | Tyr | Tyr | Asp | Cys | Trp | Glu | Pro | Tyr | Ile | Glu |
| | 210 | | | | | 215 | | | | | 220 | | | | |

| Leu | Val | Asp | Thr | Lys | Ala | Ala | Ala | Ala |
|---|---|---|---|---|---|---|---|---|
| 225 | | | | | 230 | | | |

<210> SEQ ID NO 67
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 67

| Met | Asn | Gly | Val | Tyr | Asp | Val | Gly | Gly | Thr | Asp | Gly | Leu | Gly | Pro | Ile |
|---|---|---|---|---|---|---|---|---|---|---|---|---|---|---|---|
| 1 | | | | 5 | | | | | 10 | | | | | 15 | |

| Asn | Arg | Pro | Ala | Asp | Glu | Pro | Val | Phe | Arg | Ala | Glu | Trp | Glu | Lys | Val |
| | | | 20 | | | | | 25 | | | | | 30 | | |

| Met | Phe | Ala | Met | Phe | Pro | Ala | Thr | Phe | Arg | Ala | Gly | Phe | Met | Gly | Leu |
| | | 35 | | | | | 40 | | | | | 45 | | | |

| Asp | Glu | Phe | Arg | Phe | Gly | Ile | Glu | Gln | Met | Asn | Pro | Ala | Glu | Tyr | Leu |
| | 50 | | | | | 55 | | | | | 60 | | | | |

| Glu | Ser | Pro | Tyr | Tyr | Trp | His | Trp | Ile | Arg | Thr | Tyr | Ile | His | Asn | Gly |
| 65 | | | | 70 | | | | | 75 | | | | | 80 | |

| Val | Arg | Thr | Gly | Lys | Ile | Asp | Leu | Glu | Glu | Leu | Glu | Arg | Arg | Thr | Gln |
| | | | | 85 | | | | | 90 | | | | | 95 | |

| Tyr | Tyr | Arg | Glu | Asn | Pro | Asp | Ala | Pro | Leu | Pro | Glu | His | Glu | Gln | Lys |

```
            100                 105                 110
Pro Glu Leu Ile Glu Phe Val Asn Gln Ala Val Tyr Gly Gly Leu Pro
            115                 120                 125

Ala Ser Arg Glu Val Asp Arg Pro Pro Lys Phe Lys Glu Gly Asp Val
            130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Thr
                165                 170                 175

Ile Tyr Pro Asp Thr Ala Gly Asn Gly Leu Gly Glu Cys Pro Glu His
                180                 185                 190

Leu Tyr Thr Val Arg Phe Thr Ala Gln Glu Leu Trp Gly Pro Glu Gly
                195                 200                 205

Asp Pro Asn Ser Ser Val Tyr Tyr Asp Cys Trp Glu Pro Tyr Ile Glu
            210                 215                 220

Leu Val Asp Thr Lys Ala Ala Ala Ala
225                 230
```

<210> SEQ ID NO 68
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 68

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Gly Glu Tyr Leu
    50                  55                  60

Glu Ser Pro Tyr Tyr Trp His Trp Ile Arg Thr Tyr Ile His Asn Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
            115                 120                 125

Ala Ser Arg Glu Val Asp Arg Pro Pro Lys Phe Lys Glu Gly Asp Val
            130                 135                 140

Val Arg Phe Ser Thr Asn Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
                180                 185                 190

Leu Tyr Thr Val Arg Phe Thr Ala Gln Glu Leu Trp Gly Pro Glu Gly
                195                 200                 205

Asp Pro Asn Ser Ser Val Tyr Tyr Asp Cys Trp Glu Pro Tyr Ile Glu
            210                 215                 220

Leu Val Asp Thr Lys Ala Ala Ala Ala
```

<210> SEQ ID NO 69
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 69

Met Asn Gly Met Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Val
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His Asn Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Arg His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Tyr Ser Val Tyr Tyr Asp Cys Trp Glu Pro Tyr Ile Glu
    210                 215                 220

Leu Val Asp Thr Lys Ala Ala Ala
225                 230

<210> SEQ ID NO 70
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 70

Met Asn Gly Met Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Thr Glu Tyr Leu
    50                  55                  60

Glu Ser Pro Tyr Tyr Trp His Trp Ile Arg Thr Tyr Ile His Asn Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Ser Trp Glu Pro Tyr Ile Glu
    210                 215                 220

Leu Val Asp Thr Lys Ala Ala Ala
225                 230

<210> SEQ ID NO 71
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 71

Met Asn Gly Met Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
                20                  25                  30

Ala Phe Ala Met Phe Pro Ala Thr Phe Arg Ala Gly Phe Met Gly Leu
            35                  40                  45

Asp Glu Phe Arg Phe Gly Ile Glu Gln Met Asn Pro Ala Glu Tyr Leu
        50                  55                  60

Glu Ser Pro Tyr Tyr Trp His Trp Ile Arg Thr Tyr Ile His Asn Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Gly Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

```
Leu Tyr Thr Val Arg Phe Thr Ala Gln Glu Leu Trp Gly Pro Glu Gly
            195                 200                 205

Asp Pro Asn Ser Ser Val Tyr Tyr Ser Cys Trp Glu Pro Tyr Ile Glu
            210                 215                 220

Leu Val Asp Thr Lys Ala Ala Ala
225                 230
```

<210> SEQ ID NO 72
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 72

```
Met Asn Gly Val Tyr Asp Val Gly Gly Thr Asp Gly Leu Gly Pro Ile
1               5                   10                  15

Asn Arg Pro Ala Asp Glu Pro Val Phe Arg Ala Glu Trp Glu Lys Val
            20                  25                  30

Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
    50                  55                  60

Glu Ser Pro Tyr Tyr Trp His Trp Ile Arg Thr Tyr Ile His Asn Gly
65                  70                  75                  80

Val Arg Thr Gly Lys Ile Asp Leu Glu Glu Leu Glu Arg Arg Thr Gln
                85                  90                  95

Tyr Tyr Arg Glu Asn Pro Asp Ala Pro Leu Pro Glu His Glu Gln Lys
            100                 105                 110

Pro Glu Leu Ile Glu Phe Val Asn Gln Ala Val Tyr Gly Gly Leu Pro
        115                 120                 125

Ala Ser Arg Glu Val Asp Arg Pro Lys Phe Lys Glu Gly Asp Val
    130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
            180                 185                 190

Leu Tyr Thr Val Arg Phe Thr Ala Gln Glu Leu Trp Gly Pro Glu Gly
        195                 200                 205

Asp Pro Asn Ser Ser Val Tyr Tyr Asp Cys Trp Glu Pro Tyr Ile Glu
    210                 215                 220

Leu Val Asp Thr Lys Glu Ala Ala Ala
225                 230
```

<210> SEQ ID NO 73
<211> LENGTH: 233
<212> TYPE: PRT
<213> ORGANISM: Artificial
<220> FEATURE:
<223> OTHER INFORMATION: Modified nitrile hydratase beta-subunit

<400> SEQUENCE: 73

```
Met Asn Gly Val Tyr Asp Val Gly Gly Asp Asp Gly Leu Gly Pro Ile
1               5                   10                  15

Asn Arg Pro Ala Asp Glu Pro Val Phe Arg Ala Glu Trp Glu Lys Val
            20                  25                  30
```

```
Ala Phe Ala Met Phe Pro Ala Thr Phe Arg Ala Gly Phe Met Gly Leu
        35                  40                  45

Asp Glu Phe Arg Phe Gly Ile Glu Gln Met Asn Pro Ala Glu Tyr Leu
 50                  55                  60

Glu Ser Pro Tyr Tyr Trp His Trp Ile Arg Thr Tyr Ile His Asn Gly
 65                  70                  75                  80

Val Arg Thr Gly Lys Ile Asp Leu Glu Leu Glu Arg Arg Thr Gln
                85                  90                  95

Tyr Tyr Arg Glu Asn Pro Asp Ala Pro Leu Pro Glu His Glu Gln Lys
                100                 105                 110

Pro Glu Leu Ile Glu Val Val Asn Gln Ala Val Tyr Gly Gly Leu Pro
                115                 120                 125

Ala Ser Arg Glu Val Asp Arg Pro Pro Lys Phe Lys Glu Gly Asp Val
        130                 135                 140

Val Arg Phe Ser Thr Ala Ser Pro Lys Gly His Ala Arg Arg Ala Arg
145                 150                 155                 160

Tyr Val Arg Gly Lys Thr Gly Thr Val Val Lys His His Gly Ala Tyr
                165                 170                 175

Ile Tyr Pro Asp Thr Ala Gly Asn Gly Leu Gly Glu Cys Pro Glu His
                180                 185                 190

Leu Tyr Thr Val Arg Phe Thr Glu Gln Glu Leu Trp Gly Pro Glu Gly
                195                 200                 205

Asp Pro Asn Ser Ser Val Tyr Tyr Asp Cys Trp Pro Tyr Ile Glu
        210                 215                 220

Leu Val Asp Thr Lys Glu Ala Ala Ala
225                 230

<210> SEQ ID NO 74
<211> LENGTH: 33
<212> TYPE: DNA
<213> ORGANISM: Artificial
<220> FEATURE:
<223> OTHER INFORMATION: Oligonucleotide to act as a PCR primer

<400> SEQUENCE: 74
tacgaattct aaggaggtct cagcatgaac ggc                                   33

<210> SEQ ID NO 75
<211> LENGTH: 144
<212> TYPE: PRT
<213> ORGANISM: Pseudonocardia thermophila

<400> SEQUENCE: 75

Met Ser Ala Glu Ala Lys Val Arg Leu Lys His Cys Pro Thr Ala Glu
 1               5                  10                  15

Asp Arg Ala Ala Ala Asp Ala Leu Leu Ala Gln Leu Pro Gly Gly Asp
                20                  25                  30

Arg Ala Leu Asp Arg Gly Phe Asp Glu Pro Trp Gln Leu Arg Ala Phe
        35                  40                  45

Ala Leu Ala Val Ala Ala Cys Arg Ala Gly Arg Phe Glu Trp Lys Gln
 50                  55                  60

Leu Gln Gln Ala Leu Ile Ser Ser Ile Gly Glu Trp Glu Arg Thr His
 65                  70                  75                  80

Asp Leu Asp Asp Pro Ser Trp Ser Tyr Tyr Glu His Phe Val Ala Ala
                85                  90                  95

Leu Glu Ser Val Leu Gly Glu Glu Gly Ile Val Glu Pro Glu Ala Leu
```

```
              100                 105                 110
Asp Glu Arg Thr Ala Glu Val Leu Ala Asn Pro Pro Asn Lys Asp His
            115                 120                 125

His Gly Pro His Leu Glu Pro Val Ala Val His Pro Ala Val Arg Ser
    130                 135                 140
```

MUTANT NITRILE HYDRATASE, NUCLEIC ACID CODING SAID MUTANT NITRILE HYDRATASE, EXPRESSION VECTOR AND TRANSFORMANT INCLUDING SAID NUCLEIC ACID, PRODUCTION METHOD FOR SAID MUTANT NITRILE HYDRATASE, AND PRODUCTION METHOD FOR AMIDE COMPOUND

TECHNICAL FIELD

The present disclosure relates to a mutant nitrile hydratase, a nucleic acid coding the mutant nitrile hydratase, an expression vector and a transformant including the nucleic acid, a production method for the mutant nitrile hydratase, and a production method for an amide compound.

BACKGROUND ART

Nitrile hydratase is an enzyme having nitrile hydration activity which converts a nitrile group of various compounds into an amide group by hydration and is used in an industrial production step of an amide compound utilizing an enzymatic reaction.

In recent years, the demand level for an industrial production technology of an amide compound tends to increase. In view of these circumstances, various studies have been made so far to reduce the running cost of the nitrile hydratase in a production cost of the amide compound. In particular, regarding the nitrile hydratase, a number of reports have been made on a technology relating to a mutant capable of improving an activity value per unit weight of the nitrile hydratase (Japanese Patent Application Laid-Open (JP-A) Nos. H09-275978, 2004-194588, and 2005-160403, International Publication Nos. WO 2004/056990 and 2010/055666, and JP-A Nos. 2007-143409 and 2008-253182, and the like).

Here, in a typical production step of an industrial amide compound utilizing an enzymatic reaction, generally, a reaction step of performing a reaction of synthesizing an amide compound from a nitrile compound using a catalytic action of a nitrile hydratase in a solution adjusted to have a pH of usually from 7 to 9; and a purification step of adjusting the pH of the solution to from 3.5 to 6.5 and removing the nitrile hydratase present in the solution by adsorption using activated carbon at the above-described pH to obtain a purified amide compound are performed in this order (JP-A No. 2001-270857).

SUMMARY OF INVENTION

Technical Problem

The present inventors have performed intensive studies to improve a production efficiency of an industrial amide compound using a nitrile hydratase as compared with the conventional art. As a result, the present inventors found that continuously performing a reaction for synthesizing an amide compound from a nitrile compound using a catalytic action of the nitrile hydratase even in the purification step performed in an acidic pH range is effective as a design guideline.

In general, however, an optimum pH of a wild-type nitrile hydratase is from 7 to 9, and an activity of the wild-type nitrile hydratase is greatly decreased under the condition of from pH 3.5 to pH 6.5. Therefore, even when the wild-type nitrile hydratase is used, an enzymatic reaction in the purification step is not generated to a satisfactory level. In addition, various nitrile hydratase mutants have been reported as described above, but the activity is greatly decreased under acidic conditions as used in the purification step. Thus, a technology for a nitrile hydratase mutant exhibiting excellent pH stability of the enzyme activity catalyzing the reaction of synthesizing an amide compound from a nitrile compound in the purification step under acidic conditions has not been reported so far. Under relatively strong acidic conditions, particularly pH 5.0 or less, the protein has a higher tendency to deactivate, and a technology for the nitrile hydratase mutant in which the enzyme activity is maintained well even under the pH conditions has not been reported so far.

Therefore, the disclosure provides a technology for a mutant nitrile hydratase having a new mutation point, in which stability against the pH of the enzyme activity catalyzing the synthesis reaction of the amide compound from the nitrile compound is improved. More specifically, there is provided a technology for the mutant nitrile hydratase that maintains an excellent enzyme activity even in an acidic range having a pH of from 3.5 to 6.5. Even more specifically, there is provided a technology for the mutant nitrile hydratase that maintains an excellent enzyme activity even in a relatively strong acidic range having a pH of from 3.5 to 5.0.

Solution to Problem

The disclosure includes the following aspects:

<1> A mutant nitrile hydratase that is derived from *Pseudonocardia thermophila* and has an α subunit and a β subunit, the mutant nitrile hydratase including at least one amino acid residue substitution selected from the group consisting of the following amino acid residue substitutions (a) to (e):

(a) a substitution of the 40th amino acid residue from an N terminal of the α subunit with Asn,
(b) a substitution of the 43rd amino acid residue from the N terminal of the α subunit with Val,
(c) a substitution of the 205th amino acid residue from an N terminal of the β subunit with Val,
(d) a substitution of the 206th amino acid residue from the N terminal of the β subunit with Gin, and
(e) a substitution of the 215th amino acid residue from the N terminal of the β subunit with Asn.

<2> The mutant nitrile hydratase described in <1>, including: two or more amino acid residue substitutions selected from the group consisting of the amino acid residue substitutions (a) to (e).

<3> The mutant nitrile hydratase described in <1> or <2>, including: the amino acid residue substitution (b); and at least one selected from the group consisting of the amino acid residue substitutions (a), (c), (d), and (e).

<4> The mutant nitrile hydratase described in any one of <1> to <3> in which the 36th amino acid from the N terminal in the amino acid sequence of the α subunit is a Trp residue.

<5> The mutant nitrile hydratase described in any one of <1> to <3> in which the 36th amino acid from the N terminal in the amino acid sequence of the α subunit is Met, Ser, Gly, or Ala.

<6> The mutant nitrile hydratase described in any one of <1> to <5> in which the amino acid sequence of the α subunit satisfies one or more of the following conditions (1) to (13):

(1) the 6th amino acid residue from the N terminal is Thr or Ala,
(2) the 13th amino acid residue from the N terminal is Leu,
(3) the 19th amino acid residue from the N terminal is Val,
(4) the 27th amino acid residue from the N terminal is Ile,
(5) the 48th amino acid residue from the N terminal is Gln,
(6) the 71st amino acid residue from the N terminal is His,
(7) the 92nd amino acid residue from the N terminal is Glu,
(8) the 94th amino acid residue from the N terminal is Ile,
(9) the 126th amino acid residue from the N terminal is Tyr,
(10) the 148th amino acid residue from the N terminal is Asp,
(11) the 188th amino acid residue from the N terminal is Gly,
(12) the 197th amino acid residue from the N terminal is Cys, and
(13) the 204th amino acid residue from the N terminal is Arg.

<7> The mutant nitrile hydratase described in any one of <1> to <6> in which the amino acid sequence of the β subunit satisfies at least one of the following conditions (15) to (47):
(15) the 4th amino acid residue from the N terminal is Met,
(16) the 8th amino acid residue from the N terminal is Ala,
(17) the 10th amino acid residue from the N terminal is Asp,
(18) the 24th amino acid residue from the N terminal is Ile,
(19) the 33rd amino acid residue from the N terminal is Val, or Met,
(20) the 37th amino acid residue from the N terminal is Val, or Leu,
(21) the 40th amino acid residue from the N terminal is Ile, Val, or Leu,
(22) the 41st amino acid residue from the N terminal is Ile,
(23) the 46th amino acid residue from the N terminal is Lys,
(24) the 48th amino acid residue from the N terminal is Val,
(25) the 51st amino acid residue from the N terminal is Val,
(26) the 61st amino acid residue from the N terminal is Val, Gly, Trp, Ser, Leu, or Thr,
(27) the 79th amino acid residue from the N terminal is Asn,
(28) the 96th amino acid residue from the N terminal is Arg,
(29) the 107th amino acid residue from the N terminal is Met,
(30) the 108th amino acid residue from the N terminal is Asp or Arg,
(31) the 110th amino acid residue from the N terminal is Asn,
(32) the 112th amino acid residue from the N terminal is Val, or Ile,
(33) the 118th amino acid residue from the N terminal is Val,
(34) the 127th amino acid residue from the N terminal is Ser,
(35) the 146th amino acid residue from the N terminal is Gly,
(36) the 150th amino acid residue from the N terminal is Asn or Ser,
(37) the 160th amino acid residue from the N terminal is Cys, Trp, or Met,
(38) the 168th amino acid residue from the N terminal is Glu,
(39) the 176th amino acid residue from the N terminal is Ala, Thr, Met, or Cys,
(40) the 186th amino acid residue from the N terminal is Arg,
(41) the 200th amino acid residue from the N terminal is Glu,
(42) the 212th amino acid residue from the N terminal is Tyr,
(43) the 217th amino acid residue from the N terminal is Val, His, Met, Gly, Ser, Leu, or Cys,
(44) the 218th amino acid residue from the N terminal is Met, or Ser,
(45) the 226th amino acid residue from the N terminal is Ile,
(46) the 230th amino acid residue from the N terminal is Glu, and
(47) the 231st amino acid residue from the N terminal is Val.

<8> The mutant nitrile hydratase described in any one of <1> to <7>, including: at least one amino acid residue substitution selected from the group consisting of the amino acid residue substitutions (a) to (e) in any one of the following *Pseudonocardia thermophila*-derived nitrile hydratases [1] to [49]:

[1] a nitrile hydratase that has an α subunit having an amino acid sequence of SEQ ID NO: 1; and a β subunit having an amino acid sequence of SEQ ID NO: 2,
[2] a nitrile hydratase that has an α subunit having an amino acid sequence of SEQ ID NO: 16; and a β subunit having an amino acid sequence of SEQ ID NO: 33,
[3] a nitrile hydratase that has an α subunit having an amino acid sequence of SEQ ID NO: 17; and a β subunit having an amino acid sequence of SEQ ID NO: 33,
[4] a nitrile hydratase that has an α subunit having an amino acid sequence of SEQ ID NO: 18; and a β subunit having an amino acid sequence of SEQ ID NO: 34,
[5] a nitrile hydratase that has an α subunit having an amino acid sequence of SEQ ID NO: 19; and a β subunit having an amino acid sequence of SEQ ID NO: 34,
[6] a nitrile hydratase that has an α subunit having an amino acid sequence of SEQ ID NO: 20; and a β subunit having an amino acid sequence of SEQ ID NO: 35,
[7] a nitrile hydratase that has an α subunit having an amino acid sequence of SEQ ID NO: 20; and a β subunit having an amino acid sequence of SEQ ID NO: 36.
[8] a nitrile hydratase that has an α subunit having an amino acid sequence of SEQ ID NO: 21; and a β subunit having an amino acid sequence of SEQ ID NO: 37,
[9] a nitrile hydratase that has an α subunit having an amino acid sequence of SEQ ID NO: 21; and a β subunit having an amino acid sequence of SEQ ID NO: 38,
[10] a nitrile hydratase that has an α subunit having an amino acid sequence of SEQ ID NO: 21; and a β subunit having an amino acid sequence of SEQ ID NO: 39,
[11] a nitrile hydratase that has an α subunit having an amino acid sequence of SEQ ID NO: 21; and a β subunit having an amino acid sequence of SEQ ID NO: 40,
[12] a nitrile hydratase that has an α subunit having an amino acid sequence of SEQ ID NO: 18; and a β subunit having an amino acid sequence of SEQ ID NO: 41,
[13] a nitrile hydratase that has an α subunit having an amino acid sequence of SEQ ID NO: 18; and a β subunit having an amino acid sequence of SEQ ID NO: 42,
[14] a nitrile hydratase that has an α subunit having an amino acid sequence of SEQ ID NO: 21; and a β subunit having an amino acid sequence of SEQ ID NO: 43.
[15] a nitrile hydratase that has an α subunit having an amino acid sequence of SEQ ID NO: 22; and a β subunit having an amino acid sequence of SEQ ID NO: 44,
[16] a nitrile hydratase that has an α subunit having an amino acid sequence of SEQ ID NO: 23; and a β subunit having an amino acid sequence of SEQ ID NO: 45,
[17] a nitrile hydratase that has an α subunit having an amino acid sequence of SEQ ID NO: 24; and a β subunit having an amino acid sequence of SEQ ID NO: 46,
[18] a nitrile hydratase that has an α subunit having an amino acid sequence of SEQ ID NO: 25; and a β subunit having an amino acid sequence of SEQ ID NO: 47,
[19] a nitrile hydratase that has an α subunit having an amino acid sequence of SEQ ID NO: 18; and a β subunit having an amino acid sequence of SEQ ID NO: 48,

[20] a nitrile hydratase that has an α subunit having an amino acid sequence of SEQ ID NO: 23; and a β subunit having an amino acid sequence of SEQ ID NO: 49,
[21] a nitrile hydratase that has an α subunit having an amino acid sequence of SEQ ID NO: 16; and a β subunit having an amino acid sequence of SEQ ID NO: 50.
[22] a nitrile hydratase that has an α subunit having an amino acid sequence of SEQ ID NO: 26; and a β subunit having an amino acid sequence of SEQ ID NO: 51,
[23] a nitrile hydratase that has an α subunit having an amino acid sequence of SEQ ID NO: 27; and a β subunit having an amino acid sequence of SEQ ID NO: 52,
[24] a nitrile hydratase that has an α subunit having an amino acid sequence of SEQ ID NO: 28; and a β subunit having an amino acid sequence of SEQ ID NO: 53,
[25] a nitrile hydratase that has an α subunit having an amino acid sequence of SEQ ID NO: 17; and a β subunit having an amino acid sequence of SEQ ID NO: 54,
[26] a nitrile hydratase that has an α subunit having an amino acid sequence of SEQ ID NO: 29; and a β subunit having an amino acid sequence of SEQ ID NO: 55,
[27] a nitrile hydratase that has an α subunit having an amino acid sequence of SEQ ID NO: 18; and a β subunit having an amino acid sequence of SEQ ID NO: 56,
[28] a nitrile hydratase that has an α subunit having an amino acid sequence of SEQ ID NO: 18; and a β subunit having an amino acid sequence of SEQ ID NO: 57,
[29] a nitrile hydratase that has an α subunit having an amino acid sequence of SEQ ID NO: 30; and a β subunit having an amino acid sequence of SEQ ID NO: 58,
[30] a nitrile hydratase that has an α subunit having an amino acid sequence of SEQ ID NO: 29; and a β subunit having an amino acid sequence of SEQ ID NO: 59,
[31] a nitrile hydratase that has an α subunit having an amino acid sequence of SEQ ID NO: 31; and a β subunit having an amino acid sequence of SEQ ID NO: 60,
[32] a nitrile hydratase that has an α subunit having an amino acid sequence of SEQ ID NO: 18; and a β subunit having an amino acid sequence of SEQ ID NO: 61,
[33] a nitrile hydratase that has an α subunit having an amino acid sequence of SEQ ID NO: 32; and a β subunit having an amino acid sequence of SEQ ID NO: 62,
[34] a nitrile hydratase that has an α subunit having an amino acid sequence of SEQ ID NO: 30; and a β subunit having an amino acid sequence of SEQ ID NO: 63,
[35] a nitrile hydratase that has an α subunit having an amino acid sequence of SEQ ID NO: 30; and a β subunit having an amino acid sequence of SEQ ID NO: 64.
[36] a nitrile hydratase that has an α subunit having an amino acid sequence of SEQ ID NO: 30; and a β subunit having an amino acid sequence of SEQ ID NO: 65,
[37] a nitrile hydratase that has an α subunit having an amino acid sequence of SEQ ID NO: 25; and a β subunit having an amino acid sequence of SEQ ID NO: 54,
[38] a nitrile hydratase that has an α subunit having an amino acid sequence of SEQ ID NO: 30; and a β subunit having an amino acid sequence of SEQ ID NO: 66,
[39] a nitrile hydratase that has an α subunit having the amino acid sequence of SEQ ID NO: 1; and a β subunit having an amino acid sequence of SEQ ID NO: 67,
[40] a nitrile hydratase that has an α subunit having the amino acid sequence of SEQ ID NO: 1; and a β subunit having an amino acid sequence of SEQ ID NO: 68,
[41] a nitrile hydratase that has an α subunit having the amino acid sequence of SEQ ID NO: 1; and a β subunit having an amino acid sequence of SEQ ID NO: 69,
[42] a nitrile hydratase that has an α subunit having the amino acid sequence of SEQ ID NO: 1; and a β subunit having an amino acid sequence of SEQ ID NO: 70,
[43] a nitrile hydratase that has an α subunit having the amino acid sequence of SEQ ID NO: 1; and a β subunit having an amino acid sequence of SEQ ID NO: 71,
[44] a nitrile hydratase that has an α subunit having the amino acid sequence of SEQ ID NO: 21; and a β subunit having an amino acid sequence of SEQ ID NO: 72,
[45] a nitrile hydratase that has an α subunit having the amino acid sequence of SEQ ID NO: 1; and a β subunit having an amino acid sequence of SEQ ID NO: 73,
[46] a nitrile hydratase in which the 36th amino acid residue from the N terminal of the α subunit in any one of the nitrile hydratases [1] to 1451 is a Trp residue,
[47] a nitrile hydratase that has the α subunit of a nitrile hydratase (A) of any one of [1] to [46] or an α subunit variant consisting of an amino acid sequence having 90% or more sequence identity with the α subunit; and a β subunit of the nitrile hydratase (A) or a β subunit variant consisting of an amino acid sequence having 90% or more sequence identity with the β subunit, wherein at least one of the α subunit or the β subunit is the α subunit variant or the β subunit variant, and
[48] a nitrile hydratase in which the total number of amino acid residues added, substituted, deleted, and/or inserted is from 1 to 10 (excluding the amino acid residues to be substituted in (a) and (b)) in the α subunit of a nitrile hydratase (B) of any one of [1] to [46], and the total number of amino acid residues added, substituted, deleted, and/or inserted is from 1 to 10 (excluding the amino acid residues to be substituted in (c) to (e)) in the β subunit of the nitrile hydratase (B).

<9> A nucleic acid encoding the mutant nitrile hydratase described in any one of <1> to <8>.

<10> A vector including the nucleic acid described in <9>.

<11> The vector described in <10>, which is an expression vector.

<12> A transformant including the expression vector described in <11>.

<13> A method of producing a mutant nitrile hydratase, the method including: culturing the transformant described in <12> in a medium; and recovering the mutant nitrile hydratase described in any one of <1> to <8> from at least one of the cultured transformant and the medium.

<14> A mutant nitrile hydratase obtained by the method of producing described in <13>.

<15> A method of producing an amide compound, the method including: bringing the mutant nitrile hydratase described in any one of <1> to <8> and <14> into contact with a nitrile compound.

<16> The method of producing an amide compound described in <15>, further including: removing impurities from a solution containing an amide compound at pH 3.5 to pH 6.5.

<17> The method of producing an amide compound described in <15> or <16>, further including: purifying the amide compound with activated carbon.

Advantageous Effects of Invention

According to the disclosure, it is possible to provide a technology for a mutant nitrile hydratase having a new mutation point, in which stability against the pH of the enzyme activity catalyzing the synthesis reaction of the amide compound from the nitrile compound is improved.

More specifically, it is possible to provide a technology for the mutant nitrile hydratase that maintains an excellent enzyme activity even in an acidic range having a pH of from 3.5 to 6.5. Even more specifically, it is possible to provide a technology for the mutant nitrile hydratase that maintains an excellent enzyme activity even in a relatively strong acidic range having a pH of from 3.5 to 5.0.

DESCRIPTION OF EMBODIMENTS

<Mutant Nitrile Hydratase>

The disclosure provides a mutant nitrile hydratase (hereinafter, referred to as a mutant nitrile hydratase A) that is derived from *Pseudonocardia thermophila* and has an α subunit and a β subunit, including at least one amino acid residue substitution selected from the group consisting of the following amino acid residue substitutions (a) to (e):
(a) a substitution of the 40th amino acid residue from an N terminal of the α subunit with Asn,
(b) a substitution of the 43rd amino acid residue from the N terminal of the α subunit with Val,
(c) a substitution of the 205th amino acid residue from an N terminal of the β subunit with Val,
(d) a substitution of the 206th amino acid residue from the N terminal of the β subunit with Gln, and
(e) a substitution of the 215th amino acid residue from the N terminal of the β subunit with Asn.

Mutants including at least one or more of the amino acid residue substitutions (a) to (e) described above have not been reported so far. That is, all of the amino acid residue substitutions (a) to (e) included in the mutant nitrile hydratase can be said to be a mutation that has not been reported so far. These amino acid residue substitutions (a) to (e) are also referred to as amino acid residue substitution group A below. In addition, the mutant nitrile hydratase according to the disclosure including the mutation described above is an enzyme capable of exhibiting an enzyme activity having stability over a wide pH range as compared with a conventional nitrile hydratase mutant with respect to a synthesis reaction of an amide compound from a nitrile compound. This point is explained in detail in Examples.

Attempts have been made to obtain mutants of wild-type *Pseudonocardia thermophila*-derived nitrile hydratase. However, these attempts are mainly intended for improving an enzyme activity under optimum pH conditions of enzymes, and there was no study on the enzyme activity under acidic conditions opposite to the optimum pH condition of the enzyme. The enzyme activity of nitrile hydratase under acidic conditions deviating from optimal conditions was first discovered by the present inventors, and the present inventors found that the above new amino acid residue mutation is effective.

Hereinafter, the mutant nitrile hydratase according to the disclosure is described in more detail. The description of the nucleotide sequence in the disclosure may be provided focusing on the sequence on one strand even in a case in which the nucleic acid chain holding the nucleotide sequence forms a double strand. However, in the case of other chains of the double strand, descriptions of the sequences should be applied by substitution with their complementary sequences.

In the disclosure, the term "step" is included in this term as long as an intended purpose of the step is achieved not only in an independent step but also in a case in which the step cannot be clearly distinguished from other steps.

In the disclosure, a numerical range indicated by using "from . . . to" indicates a range including numerical values described before and after "from . . . to" as the minimum value and the maximum value, respectively.

In the disclosure, an amount of each component in the composition means a total amount of the plurality of substances present in the composition, unless otherwise specified, in a case in which the plurality of substances corresponding to each component in the composition are present.

In the disclosure, *Pseudonocardia thermophila*-derived nitrile hydratase has a concept which includes not only a wild-type *Pseudonocardia thermophila*-derived nitrile hydratase that has an α subunit having an amino acid sequence of SEQ ID NO: 1 and a β subunit having an amino acid sequence of SEQ ID NO: 2 but also modified nitrile hydratase in which modification has been made with respect to the wild-type *Pseudonocardia thermophila*-derived nitrile hydratase to the extent that can be recognized as a modified sequence of the wild-type *Pseudonocardia thermophila*-derived nitrile hydratase by a person skilled in the art. The modified nitrile hydratase included in the concept of the *Pseudonocardia thermophila*-derived nitrile hydratase includes modified nitrile hydratase in which one or more modifications have been made with respect to the wild-type *Pseudonocardia thermophila*-derived nitrile hydratase, the modification being selected from the group consisting of (i) substitution of one or more amino acid residues with other amino acid residue, (ii) deletion of one or more amino acid residues other than (a) to (e), (iii) insertion of amino acid residues, (iv) addition of an amino acid residue to one or both of the N terminal and C terminal of the amino acid sequence of the α subunit, and (v) addition of an amino acid residue to one or both of the N terminal and C terminal of the amino acid sequence of the β subunit.

In the α subunit of the modified nitrile hydratase, the number of substituted amino acid residues is, for example, from 1 to 20, from 1 to 15, from 1 to 10, from 1 to 8, from 1 to 7, from 1 to 6, from 1 to 5, from 1 to 4, from 1 to 3, from 1 to 2, or 1. The number of substituted amino acid residues may be zero.

In the β subunit of the modified nitrile hydratase, the number of substituted amino acid residues is, for example, from 1 to 20, from 1 to 15, from 1 to 10, from 1 to 8, from 1 to 7, from 1 to 6, from 1 to 5, from 1 to 4, from 1 to 3, from 1 to 2, or 1. The number of substituted amino acid residues may be zero.

In the α subunit of the modified nitrile hydratase, the number of deleted amino acid residues is, for example, from 1 to 10, from 1 to 7, from 1 to 4, from 1 to 2, or 1. The number of deleted amino acid residues may be zero.

In the β subunit of the modified nitrile hydratase, the number of deleted amino acid residues is, for example, from 1 to 10, from 1 to 7, from 1 to 4, from 1 to 2, or 1. The number of deleted amino acid residues may be zero.

In the α subunit of the modified nitrile hydratase, the number of inserted amino acid residues is, for example, from 1 to 10, from 1 to 7, from 1 to 4, from 1 to 2, or 1. The number of inserted amino acid residues may be zero.

In the β subunit of the modified nitrile hydratase, the number of inserted amino acid residues is, for example, from 1 to 10, from 1 to 7, from 1 to 4, from 1 to 2, or 1. The number of inserted amino acid residues may be zero.

In the α subunit of the modified nitrile hydratase, the total number of substituted, deleted or inserted amino acid residues is, for example, from 1 to 20, from 1 to 14, from 1 to 8, from 1 to 4, from 1 to 2, or 1. In a case in which there is a terminal-addition, and the like, the total number of substituted, deleted or inserted amino acid residues may be zero.

In the β subunit of the modified nitrile hydratase, the total number of substituted, deleted or inserted amino acid residues is, for example, from 1 to 20, from 1 to 14, from 1 to 8, from 1 to 4, from 1 to 2, or 1. In a case in which there is a terminal-addition, and the like, the total number of substituted, deleted or inserted amino acid residues may be zero.

In the α subunit of the modified nitrile hydratase, the number of terminal-added amino acid residues is, for example, from 1 to 60, from 1 to 40, from 1 to 20, from 1 to 10, from 1 to 5, from 1 to 3, or 1 per one terminal. The number of added amino acid residues may be zero.

In the β subunit of the modified nitrile hydratase, the number of terminal-added amino acid residues is, for example, from 1 to 60, from 1 to 40, from 1 to 20, from 1 to 10, from 1 to 5, from 1 to 3, or 1 per one terminal. The number of added amino acid residues may be zero. The terminal-added amino acid residue may be, for example, a secretion signal sequence. The terminal-added amino acid residue may be present only at the N terminal, only at the C terminal, or at both the N terminal and the C terminal.

Similarity between the modified nitrile hydratase and the wild-type *Pseudonocardia thermophila*-derived nitrile hydratase may also be expressed by sequence identity.

The amino acid sequence of the α subunit of the modified nitrile hydratase has, for example, 70% or more sequence identity, 80% or more sequence identity, 85% or more sequence identity, 90% or more sequence identity, 95% or more sequence identity, 96% or more sequence identity, 97% or more sequence identity, 98% or more sequence identity, or 99% or more sequence identity with the amino acid sequence of the α subunit of the wild-type *Pseudonocardia thermophila*-derived nitrile hydratase represented by SEQ ID NO: 1.

The amino acid sequence of the β subunit of the modified nitrile hydratase has, for example, 70% or more sequence identity, 80% or more sequence identity, 85% or more sequence identity, 90% or more sequence identity, 95% or more sequence identity, 96% or more sequence identity, 97% or more sequence identity, 98% or more sequence identity, or 99% or more sequence identity with the amino acid sequence of the β subunit of the wild-type *Pseudonocardia thermophila*-derived nitrile hydratase represented by SEQ ID NO: 2.

Further, alignment between sequences can be performed with ClustalW (1.83), and can be performed by using initial parameters (including gap open penalty: 10, gap extension penalty: 0.05).

In a case in which the amino acid sequence of the modified nitrile hydratase is aligned with the amino acid sequence of the wild-type *Pseudonocardia thermophila*-derived nitrile hydratase, depending on a modification mode of the modified nitrile hydratase, there is a case in which a distance from the N terminal of the subunits defined as described above is different even in a case in which amino acid residues correspond to each other on the alignment. In the disclosure, in this case, with respect to the modified nitrile hydratase, the Xth amino acid residue from the N terminal of the subunit refers to an amino acid residue corresponding to the Xth amino acid residue on the alignment from the N terminal of the corresponding subunit of the wild-type *Pseudonocardia thermophila*-derived nitrile hydratase. For example, in the disclosure, "the 40th amino acid residue from the N terminal of the α subunit", "the Asp residue at the 40th position from the N terminal of the α subunit", or "Asp residue which is the 40th amino acid residue from the N terminal of the α subunit" may be located at a position other than the 40th position from the N terminal of the α subunit on the amino acid sequence of the modified nitrile hydratase. For example, the amino acid residue at the 41st position from the N terminal of the α subunit of the modified nitrile hydratase (which is not necessarily Asp) may correspond to, as a result of the insertion of the amino acid residue, the Asp residue which is the 40th amino acid residue from the N terminal of the α subunit of the wild-type *Pseudonocardia thermophila*-derived nitrile hydratase. In this case, in the description of the disclosure, "the 40th amino acid residue from the N terminal of the α subunit", "the Asp residue at the 40th position from the N terminal of the α subunit", or "Asp residue which is the 40th amino acid residue from the N terminal of the α subunit" refers to the 41st amino acid residue from the N terminal of the α subunit in the modified nitrile hydratase.

In the wild-type *Pseudonocardia thermophila*-derived nitrile hydratase, the Met residue at the head of SEQ ID NO: 1 is the 1st amino acid residue from the N terminal of the amino acid sequence of the α subunit, the 40th amino acid residue from the N terminal of the amino acid sequence of the α subunit is the Asp residue, and the 43th amino acid residue from the N terminal of the amino acid sequence of the α subunit is the Ala residue. Further, in the wild-type *Pseudonocardia thermophila*-derived nitrile hydratase, the Met residue at the head of SEQ ID NO: 2 is the 1st amino acid residue from the N terminal of the amino acid sequence of the β subunit, the 205th amino acid residue from the N terminal of the amino acid sequence of the β subunit is the Gly residue, the 206th amino acid residue from the N terminal of the amino acid sequence of the β subunit is the Pro residue, and the 215th amino acid residue from the N terminal of the amino acid sequence of the β subunit is the Tyr residue.

The sequence of the modified nitrile hydratase that can be used as introduction targets for one or more among the amino acid residue substitutions (a) to (e) can be selected from sequences of nitrile hydratase registered in GenBank provided by National Center for Biotechnology Information (NCBI) or sequences of nitrile hydratase described in the known literatures. Further, the sequence of the modified nitrile hydratase can be selected from sequences of the modified nitrile described in JP-A Nos. H09-275978, 2004-194588, 2005-160403, WO 2004/056990, or WO 2010/055666 described above. In this case, in addition to the improvements described in these patent documents, a new effect of improving pH stability can be obtained by the introduction of one or more of the amino acid residue substitutions (a) to (e).

In addition, the modified nitrile hydratase that can be used as introduction targets for one or more among the amino acid residue substitutions (a) to (e) may be a nitrile hydratase in which the 36th amino acid residue from the N terminal (the amino acid residue corresponding to the Thr residue on the alignment at the 36th position from the N terminal in the amino acid sequence of wild-type *Pseudonocardia thermophila*-derived nitrile hydratase) is the Trp residue (hereinafter also referred to as amino acid residue substitution (f)). It is preferable to have the amino acid residue substitution (f) in addition to one or more of the amino acid residue substitutions (a) to (e) from the viewpoint of obtaining a mutant nitrile hydratase having more improved pH stability. In other words, in a case in which the amino acid residue substitution (f) is present, an effect of amino acid residue substitutions (a) to (e) tends to be stronger.

Further, for example, WO 2010/055666 discloses that introduction of amino acid residue substitution (hereinafter also referred to as amino acid residue substitution group B)

as described below with respect to the amino acid sequence of wild-type *Pseudonocardia thermophila*-derived nitrile hydratase.

Amino acid residue substitutions in the amino acid sequence of the α subunit (represented by the position based on the N terminal of the α subunit):

a substitution of Leu, which is the 6th amino acid residue, with Thr or Ala, a substitution of Ile, which is the 13th amino acid residue, with Leu, a substitution of Ala, which is the 19th amino acid residue, with Val, a substitution of Met, which is the 27th amino acid residue, with Ile, a substitution of Thr, which is the 36th amino acid residue, with Met, Ser, Gly, or Ala, a substitution of Asn, which is the 48th amino acid residue, with Gln, a substitution of Arg, which is the 71st amino acid residue, with His, a substitution of Asp, which is the 92nd amino acid residue, with Glu, a substitution of Met, which is the 94th amino acid residue, with Ile, a substitution of Phe, which is the 126th amino acid residue, with Tyr, a substitution of Gly, which is the 148th amino acid residue, with Asp, a substitution of Thr, which is the 188th amino acid residue, with Gly, a substitution of Gly, which is the 197th amino acid residue, with Cys, and a substitution of Val, which is the 204th amino acid residue, with Arg.

Amino acid residue substitutions in the amino acid sequence of the β subunit (represented by the position based on the N terminal of the β subunit):

a substitution of Val, which is the 4th amino acid residue, with Met, a substitution of Gly, which is the 8th amino acid residue, with Ala, a substitution of Thr, which is the 10th amino acid residue, with Asp, a substitution of Val, which is the 24th amino acid residue, with Ile, a substitution of Ala, which is the 33rd amino acid residue, with Val, or Met, a substitution of Phe, which is the 37th amino acid residue, with Val, or Leu, a substitution of Thr, which is the 40th amino acid residue, with Ile, Val, or Leu, a substitution of Phe, which is the 41st amino acid residue, with Ile, a substitution of Met, which is the 46th amino acid residue, with Lys, a substitution of Leu, which is the 48th amino acid residue, with Val, a substitution of Phe, which is the 51st amino acid residue, with Val, a substitution of Ala, which is the 61st amino acid residue, with Val, Gly, Trp, Ser, Leu, or Thr, a substitution of His, which is the 79th amino acid residue, with Asn, a substitution of Gln, which is the 96th amino acid residue, with Arg, a substitution of Pro, which is the 107th amino acid residue, with Met, a substitution of Glu, which is the 108th amino acid residue, with Asp or Arg.

a substitution of Glu, which is the 110th amino acid residue, with Asn, a substitution of Lys, which is the 112th amino acid residue, with Val, or Ile, a substitution of Phe, which is the 118th amino acid residue, with Val, a substitution of Leu, which is the 127th amino acid residue, with Ser, a substitution of Arg, which is the 146th amino acid residue, with Gly, a substitution of Ala, which is the 150th amino acid residue, with Asn or Ser, a substitution of Arg, which is the 160th amino acid residue, with Cys, Trp, or Met, a substitution of Thr, which is the 168th amino acid residue, with Glu, a substitution of Tyr, which is the 176th amino acid residue, with Ala, Thr, Met, or Cys, a substitution of Leu, which is the 186th amino acid residue, with Arg, a substitution of Ala, which is the 200th amino acid residue, with Glu, a substitution of Pro, which is the 206th amino acid residue, with Leu, a substitution of Ser, which is the 212th amino acid residue, with Tyr, a substitution of Asp, which is the 217th amino acid residue, with Val, His, Met, Gly, Ser, Leu, or Cys, a substitution of Cys, which is the 218th amino acid residue, with Met, or Ser, a substitution of Val, which is the 226th amino acid residue, with Ile, a substitution of Ala, which is the 230th amino acid residue, with Glu, and a substitution of Ala, which is the 231st amino acid residue, with Val.

The modified nitrile hydratase that can be used as introduction targets for one or more among the amino acid residue substitutions (a) to (e) may include one or more amino acid residue substitutions selected from the amino acid residue substitution group B, and may further have an amino acid residue substitution (f) in addition thereto when compared with the amino acid sequence of the wild-type *Pseudonocardia thermophila*-derived nitrile hydratase. Two or more amino acid residue substitutions may be included in combination. A number of examples of the combinations are also described in WO 2010/055666. In addition, the modified nitrile hydratase should have a nitrile hydratase activity.

For example, examples of a case in which three amino acid residue substitutions are included in combination may include:

a combination of Thr36Ser and Asp92Glu in the α subunit and Ala33Val in the β subunit, a combination of Met94Ile in the α subunit and Ala6Gly and Ala150Asn in the β subunit, a combination of Val4Met, Tyr176Ala, and Asp217Val in the β subunit.

a combination of Ala33Met, His79Asn, and Tyr176Thr in the β subunit, and a combination of Thr40Val, Cys218Met, and Val226Ile in the β subunit, and the like.

Further, for example, examples of a case in which eight amino acid residue substitutions are included in combination may include:

a combination of Ile13Leu, Ala19Val, Arg71His, and Phe126Tyr in the α subunit and Phe37Leu, Gln96Arg, Glu108Asp, and Ala200Glu in the β subunit (International Publication No. WO 2010/055666: Transformant No. 59),
a combination of Leu6Thr, Met271Ile, Thr36Met, and Phe126Tyr in the α subunit, and Thr10Asp, Pro107Met, Phe118Val, and Ala200Glu in the β subunit (International Publication No. WO 2010/055666: Transformant No. 68),
a combination of Leu6Thr, Thr36Met, and Phe126Tyr in the α subunit, and Thr10Asp, Phe118Val, Ala200Glu, Pro206Leu, and Ala230Glu in the β subunit (International Publication No. WO 2010/055666: Transformant No. 92),
a combination of Leu6Thr, Ala19Val, and Phe126Tyr in the α subunit, and Leu48Val, His79Asn, Glu108Arg, Ser212Tyr, and Ala230Glu in the β subunit (International Publication No. WO 2010/055666: Transformant No. 85), and
a combination of Thr36Met, Gly148Asp, and Val204Arg in the α subunit, and Phe41Ile, Phe51Val, Glu108Asp, Pro206Leu, and Ala230Glu in the β subunit (International Publication No. WO 2010/055666: Transformant No. 93), and the like.

In addition, the amino acid sequence of the modified nitrile hydratase that can be used as introduction targets for one or more among the amino acid residue substitutions (a) to (e) may include an amino acid residue substitution at an amino acid residue other than sites exemplified above (amino acid residue substitution group B and amino acid residue substitution (f)) compared to the amino acid sequence of the wild-type *Pseudonocardia thermophila*-derived nitrile hydratase. In the modified nitrile hydratase including the amino acid residue substitution at the amino acid residue other than the amino acid residue substitution group B and amino acid residue substitution (f), in addition to one or more amino acid residue substitutions in the amino acid residue substitution group B and/or the amino acid residue substitution (f) or without the amino acid residue substitution of the amino acid residue substitution group B and the amino acid residue substitution (f), the introduction of one or more of the amino acid residue substitutions (a) to (e) exhibits an effect of improving pH stability possessed by the modified nitrile hydratase through stabilization of the three-dimensional structure as described below.

One or more of amino acid residue substitutions (a) to (e) may be introduced into the wild-type *Pseudonocardia thermophila*-derived nitrile hydratase or the modified nitrile hydratase to obtain a mutant nitrile hydratase according to the disclosure.

The mutated nitrile hydratase may include a combination of two amino acid residue substitutions shown in Table 1 among the amino acid residue substitutions (a) to (e) and (f).

TABLE I

| No. | Mutation Site | Before Mutation | After Mutation |
|---|---|---|---|
| a | α36 | Thr | Trp |
|   | α40 | Asp | Asn |
| b | α36 | Thr | Trp |
|   | α43 | Ala | Val |
| c | α36 | Thr | Trp |
|   | β205 | Gly | Val |
| d | α36 | Thr | Trp |
|   | β206 | Pro | Gln |
| e | α36 | Thr | Trp |
|   | β215 | Tyr | Asn |
| f | α40 | Asp | Asn |
|   | α43 | Ala | Val |

TABLE I-continued

| No. | Mutation Site | Before Mutation | After Mutation |
|---|---|---|---|
| g | α40 | Asp | Asn |
|   | β205 | Gly | Val |
| h | α40 | Asp | Asn |
|   | β206 | Pro | Gln |
| i | α40 | Asp | Asn |
|   | β215 | Tyr | Asn |
| j | α43 | Ala | Val |
|   | β205 | Gly | Val |
| k | α43 | Ala | Val |
|   | β206 | Pro | Gln |
| l | α43 | Ala | Val |
|   | β215 | Tyr | Asn |
| m | β205 | Gly | Val |
|   | β206 | Pro | Gln |
| n | β205 | Gly | Val |
|   | β215 | Tyr | Asn |
| o | β206 | Pro | Gln |
|   | β215 | Tyr | Asn |

The mutated nitrile hydratase may include a combination of three amino acid residue substitutions shown in Table II among the amino acid residue substitutions (a) to (e) and (f).

TABLE II

| No. | Mutation Site | Before Mutation | After Mutation |
|---|---|---|---|
| p | α36 | Thr | Trp |
|   | α40 | Asp | Asn |
|   | α43 | Ala | Val |
| q | α36 | Thr | Trp |
|   | α40 | Asp | Asn |
|   | β205 | Gly | Val |
| r | α36 | Thr | Trp |
|   | α40 | Asp | Asn |
|   | β206 | Pro | Gln |
| s | α36 | Thr | Trp |
|   | α40 | Asp | Asn |
|   | β215 | Tyr | Asn |
| t | α36 | Thr | Trp |
|   | α43 | Ala | Val |
|   | β205 | Gly | Val |
| u | α36 | Thr | Trp |
|   | α43 | Ala | Val |
|   | β206 | Pro | Gln |
| v | α36 | Thr | Trp |
|   | α43 | Ala | Val |
|   | β215 | Tyr | Asn |
| w | α36 | Thr | Trp |
|   | β205 | Gly | Val |
|   | β206 | Pro | Gln |
| x | α36 | Thr | Trp |
|   | β205 | Gly | Val |
|   | β215 | Tyr | Asn |
| y | α36 | Thr | Trp |
|   | β206 | Pro | Gln |
|   | β215 | Tyr | Asn |
| z | α40 | Asp | Asn |
|   | α43 | Ala | Val |
|   | β205 | Gly | Val |
| aa | α40 | Asp | Asn |
|   | α43 | Ala | Val |
|   | β206 | Pro | Gln |
| ab | α40 | Asp | Asn |
|   | α43 | Ala | Val |
|   | β215 | Tyr | Asn |
| ac | α40 | Asp | Asn |
|   | β205 | Gly | Val |
|   | β206 | Pro | Gln |
| ad | α40 | Asp | Asn |
|   | β205 | Gly | Val |
|   | β215 | Tyr | Asn |
| ae | α40 | Asp | Asn |
|   | β206 | Pro | Gln |
|   | β215 | Tyr | Asn |

TABLE II-continued

| No. | Mutation Site | Before Mutation | After Mutation |
|---|---|---|---|
| af | α43 | Ala | Val |
|  | β205 | Gly | Val |
|  | β206 | Pro | Gln |
| ag | α43 | Ala | Val |
|  | β205 | Gly | Val |
|  | β215 | Tyr | Asn |
| ah | α43 | Ala | Val |
|  | β206 | Pro | Gln |
|  | β215 | Tyr | Asn |
| ai | β205 | Gly | Val |
|  | β206 | Pro | Gln |
|  | β215 | Tyr | Asn |

The mutated nitrile hydratase may include a combination of four amino acid residue substitutions shown in Table III among the amino acid residue substitutions (a) to (e) and (f).

TABLE III

| No. | Mutation Site | Before Mutation | After Mutation |
|---|---|---|---|
| aj | α36 | Thr | Trp |
|  | α40 | Asp | Asn |
|  | α43 | Ala | Val |
|  | β205 | Gly | Val |
| ak | α36 | Thr | Trp |
|  | α40 | Asp | Asn |
|  | α43 | Ala | Val |
|  | β206 | Pro | Gln |
| al | α36 | Thr | Trp |
|  | α40 | Asp | Asn |
|  | α43 | Ala | Val |
|  | β215 | Tyr | Asn |
| am | α36 | Thr | Trp |
|  | α40 | Asp | Asn |
|  | β205 | Gly | Val |
|  | β206 | Pro | Gln |
| an | α36 | Thr | Trp |
|  | α40 | Asp | Asn |
|  | β205 | Gly | Val |
|  | β215 | Tyr | Asn |
| ao | α36 | Thr | Trp |
|  | α40 | Asp | Asn |
|  | β206 | Pro | Gln |
|  | β215 | Tyr | Asn |
| ap | α36 | Thr | Trp |
|  | α43 | Ala | Val |
|  | β205 | Gly | Val |
|  | β206 | Pro | Gln |
| aq | α36 | Thr | Trp |
|  | α43 | Ala | Val |
|  | β205 | Gly | Val |
|  | β215 | Tyr | Asn |
| ar | α36 | Thr | Trp |
|  | α43 | Ala | Val |
|  | β206 | Pro | Gln |
|  | β215 | Tyr | Asn |
| as | α36 | Thr | Trp |
|  | β205 | Gly | Val |
|  | β206 | Pro | Gln |
|  | β215 | Tyr | Asn |
| at | α40 | Asp | Asn |
|  | α43 | Ala | Val |
|  | β205 | Gly | Val |
|  | β206 | Pro | Gln |
| au | α40 | Asp | Asn |
|  | α43 | Ala | Val |
|  | β205 | Gly | Val |
|  | β215 | Tyr | Asn |
| av | α40 | Asp | Asn |
|  | α43 | Ala | Val |
|  | β206 | Pro | Gln |
|  | β215 | Tyr | Asn |
| aw | α40 | Asp | Asn |
|  | β205 | Gly | Val |

TABLE III-continued

| No. | Mutation Site | Before Mutation | After Mutation |
|---|---|---|---|
|  | β206 | Pro | Gln |
|  | β215 | Tyr | Asn |
| ax | α43 | Ala | Val |
|  | β205 | Gly | Val |
|  | β206 | Pro | Gln |
|  | β215 | Tyr | Asn |

The mutated nitrile hydratase may include a combination of five amino acid residue substitutions shown in Table IV among the amino acid residue substitutions (a) to (e) and (f).

TABLE IV

| No. | Mutation Site | Before Mutation | After Mutation |
|---|---|---|---|
| ay | α36 | Thr | Trp |
|  | α40 | Asp | Asn |
|  | α43 | Ala | Val |
|  | β205 | Gly | Val |
|  | β206 | Pro | Gln |
| az | α36 | Thr | Trp |
|  | α40 | Asp | Asn |
|  | α43 | Ala | Val |
|  | β205 | Gly | Val |
|  | β215 | Tyr | Asn |
| ba | α36 | Thr | Trp |
|  | α40 | Asp | Asn |
|  | α43 | Ala | Val |
|  | β206 | Pro | Gln |
|  | β215 | Tyr | Asn |
| bb | α36 | Thr | Trp |
|  | α40 | Asp | Asn |
|  | β205 | Gly | Val |
|  | β206 | Pro | Gln |
|  | β215 | Tyr | Asn |
| bc | α36 | Thr | Trp |
|  | α43 | Ala | Val |
|  | β205 | Gly | Val |
|  | β206 | Pro | Gln |
|  | β215 | Tyr | Asn |
| bd | α40 | Asp | Asn |
|  | α43 | Ala | Val |
|  | β205 | Gly | Val |
|  | β206 | Pro | Gln |
|  | β215 | Tyr | Asn |

The mutated nitrile hydratase may include a combination of all of amino acid residue substitutions (a) to (e) and (f) (six amino acid residue substitutions shown in Table V).

TABLE V

| No. | Mutation Site | Before Mutation | After Mutation |
|---|---|---|---|
| be | α36 | Thr | Trp |
|  | α40 | Asp | Asn |
|  | α43 | Ala | Val |
|  | β205 | Gly | Val |
|  | β206 | Pro | Gln |
|  | β215 | Tyr | Asn |

The amino acid sequence of the modified nitrile hydratase that can be used as introduction targets for one or more among the amino acid residue substitutions (a) to (e) may be an amino acid sequence of the modified nitrile hydratase produced in WO 2010/055666, and the like, or a sequence similar thereto. Therefore, the mutant nitrile hydratase according to the disclosure may be obtained, for example, by introducing at least one of:

a substitution of the 40th amino acid residue from the N terminal of the α subunit with Asn.

a substitution of the 43rd amino acid residue from the N terminal of the α subunit with Val, a substitution of the 205th amino acid residue from the N terminal of the β subunit with Val,
a substitution of the 206th amino acid residue from the N terminal of the β subunit with Gln, and
a substitution of the 215th amino acid residue from the N terminal of the β subunit with Asn, into any one of the following nitrile hydratases (1) to (47) (hereinafter also referred to as "mutant nitrile hydratase B"):

(1) a nitrile hydratase that has an α subunit having the amino acid sequence of SEQ ID NO: 1: and a β subunit having an amino acid sequence of SEQ ID NO: 2, (2) a nitrile hydratase that has an α subunit having the amino acid sequence of SEQ ID NO: 16; and a β subunit having an amino acid sequence of SEQ ID NO: 33, (3) a nitrile hydratase that has an α subunit having the amino acid sequence of SEQ ID NO: 17; and a β subunit having an amino acid sequence of SEQ ID NO: 33, (4) a nitrile hydratase that has an α subunit having the amino acid sequence of SEQ ID NO: 18; and a β subunit having an amino acid sequence of SEQ ID NO: 34, (5) a nitrile hydratase that has an α subunit having the amino acid sequence of SEQ ID NO: 19; and a β subunit having an amino acid sequence of SEQ ID NO: 34, (6) a nitrile hydratase that has an α subunit having the amino acid sequence of SEQ ID NO: 20; and a β subunit having an amino acid sequence of SEQ ID NO: 35, (7) a nitrile hydratase that has an α subunit having the amino acid sequence of SEQ ID NO: 20; and a β subunit having an amino acid sequence of SEQ ID NO: 36.

(8) a nitrile hydratase that has an α subunit having the amino acid sequence of SEQ ID NO: 21; and a β subunit having an amino acid sequence of SEQ ID NO: 37, (9) a nitrile hydratase that has an α subunit having the amino acid sequence of SEQ ID NO: 21; and a β subunit having an amino acid sequence of SEQ ID NO: 38,

(10) a nitrile hydratase that has an α subunit having the amino acid sequence of SEQ ID NO: 21; and a β subunit having an amino acid sequence of SEQ ID NO: 39,

(11) a nitrile hydratase that has an α subunit having the amino acid sequence of SEQ ID NO: 21; and a β subunit having an amino acid sequence of SEQ ID NO: 40,

(12) a nitrile hydratase that has an α subunit having the amino acid sequence of SEQ ID NO: 18; and a β subunit having an amino acid sequence of SEQ ID NO: 41,

(13) a nitrile hydratase that has an α subunit having the amino acid sequence of SEQ ID NO: 18; and a β subunit having an amino acid sequence of SEQ ID NO: 42,

(14) a nitrile hydratase that has an α subunit having the amino acid sequence of SEQ ID NO: 21; and a β subunit having an amino acid sequence of SEQ ID NO: 43.

(15) a nitrile hydratase that has an α subunit having the amino acid sequence of SEQ ID NO: 22; and a β subunit having an amino acid sequence of SEQ ID NO: 44,

(16) a nitrile hydratase that has an α subunit having the amino acid sequence of SEQ ID NO: 23; and a β subunit having an amino acid sequence of SEQ ID NO: 45,

(17) a nitrile hydratase that has an α subunit having the amino acid sequence of SEQ ID NO: 24; and a β subunit having an amino acid sequence of SEQ ID NO: 46,

(18) a nitrile hydratase that has an α subunit having the amino acid sequence of SEQ ID NO: 25; and a β subunit having an amino acid sequence of SEQ ID NO: 47,

(19) a nitrile hydratase that has an α subunit having the amino acid sequence of SEQ ID NO: 18; and a β subunit having an amino acid sequence of SEQ ID NO: 48,

(20) a nitrile hydratase that has an α subunit having the amino acid sequence of SEQ ID NO: 23; and a β subunit having an amino acid sequence of SEQ ID NO: 49,

(21) a nitrile hydratase that has an α subunit having the amino acid sequence of SEQ ID NO: 16; and a β subunit having an amino acid sequence of SEQ ID NO: 50.

(22) a nitrile hydratase that has an α subunit having the amino acid sequence of SEQ ID NO: 26; and a β subunit having an amino acid sequence of SEQ ID NO: 51,

(23) a nitrile hydratase that has an α subunit having the amino acid sequence of SEQ ID NO: 27; and a β subunit having an amino acid sequence of SEQ ID NO: 52,

(24) a nitrile hydratase that has an α subunit having the amino acid sequence of SEQ ID NO: 28; and a β subunit having an amino acid sequence of SEQ ID NO: 53,

(25) a nitrile hydratase that has an α subunit having the amino acid sequence of SEQ ID NO: 17; and a β subunit having an amino acid sequence of SEQ ID NO: 54,

(26) a nitrile hydratase that has an α subunit having the amino acid sequence of SEQ ID NO: 29; and a β subunit having an amino acid sequence of SEQ ID NO: 55,

(27) a nitrile hydratase that has an α subunit having the amino acid sequence of SEQ ID NO: 18; and a β subunit having an amino acid sequence of SEQ ID NO: 56,

(28) a nitrile hydratase that has an α subunit having the amino acid sequence of SEQ ID NO: 18; and a β subunit having an amino acid sequence of SEQ ID NO: 57.

(29) a nitrile hydratase that has an α subunit having the amino acid sequence of SEQ ID NO: 30; and a β subunit having an amino acid sequence of SEQ ID NO: 58,

(30) a nitrile hydratase that has an α subunit having the amino acid sequence of SEQ ID NO: 29; and a β subunit having an amino acid sequence of SEQ ID NO: 59,

(31) a nitrile hydratase that has an α subunit having the amino acid sequence of SEQ ID NO: 31; and a β subunit having an amino acid sequence of SEQ ID NO: 60,

(32) a nitrile hydratase that has an α subunit having the amino acid sequence of SEQ ID NO: 18; and a β subunit having an amino acid sequence of SEQ ID NO: 61,

(33) a nitrile hydratase that has an α subunit having the amino acid sequence of SEQ ID NO: 32; and a β subunit having an amino acid sequence of SEQ ID NO: 62,

(34) a nitrile hydratase that has an α subunit having the amino acid sequence of SEQ ID NO: 30; and a β subunit having an amino acid sequence of SEQ ID NO: 63,

(35) a nitrile hydratase that has an α subunit having the amino acid sequence of SEQ ID NO: 30; and a β subunit having an amino acid sequence of SEQ ID NO: 64.

(36) a nitrile hydratase that has an α subunit having the amino acid sequence of SEQ ID NO: 30; and a β subunit having an amino acid sequence of SEQ ID NO: 65,

(37) a nitrile hydratase that has an α subunit having the amino acid sequence of SEQ ID NO: 25; and a β subunit having an amino acid sequence of SEQ ID NO: 54,

(38) a nitrile hydratase that has an α subunit having the amino acid sequence of SEQ ID NO: 30; and a β subunit having an amino acid sequence of SEQ ID NO: 66,

(39) a nitrile hydratase that has an α subunit having the amino acid sequence of SEQ ID NO: 1; and a β subunit having an amino acid sequence of SEQ ID NO: 67,

(40) a nitrile hydratase that has an α subunit having the amino acid sequence of SEQ ID NO: 1; and a β subunit having an amino acid sequence of SEQ ID NO: 68,

(41) a nitrile hydratase that has an α subunit having the amino acid sequence of SEQ ID NO: 1; and a β subunit having an amino acid sequence of SEQ ID NO: 69,

(42) a nitrile hydratase that has an α subunit having the amino acid sequence of SEQ ID NO: 1; and a β subunit having an amino acid sequence of SEQ ID NO: 70.

(43) a nitrile hydratase that has an α subunit having the amino acid sequence of SEQ ID NO: 1; and a β subunit having an amino acid sequence of SEQ ID NO: 71,

(44) a nitrile hydratase that has an α subunit having the amino acid sequence of SEQ ID NO: 21; and a β subunit having an amino acid sequence of SEQ ID NO: 72,

(45) a nitrile hydratase that has an α subunit having the amino acid sequence of SEQ ID NO: 1; and a β subunit having an amino acid sequence of SEQ ID NO: 73,

(46) a nitrile hydratase in which the 36th amino acid residue from the N terminal of the α subunit in any one of the nitrile hydratases (1) to (45) is a Trp residue,

(47) a modified nitrile hydratase that has an α subunit variant consisting of amino acid sequences of an α subunit of the specific nitrile hydratase which is any one of the nitrile hydratases (1) to (46) or amino acid sequences having 70% or more sequence identity with the amino acid sequences; and a β subunit variant consisting of amino acid sequences of a β subunit of the specific nitrile hydratase or amino acid sequences having 70% or more sequence identity with the amino acid sequences, in which at least one of the amino acid sequences of the α subunit and the amino acid sequences of the β subunit is the amino acid sequence of the α subunit variant or the β subunit variant.

In addition, the nitrile hydratase (2) to (45) is different from the nitrile hydratase (1) that has an α subunit having an amino acid sequence of SEQ ID NO: 1 and a β subunit having an amino acid sequence of SEQ ID NO: 2 in view of the amino acid residues described in the following Tables 6 to 13, and is described together with the transformant number in WO 2010/055666. In Tables below, the number in the column of mutation site indicates the position from the N terminal of the amino acid sequence of the subunit. In addition, the transformant number is the number attached in International Publication No. WO 2010/055666.

TABLE 6

| Nitrile Hydratase | Transformant No. | Mutation Site | Difference In Amino Acid Sequence | | SEQ ID NO. |
|---|---|---|---|---|---|
| | | | Nitrile Hydratase (1) | Corresponding Nitrile Hydratase | |
| (2) | 2 | α36th | Thr | Met | 16 |
| | | α148th | Gly | Asp | |
| | | α204th | Val | Arg | |
| | | β41st | Phe | Ile | 33 |
| | | β51st | Phe | Val | |
| | | β108th | Glu | Asp | |
| (3) | 5 | α36th | Thr | Met | 17 |
| | | α92nd | Asp | Glu | |
| | | α148th | Gly | Asp | |
| | | α204th | Val | Arg | |
| | | β41st | Phe | Ile | 33 |
| | | β51st | Phe | Val | |
| | | β108th | Glu | Asp | |
| (4) | 9 | α6th | Leu | Thr | 18 |
| | | α19th | Ala | Val | |
| | | α126th | Phe | Tyr | |
| | | β46th | Met | Lys | 34 |
| | | β108th | Glu | Arg | |
| | | β212th | Ser | Tyr | |
| (5) | 12 | α6th | Leu | Thr | 19 |
| | | α19th | Ala | Val | |
| | | α94th | Met | Ile | |
| | | α126th | Phe | Tyr | |
| | | β46th | Met | Lys | 34 |

TABLE 6-continued

| Nitrile Hydratase | Transformant No. | Mutation Site | Difference In Amino Acid Sequence | | SEQ ID NO. |
|---|---|---|---|---|---|
| | | | Nitrile Hydratase (1) | Corresponding Nitrile Hydratase | |
| | | β108th | Glu | Arg | |
| | | β212th | Ser | Tyr | |
| (6) | 20 | α6th | Leu | Ala | 20 |
| | | α19th | Ala | Val | |
| | | α126th | Phe | Tyr | |
| | | β127th | Leu | Ser | 35 |
| | | β160th | Arg | Trp | |
| | | β186th | Leu | Arg | |

TABLE 7

| Nitrile Hydratase | Transformant No. | Mutation Site | Difference In Amino Acid Sequence | | SEQ ID NO. |
|---|---|---|---|---|---|
| | | | Nitrile Hydratase (1) | Corresponding Nitrile Hydratase | |
| (7) | 23 | α6th | Leu | Ala | 20 |
| | | α19th | Ala | Val | |
| | | α126th | Phe | Tyr | |
| | | β4th | Val | Met | 36 |
| | | β27th | Leu | Ser | |
| | | β160th | Arg | Trp | |
| | | β186th | Leu | Arg | |
| (8) | 27 | α19th | Ala | Val | 21 |
| | | α71st | Arg | His | |
| | | α126th | Phe | Tyr | |
| | | β37th | Phe | Leu | 37 |
| | | β108th | Glu | Asp | |
| | | β200th | Ala | Glu | |
| (9) | 29 | α19th | Ala | Val | 21 |
| | | α71st | Arg | His | |
| | | α126th | Phe | Tyr | |
| | | β8th | Gly | Ala | 38 |
| | | β37th | Phe | Leu | |
| | | β108th | Glu | Asp | |
| | | β200th | Ala | Glu | |
| (10) | 31 | α19th | Ala | Val | 21 |
| | | α71st | Arg | His | |
| | | α126th | Phe | Tyr | |
| | | β37th | Phe | Val | 39 |
| | | β108th | Glu | Asp | |
| | | β200th | Ala | Glu | |
| (11) | 33 | α19th | Ala | Val | 21 |
| | | α71st | Arg | His | |
| | | α126th | Phe | Tyr | |
| | | β37th | Phe | Val | 40 |
| | | β79th | His | Asn | |
| | | β108th | Glu | Asp | |
| | | β200th | Ala | Glu | |
| (12) | 38 | α6th | Leu | Thr | 18 |
| | | α19th | Ala | Val | |
| | | α126th | Phe | Tyr | |
| | | β48th | Leu | Val | 41 |
| | | β108th | Glu | Arg | |
| | | β212th | Ser | Tyr | |

TABLE 8

| Nitrile Hydratase | Transformant No. | Mutation Site | Difference In Amino Acid Sequence Nitrile Hydratase (1) | Difference In Amino Acid Sequence Corresponding Nitrile Hydratase | SEQ ID NO. |
|---|---|---|---|---|---|
| (13) | 41 | α6th | Leu | Thr | 18 |
|  |  | α19th | Ala | Val |  |
|  |  | α126th | Phe | Tyr |  |
|  |  | β48th | Leu | Val | 42 |
|  |  | β96th | Gln | Arg |  |
|  |  | β108th | Glu | Arg |  |
|  |  | β212th | Ser | Tyr |  |
| (14) | 45 | α19th | Ala | Val | 21 |
|  |  | α71st | Arg | His |  |
|  |  | α126th | Phe | Tyr |  |
|  |  | β37th | Phe | Val | 43 |
|  |  | β107th | Pro | Met |  |
|  |  | β108th | Glu | Asp |  |
|  |  | β200th | Ala | Glu |  |
| (15) | 59 | α13th | Ile | Leu | 22 |
|  |  | α19th | Ala | Val |  |
|  |  | α71st | Arg | His |  |
|  |  | α126th | Phe | Tyr |  |
|  |  | β37th | Phe | Leu | 44 |
|  |  | α96th | Gln | Arg |  |
|  |  | β108th | Glu | Asp |  |
|  |  | β200th | Ala | Glu |  |
| (16) | 65 | α6th | Leu | Thr | 23 |
|  |  | α36th | Thr | Met |  |
|  |  | α126th | Phe | Tyr |  |
|  |  | β10th | Thr | Asp | 45 |
|  |  | β118th | Phe | Val |  |
|  |  | β200th | Ala | Glu |  |
| (17) | 68 | α6th | Leu | Thr | 24 |
|  |  | α27th | Met | Ile |  |
|  |  | α36th | Thr | Met |  |
|  |  | α126th | Phe | Tyr |  |
|  |  | β10th | Thr | Asp | 46 |
|  |  | β107th | Pro | Met |  |
|  |  | β118th | Phe | Val |  |
|  |  | β200th | Ala | Glu |  |
| (18) | 74 | α92nd | Asp | Glu | 25 |
|  |  | α148th | Gly | Asp |  |
|  |  | α204th | Val | Arg |  |
|  |  | β108th | Glu | Asp | 47 |
|  |  | β200th | Ala | Glu |  |
|  |  | β226th | Val | Ile |  |

TABLE 9

| Nitrile Hydratase | Transformant No. | Mutation Site | Difference In amino acid sequence Nitrile Hydratase (1) | Difference In amino acid sequence Corresponding Nitrile Hydratase | SEQ ID NO. |
|---|---|---|---|---|---|
| (19) | 85 | α6th | Leu | Thr | 18 |
|  |  | α19th | Ala | Val |  |
|  |  | α126th | Phe | Tyr |  |
|  |  | β48th | Leu | Val | 48 |
|  |  | β79th | His | Asn |  |
|  |  | β108th | Glu | Arg |  |
|  |  | β212th | Ser | Tyr |  |
|  |  | β230th | Ala | Glu |  |
| (20) | 92 | α6th | Leu | Thr | 23 |
|  |  | α36th | Thr | Met |  |
|  |  | α126th | Phe | Tyr |  |
|  |  | β10th | Thr | Asp | 49 |
|  |  | β118th | Phe | Val |  |
|  |  | β200th | Ala | Glu |  |
|  |  | β206th | Pro | Leu |  |
|  |  | β230th | Ala | Glu |  |
| (21) | 93 | α36th | Thr | Met | 16 |
|  |  | α148th | Gly | Asp |  |
|  |  | α204th | Val | Arg |  |
|  |  | β41st | Phe | Ile | 50 |
|  |  | β51st | Phe | Val |  |
|  |  | β108th | Glu | Asp |  |
|  |  | β206th | Pro | Leu |  |
|  |  | β230th | Ala | Glu |  |
| (22) | 95 | α13th | Ile | Leu | 26 |
|  |  | α19th | Ala | Val |  |
|  |  | α27th | Met | Ile |  |
|  |  | α71st | Arg | His |  |
|  |  | α126th | Phe | Tyr |  |
|  |  | β110th | Glu | Asn | 51 |
| (23) | 96 | α13th | Ile | Leu | 27 |
|  |  | α27th | Met | Ile |  |
|  |  | β46th | Met | Lys | 52 |
|  |  | β108th | Glu | Arg |  |
|  |  | β110th | Glu | Asn |  |
|  |  | β212th | Ser | Tyr |  |
| (24) | 100 | α13th | Ile | Leu | 28 |
|  |  | β10th | Thr | Asp | 53 |
|  |  | β118th | Phe | Val |  |
|  |  | β200th | Ala | Glu |  |
|  |  | β206th | Pro | Leu |  |
|  |  | β226th | Val | Ile |  |

TABLE 10

| Nitrile Hydratase | Transformant No. | Mutation Site | Difference In Amino Acid Sequence Nitrile Hydratase (1) | Difference In Amino Acid Sequence Corresponding Nitrile Hydratase | SEQ ID NO. |
|---|---|---|---|---|---|
| (25) | 104 | α36th | Thr | Met | 17 |
|  |  | α92nd | Asp | Glu |  |
|  |  | α148th | Gly | Asp |  |
|  |  | α204th | Val | Arg |  |
|  |  | β4th | Val | Met | 54 |
|  |  | β206th | Pro | Leu |  |
| (26) | 108 | α197th | Gly | Cys | 29 |
|  |  | β41st | Phe | Ile | 55 |
|  |  | β51st | Phe | Val |  |
|  |  | β107th | Pro | Met |  |
|  |  | β108th | Glu | Asp |  |
|  |  | β230th | Ala | Glu |  |
| (27) | 111 | α6th | Leu | Thr | 18 |
|  |  | α19th | Ala | Val |  |
|  |  | α126th | Phe | Tyr |  |
|  |  | β48th | Leu | Val | 56 |
|  |  | β79th | His | Asn |  |
|  |  | β108th | Glu | Arg |  |
|  |  | β212th | Ser | Tyr |  |
|  |  | β230th | Ala | Glu |  |
|  |  | β231st | Ala | Val |  |
| (28) | 112 | α6th | Leu | Thr | 18 |
|  |  | α19th | Ala | Val |  |
|  |  | α126th | Phe | Tyr |  |
|  |  | β46th | Met | Lys | 57 |
|  |  | β79th | His | Asn |  |
|  |  | β108th | Glu | Arg |  |
|  |  | β212th | Ser | Tyr |  |
|  |  | β230th | Ala | Glu |  |
|  |  | β231st | Ala | Val |  |
| (29) | 114 | α92nd | Asp | Glu | 30 |
|  |  | β24th | Val | Ile | 58 |
|  |  | β41st | Phe | Ile |  |
|  |  | β51st | Phe | Val |  |

TABLE 10-continued

| Nitrile Hydratase | Transformant No. | Mutation Site | Nitrile Hydratase (1) | Corresponding Nitrile Hydratase | SEQ ID NO. |
|---|---|---|---|---|---|
| | | β108th | Glu | Asp | |
| | | β226th | Val | Ile | |

TABLE 11

| Nitrile Hydratase | Transformant No. | Mutation Site | Nitrile Hydratase (1) | Corresponding Nitrile Hydratase | SEQ ID NO. |
|---|---|---|---|---|---|
| (30) | 115 | α197th | Gly | Cys | 29 |
| | | β24th | Val | Ile | 59 |
| | | β41st | Phe | Ile | |
| | | β51st | Phe | Val | |
| | | β107th | Pro | Met | |
| | | β108th | Glu | Asp | |
| | | β230th | Ala | Glu | |
| (31) | 116 | α48th | Asn | Glu | 31 |
| | | α197th | Gly | Cys | |
| | | β24th | Val | Ile | 60 |
| | | β107th | Pro | Met | |
| | | β146th | Arg | Gly | |
| | | β230th | Ala | Glu | |
| (32) | 117 | α6th | Leu | Thr | 18 |
| | | α19th | Ala | Val | |
| | | α126th | Phe | Tyr | |
| | | β24th | Val | Ile | 61 |
| | | β48th | Leu | Val | |
| | | β79th | His | Asn | |
| | | β108th | Glu | Arg | |
| | | β212th | Ser | Tyr | |
| | | β230th | Ala | Glu | |
| | | β231st | Ala | Val | |

TABLE 12

| Nitrile Hydratase | Transformant No. | Mutation Site | Nitrile Hydratase (1) | Corresponding Nitrile Hydratase | SEQ ID NO. |
|---|---|---|---|---|---|
| (33) | 6 | α36th | Thr | Ser | 32 |
| | | α92nd | Asp | Glu | |
| | | β33rd | Ala | Val | 62 |
| (34) | 7 | α92nd | Asp | Glu | 30 |
| | | β40th | Thr | Ile | 63 |
| | | β61st | Ala | Val | |
| (35) | 73 | α92nd | Asp | Glu | 30 |
| | | β41st | Phe | Ile | 64 |
| | | β51st | Phe | Val | |
| | | β108th | Glu | Asp | |
| | | β226th | Val | Ile | |
| (36) | 75 | α92nd | Asp | Glu | 30 |
| | | β61st | Ala | Leu | 65 |
| | | β112th | Lys | Ile | |
| | | β226th | Val | Ile | |
| (37) | 103 | α92nd | Asp | Glu | 25 |
| | | α148th | Gly | Asp | |
| | | α204th | Val | Arg | |
| | | β4th | Val | Met | 54 |
| | | β206th | Pro | Leu | |
| (38) | 105 | α92nd | Asp | Glu | 30 |
| | | β4th | Val | Met | 66 |
| | | β51st | Phe | Val | |

TABLE 12-continued

| Nitrile Hydratase | Transformant No. | Mutation Site | Nitrile Hydratase (1) | Corresponding Nitrile Hydratase | SEQ ID NO. |
|---|---|---|---|---|---|
| | | β108th | Glu | Asp | |
| | | β206th | Pro | Leu | |
| (39) | 34 | β33rd | Ala | Met | 67 |
| | | β79th | His | Asn | |
| | | β176th | Tyr | Thr | |

TABLE 13

| Nitrile Hydratase | Transformant No. | Mutation Site | Nitrile Hydratase (1) | Corresponding Nitrile Hydratase | SEQ ID NO. |
|---|---|---|---|---|---|
| (40) | 35 | β61st | Ala | Gly | 68 |
| | | β79th | His | Asn | |
| | | β150th | Ala | Asn | |
| (41) | 78 | β4th | Val | Met | 69 |
| | | β48th | Leu | Val | |
| | | β79th | His | Asn | |
| | | β108th | Glu | Arg | |
| | | β212th | Ser | Tyr | |
| (42) | 79 | β4th | Val | Met | 70 |
| | | β61st | Ala | Thr | |
| | | β79th | His | Asn | |
| | | β218th | Cys | Ser | |
| (43) | 80 | β4th | Val | Met | 71 |
| | | β79th | His | Asn | |
| | | β146th | Arg | Gly | |
| | | β217th | Asp | Ser | |
| (44) | 83 | α19th | Ala | Val | 21 |
| | | α71st | Arg | His | |
| | | α126th | Phe | Tyr | |
| | | β79th | His | Asn | 72 |
| | | β230th | Ala | Glu | |
| (45) | 84 | β10th | Thr | Asp | 73 |
| | | β79th | His | Asn | |
| | | β118th | Phe | Val | |
| | | β200th | Ala | Glu | |
| | | β230th | Ala | Glu | |

The amino acid sequence of the modified nitrile hydratase that can be used as introduction targets for one or more among the amino acid residue substitutions (a) to (e) is preferably an amino acid sequence of any one of 44 nitrile hydratases of (2) to (45) described above, and more preferably, an amino acid sequence of any one of the nitrile hydratases (3), (11), (18), (19), (25), (27), (28), (29), (32), (33), (34), (35), (36), (37), (38), (39), (40), (41), (42), (43), (44), and (45).

In (47), the sequence identity of the amino acid sequence of the α subunit variant to the α subunit of the specific nitrile hydratase may be 80% or more, 85% or more, 90% or more, 95% or more, 96% or more, 97% or more, 980/or more, or 99% or more. Similarly, in the above (47), the sequence identity of the amino acid sequence of the β subunit variant to the β subunit of the specific nitrile hydratase may be 80% or more, 85% or more, 90% or more, 95% or more, 96% or more, 97% or more, 98% or more, or 99% or more. In addition, the α subunit variant refers to an α subunit which satisfies the sequence identity defined above and has an amino acid sequence different from the α subunit of the specific nitrile hydratase. The β subunit variant refers to a β subunit which satisfies the sequence identity defined above and has an amino acid sequence different from the β subunit of the specific nitrile hydratase.

The nitrile hydratases of the above (2) to (45) are nitrile hydratases of which an activity is confirmed in Examples in International Publication No. WO 2010/055666 (transformant Nos. 5, 62, 68, 95, and 111), and in addition, the nitrile hydratase of the above (1) is a wild-type *Pseudonocardia thermophila*-derived nitrile hydratase. The nitrile hydratases of (2) to (46) can also be used as introduction targets for one or more among the amino acid residue substitutions (a) to (e). Further, other modified nitrile hydratase having an amino acid sequence similar to the amino acid sequence of this nitrile hydratase can also be used as introduction targets for one or more among the amino acid residue substitutions (a) to (e). Therefore, in the description regarding a difference in amino acid sequence between the modified nitrile hydratase and the wild-type *Pseudonocardia thermophila*-derived nitrile hydratase (including the description of the degree of sequence modification and examples), the "wild-type *Pseudonocardia thermophila*-derived nitrile hydratase" can be substituted with any one of the above nitrile hydratases (1) to (46) and can be applied as it is. In addition, the modified nitrile hydratase should have a nitrile hydratase activity.

For example, with respect to amino acid residue substitutions and combinations thereof that can be included in the mutant nitrile hydratase B, and the 36th amino acid residue from the N terminal of the α subunit of the nitrile hydratase, the mutant nitrile hydratase B may include a combination of amino acid residues selected from the group consisting of combinations a to o of the amino acid residues listed in Table I above, combinations p to ai of the amino acid residues listed in Table II above, combinations aj to ax of the amino acid residues described in Table III above, combinations ay to bd of the amino acid residues described in Table IV above, and a combination be of the amino acid residues described in Table V above. In other words, the combination of the amino acid residue substitution can be introduced with respect to the amino acid sequence of the nitrile hydratases (1) to (46).

Further, for example, the nitrile hydratase (47) may be a modified nitrile hydratase in which one or more modifications have been made with respect to any one of the nitrile hydratases (1) to (46), the modification being selected from the group consisting of (i) substitution of one or more amino acid residues with other amino acid residue, (ii) deletion of one or more amino acid residues other than (a) to (e), (iii) insertion of amino acid residues, (iv) addition of an amino acid residue to one or both of the N terminal and C terminal of the amino acid sequence of the α subunit, and (v) addition of an amino acid residue to one or both of the N terminal and C terminal of the amino acid sequence of the β subunit.

In the α subunit of the nitrile hydratase (47), the number of amino acid residues substituted in a case of the α subunit of any one of the nitrile hydratases (1) to (46) as a reference is, for example, from 1 to 20, from 1 to 15, from 1 to 10, from 1 to 8, from 1 to 7, from 1 to 6, from 1 to 5, from 1 to 4, from 1 to 3, from 1 to 2, or 1. The number of substituted amino acid residues may be zero.

In the β subunit of the nitrile hydratase (47), the number of amino acid residues substituted in a case of the β subunit of any one of the nitrile hydratases (1) to (46) as a reference is, for example, from 1 to 20, from 1 to 15, from 1 to 10, from 1 to 8, from 1 to 7, from 1 to 6, from 1 to 5, from 1 to 4, from 1 to 3, from 1 to 2, or 1. The number of substituted amino acid residues may be zero.

In the α subunit of the nitrile hydratase (47), the number of amino acid residues deleted in a case of the α subunit of any one of the nitrile hydratases (1) to (46) as a reference is, for example, from 1 to 10, from 1 to 7, from 1 to 4, from 1 to 2, or 1. The number of deleted amino acid residues may be zero.

In the β subunit of the nitrile hydratase (47), the number of amino acid residues deleted in a case of the β subunit of any one of the nitrile hydratases (1) to (46) as a reference is, for example, from 1 to 10, from 1 to 7, from 1 to 4, from 1 to 2, or 1. The number of deleted amino acid residues may be zero.

In the α subunit of the nitrile hydratase (47), the number of amino acid residues inserted in a case of the α subunit of any one of the nitrile hydratases (1) to (46) as a reference is, for example, from 1 to 10, from 1 to 7, from 1 to 4, from 1 to 2, or 1. The number of inserted amino acid residues may be zero.

In the β subunit of the nitrile hydratase (47), the number of amino acid residues inserted in a case of the β subunit of any one of the nitrile hydratases (1) to (46) as a reference is, for example, from 1 to 10, from 1 to 7, from 1 to 4, from 1 to 2, or 1. The number of inserted amino acid residues may be zero.

In the α subunit of the nitrile hydratase (47), the total number of amino acid residues substituted, deleted, or inserted in a case of the α subunit of any one of the nitrile hydratases (1) to (46) as a reference is, for example, from 1 to 20, from 1 to 14, from 1 to 8, from 1 to 4, from 1 to 2, or 1. In a case in which there is a terminal-addition, and the like, the total number of substituted, deleted, or inserted amino acid residues may be zero.

In the β subunit of the modified nitrile hydratase (47), the total number of amino acid residues substituted, deleted or inserted in a case of the β subunit of any one of the nitrile hydratases (1) to (46) as a reference is, for example, from 1 to 20, from 1 to 14, from 1 to 8, from 1 to 4, from 1 to 2, or 1. In a case in which there is a terminal-addition, and the like, the total number of substituted, deleted, or inserted amino acid residues may be zero.

In the α subunit of the nitrile hydratase 47, the number of terminal-added amino acid residues in a case of the α subunit of any one of the nitrile hydratases (1) to (46) as a reference is, for example, from 1 to 60, from 1 to 40, from 1 to 20, from 1 to 10, from 1 to 5, from 1 to 3, or 1 per one terminal. The number of added amino acid residues may be zero.

In the β subunit of the nitrile hydratase (47), the number of terminal-added amino acid residues in a case of the β subunit of any one of the nitrile hydratases (1) to (46) as a reference is, for example, from 1 to 60, from 1 to 40, from 1 to 20, from 1 to 10, from 1 to 5, from 1 to 3, or 1 per one terminal. The number of added amino acid residues may be zero.

The nitrile hydratase (47) may include one or more amino acid residue substitutions selected from the amino acid residue substitution group B when compared with the amino acid sequence of any one of the nitrile hydratases (1) to (46). Two or more amino acid residue substitutions may be included in combination.

In the above description, the α/β subunit variant of the nitrile hydratase (47) does not have insertion of amino acids or deletion of amino acid residues and may have only substitution or terminal-addition of amino acid residue as compared with the amino acid sequence of the α/β subunit of the specific nitrile hydratase. A position of the amino acid residue in the α/β subunit variant of the nitrile hydratase (47)

means, as described above, a position corresponding to the designated amino acid residue in the α/β subunit of the specific nitrile hydratase on the alignment.

The mutant nitrile hydratase according to the disclosure may be obtained by introducing at least one of the following amino acid residue substitutions, with respect to the specific nitrile hydratase which is any one of the nitrile hydratases (1) to (46) or with respect to the modified nitrile hydratase that has a modified α subunit having 70% or more sequence identity with respect to the α subunit of the specific nitrile hydratase and a modified β subunit having 70% or more sequence identity with respect to the β subunit of the specific nitrile hydratase, but the nitrile hydratase is not the specific nitrile hydratase itself (hereinafter also referred to as "mutant nitrile hydratase C"):

a substitution with Asn, which is the amino acid residue corresponding to the 40th amino acid residue from the N terminal of the α subunit of the specific nitrile hydratase,
a substitution with Val, which is the amino acid residue corresponding to the 43th amino acid residue from the N terminal of the α subunit of the specific nitrile hydratase,
a substitution with Val, which is the amino acid residue corresponding to the 205th amino acid residue from the N terminal of the β subunit of the specific nitrile hydratase,
a substitution with Gin, which is the amino acid residue corresponding to the 206th amino acid residue from the N terminal of the β subunit of the specific nitrile hydratase, and
a substitution with Asn, which is the amino acid residue corresponding to the 215th amino acid residue from the N terminal of the β subunit of the specific nitrile hydratase.

In the above description, in a case in which the nitrile hydratase before introduction is the modified nitrile hydratase, "the amino acid residue corresponding to the Ath amino acid residue from the N terminal of the α subunit of the specific nitrile hydratase" refers to an amino acid residue on the amino acid sequence of the α subunit of the modified nitrile hydratase corresponding to the Ath amino acid residue from the N terminal of the amino acid sequence of the α subunit of the specific nitrile hydratase when the amino acid sequence of the α subunit of the modified nitrile hydratase is aligned with the amino acid sequence of the α subunit of the specific nitrile hydratase.

Similarly, "the amino acid residue corresponding to the Ath amino acid residue from the N terminal of the β subunit of the specific nitrile hydratase" refers to an amino acid residue on the amino acid sequence of the β subunit of the modified nitrile hydratase corresponding to the Ath amino acid residue from the N terminal of the amino acid sequence of the β subunit of the specific nitrile hydratase when the amino acid sequence of the β subunit of the modified nitrile hydratase is aligned with the amino acid sequence of the β subunit of the specific nitrile hydratase. Further, in a case in which the nitrile hydratase before introduction is a specific nitrile hydratase, the "amino acid residue corresponding to the Ath amino acid residue from the N terminal of the α subunit of the specific nitrile hydratase" refers to the Ath amino acid residue from the N terminal of the α subunit of the specific nitrile hydratase, and the "amino acid residue corresponding to the Ath amino acid residue from the N terminal of the β subunit of the specific nitrile hydratase" refers to the Ath amino acid residue from the N terminal of the β subunit of the specific nitrile hydratase.

In the modified nitrile hydratase, the sequence identity of the α subunit with respect to the α subunit of the specific nitrile hydratase may be 80% or more, 85% or more, 90% or more, 95% or more, 96% or more, 97% or more, 98% or more, or 996, or more. Similarly, the sequence identity of the β subunit with respect to the β subunit of the specific nitrile hydratase may be 80% or more, 85% or more, 90% or more, 95% or more, 96% or more, 97% or more, 98% or more, or 99% or more. In particular, in the modified nitrile hydratase, the sequence identity of the α subunit with respect to the α subunit of the specific nitrile hydratase is preferably 90% or more, and more preferably 95% or more. Similarly, in the modified nitrile hydratase, the sequence identity of the β subunit with respect to the β subunit of the specific nitrile hydratase is preferably 906 or more, and more preferably 95% or more. In the description regarding a difference in amino acid sequence between the modified nitrile hydratase and the wild-type *Pseudonocardia thermophila*-derived nitrile hydratase (including the description of the degree of sequence modification and examples), the "wild-type *Pseudonocardia thermophila*-derived nitrile hydratase" can be substituted with the specific nitrile hydratase and can be applied as it is. In the above description, the amino acid sequence of the α/β subunit of the modified nitrile hydratase does not have insertion of amino acids or deletion of amino acid residues and may have only substitution or terminal-addition of amino acid residue as compared with the amino acid sequence of the α/β subunit of the specific nitrile hydratase. In addition, the modified nitrile hydratase should have a nitrile hydratase activity.

With respect to amino acid residue substitutions and combinations thereof that can be included in the mutant nitrile hydratase C, and an amino acid residue corresponding to the 36th amino acid residue from the N terminal of the α subunit of the specific nitrile hydratase, the mutant nitrile hydratase C may include a combination of amino acid residues selected from the group consisting of combinations a to o of the amino acid residues listed in Table I above, combinations p to ai of the amino acid residues listed in Table II above, combinations aj to ax of the amino acid residues described in Table 111 above, combinations ay to bd of the amino acid residues described in Table IV above, and a combination be of the amino acid residues described in Table V above. In other words, the combination of the amino acid residue substitution can be introduced with respect to the amino acid sequence of the specific nitrile hydratase or the modified nitrile hydratase.

Further, for example, the modified nitrile hydratase may include one or more amino acid residue substitutions selected from the amino acid residue substitution group B when compared with the amino acid sequence of any one of the nitrile hydratases (1) to (46). Two or more amino acid residue substitutions may be included in combination.

The above-described modified nitrile hydratase may be a nitrile hydratase having a polypeptide in which an additional sequence is added to the specific α subunit or the N terminal or the C terminal or both thereof; and a polypeptide in which an additional sequence is added to the specific β subunit or the N terminal or the C terminal or both thereof. In the α subunit of the modified nitrile hydratase, the number of terminal-added amino acid residues is, for example, from 1 to 60, from 1 to 40, from 1 to 20, from 1 to 10, from 1 to 5, from 1 to 3, or 1 per one terminal. The number of added amino acid residues may be zero. In the α subunit of the modified nitrile hydratase, the number of terminal-added amino acid residues is, for example, from 1 to 60, from 1 to 40, from 1 to 20, from 1 to 10, from 1 to 5, from 1 to 3, or 1 per one terminal. The number of added amino acid residues may be zero.

In a case of including the amino acid sequence added, substituted, deleted, and/or inserted (excluding the amino acid residue to be substituted in the above (a) and (b)) in the α subunit of the modified nitrile hydratase, the total number of substituted, deleted, and/or inserted amino acid residues is preferably from 1 to 10, and more preferably from 1 to 5. Similarly, in a case of including the amino acid sequence added, substituted, deleted, and/or inserted in the α subunit of the modified nitrile hydratase (excluding the amino acid residue to be substituted in the above (c) to (e)) in the β subunit of the modified nitrile hydratase, the total number of substituted, deleted, and/or inserted amino acid residues is preferably from 1 to 10, and more preferably from 1 to 5.

The mutant nitrile hydratase according to the disclosure generally functions by associating two α subunits defined as described above and two β subunits defined as described above.

Unlike the conventional nitrile hydratase mutant, the mutant nitrile hydratase according to the disclosure exhibits excellent enzyme activity with respect to a synthesis reaction of an amide compound from the nitrile compound even under acidic conditions such as pH from 3.5 to 6.5, and the like. The improvement of the stability of the enzyme activity under the acidic conditions possessed by the mutant nitrile hydratase according to the disclosure is particularly remarkable in a region of pH 5.0 or less. Therefore, according to the mutant nitrile hydratase, it is possible to sufficiently perform a synthesis reaction of the amide compound in which a nitrile compound as a substrate is converted to the amide compound in a purification step in which impurities such as proteins present in the solution are adsorbed and removed by using activated carbon under acidic conditions such as pH from 3.5 to 6.5, and the like, thereby obtaining a purified amide compound as well as a reaction step of performing a reaction of synthesizing the amide compound from a nitrile compound in a production step of an industrial amide compound utilizing nitrile hydratase. Therefore, according to the mutant nitrile hydratase, when compared with a case of using a conventional enzyme, it is possible to dramatically improve a production efficiency of the amide compound which is a desired product, in the production step of the industrial amide compound. The acidic condition may be performed at a pH of 5.0 or less such as from pH 3.5 to pH 5.0 for more efficient removal of unnecessary proteins.

Further, a value of a ratio (initial reaction rate after acid treatment/initial reaction rate before acid treatment) of an initial reaction rate of mutant nitrile hydratase subjected to acid treatment (for example, treatment at pH 4.0 and 30° C. for 30 hours) to an initial reaction rate of mutant nitrile hydratase not subjected to the acid treatment is preferably of 1.1 times or more a value of a ratio (initial reaction rate after acid treatment/initial reaction rate before acid treatment) of an initial reaction rate of the wild-type *Pseudonocardia thermophila*-derived nitrile hydratase subjected to the acid treatment to an initial reaction rate of the wild-type *Pseudonocardia thermophila*-derived nitrile hydratase not subjected to the acid treatment. In addition, the pH stability of the above mutant nitrile hydratase or wild-type *Pseudonocardia thermophila*-derived nitrile hydratase can be, for example, evaluated by the following method. As reaction conditions, the reaction is performed at a reaction temperature of 20° C. for 15 minutes to 60 minutes using 50 mM tris-hydrochloric acid aqueous solution (pH 8.0) containing 2.5% (v/v) of acrylonitrile as the substrate. After the reaction is completed, the produced acrylamide is quantified. An amount of acrylamide can be analyzed by HPLC. Further, the acid treatment can be performed, for example, by treatment around pH 4.0 and 30° C. for 30 hours. Specifically, the pH stability can be evaluated in the manner described in the section of the pH stability evaluation in Examples.

For example, 40 μL of a culture completion solution of a transformant producing nitrile hydratase is suspended in 740 μL of 54 mM tris-hydrochloric acid aqueous solution (pH 8.0), 20 μL of acrylonitrile is added thereto, and the mixture is reacted for 15 to 60 minutes while gently stirring at 20° C. After the reaction is completed, analysis of the reaction solution is performed using HPLC to measure an amount (P) of the produced amide compound (or may be calculated from an amount of the nitrile compound consumed). In addition, 1000 μL of the culture completion solution of the transformant is taken and centrifuged to recover bacterial cells, 1000 μL of 50 mM citric acid buffer (pH 4.0) is added to the recovered bacterial cells, and the solution is treated at 30° C. for 30 hours (acid treatment) with stirring. After treatment, 780 μL of the mixture is centrifuged to recover bacterial cells, the bacterial cells are suspended in 780 μL of 54 mM tris-hydrochloric acid aqueous solution (pH 8.0), 20 μL of acrylonitrile is added thereto, and the mixture is reacted for 15 to 60 minutes while gently stirring at 20° C. After the reaction is completed, analysis of the reaction solution is performed using HPLC to measure an amount (Q) of the produced amide compound (or may be calculated from an amount of the nitrile compound consumed). Reaction and analysis are performed 3 times or more for each condition. The quotient (R) is obtained by dividing the amount (Q) of the amide compound obtained by nitrile hydratase after the acid treatment by the amount (P) of the amide compound obtained by nitrile hydratase before the acid treatment. The quotient R is determined with respect to the wild-type *Pseudonocardia thermophila*-derived nitrile hydratase and with respect to the nitrile hydratase to be tested, respectively, and a ratio (test object/wild-type) of R value in nitrile hydratase to be tested to R value in the wild-type *Pseudonocardia thermophila*-derived nitrile hydratase is determined. When this ratio exceeds 1.0, the pH stability is improved as compared with the wild-type *Pseudonocardia thermophila*-derived nitrile hydratase.

The mutant nitrile hydratase according to the disclosure has a higher R value determined by the above than that of the wild-type *Pseudonocardia thermophila*-derived nitrile hydratase, and the R value of the mutant nitrile hydratase is preferably 1.1 times or more, more preferably 1.2 times or more, even more preferably 1.3 times or more, even more preferably 1.4 times or more the R value of the wild-type *Pseudonocardia thermophila*-derived nitrile hydratase.

Further, as described above, the mutant nitrile hydratase is an enzyme with excellent pH stability in that the mutant nitrile hydratase exhibits an enzyme activity in a wide pH range as compared with the conventional mutant nitrile hydratase with respect to the synthesis reaction of the amide compound from the nitrile compound. As a result of consideration by the present inventors of the factors that improve the pH stability of the enzyme activity of the nitrile hydratase in all of the amino acid residue substitutions of (a) to (e) described above, it was found that all the amino acids involved in the amino acid residue substitutions (a) to (e) are present in the vicinity of the substrate pocket of the enzyme. It is thought that the three-dimensional structure (folding state) of the protein is maintained in a good state in a wide pH range by including one or more of the amino acid residue substitutions (a) to (e) described above. Therefore, the amino acid residue substitution of (a) to (e) is considered to be a group of amino acid residue substitution (amino acid residue substitution group A).

Further, in the mutant nitrile hydratase, a dimer in which the α subunit and the β subunit are associated is a basic structural unit thereof, and the dimer is further associated to form a tetramer. A cysteine residue, which is the 111th amino acid residue from the N terminal of the α subunit, is subjected to post-translational modification into cysteine sulfinic acid (Cys-SOOH) and a cysteine residue, which is the 113th amino acid residue from the N terminal of the α subunit, is subjected to post-translational modification into cysteine sulfenic acid (Cys-SOH), respectively, and the polypeptide chain of the α subunit and the cobalt atom are bonded via the modified amino acid residues to form an active center.

A plasmid capable of expressing the wild-type *Pseudonocardia thermophila*-derived nitrile hydratase in a large amount in a transformant and a cell line transformed with the above plasmid, MT-10822 (Accession No. FERM BP-5785, which is deposited in the International Patent Organism Depositary (NITE-IPOD), 1-1-1 Higashi, Tsukuba, Ibaraki since Feb. 7, 1996) can be used. In addition, the modified nitrile hydratase can be obtained by using a conventional gene manipulation technology. When the homology of the amino acid sequence is high, the three-dimensional structure of the protein is considered to have a high probability of having a similar structure regardless of the genus and species of the strain including the protein, and thus the effect obtained by the introduction of one or more of the amino acid residue substitutions (a) to (e) is exerted on a general *Pseudonocardia thermophila*-derived nitrile hydratase as defined above, including the modified nitrile hydratase. In addition, the obtained mutant nitrile hydratase may have a pH stability which is more improved as compared to before introduction of one or more of the amino acid residue substitutions (a) to (e), the pH stability being evaluated by an enzyme activity at pH 4.0 relative to the enzyme activity at pH 8.0.

In addition, the mutant nitrile hydratase includes at least one of the amino acid residue substitutions (a) to (e). The mutant nitrile hydratase may include only one amino acid residue substitution of (a) to (e), or may include two or more amino acid residue substitutions. For example, examples of combinations with two amino acid residue substitutions may include a combination of (a) and (b), a combination of (a) and (c), a combination of (a) and (d), a combination of (a) and (e), a combination of (b) and (c), a combination of (b) and (d), a combination of (b) and (e), a combination of (c) and (d), a combination of (c) and (e), a combination of (d) and (e), and a combination of (d) and (f).

Examples of combinations with three amino acid residue substitutions may include a combination of (a), (b), and (c), a combination of (a). (b), and (d), a combination of (a), (b), and (e), a combination of (a). (c), and (d), a combination of (a), (c), and (e), a combination of (a), (d), and (e), a combination of (b), (c), and (d), a combination of (b), (c), and (e), a combination of (b), (d), and (e), and a combination of (c), (d), and (e) may be included. Examples of combinations with four amino acid residue substitutions may include a combination of (a), (b), (c), and (d), a combination of (a), (b), (c), and (e), a combination of (a), (b), (d), and (e), a combination of (a), (c), (d), and (e), and a combination of (b), (c), (d), and (e).

Five amino acid residue substitutions (a) to (e) may be combined and substituted.

In an embodiment, the mutant nitrile hydratase includes one or more amino acid residue substitutions selected from the group consisting of the above amino acid residue substitution (b) and the amino acid residue substitutions of (a) and (c) to (e). The substitution of one or more amino acid residue substitutions in the group consisting of the amino acid residue substitutions (a) and (c) to (e) together with the above amino acid residue substitution (b) may be a substitution of two amino acid residues, a substitution of three amino acid residues, or a substitution of four amino acid residues (i.e. all of (a) and (c) to (e)). Further, in this embodiment, the mutant nitrile hydratase may further have the above amino acid residue substitution (f).

As described above, the modified nitrile hydratase to be subjected to the introduction of at least one of the amino acid residue substitutions (a) to (e) may include modification such as amino acid substitution, or the like, with respect to the wild-type *Pseudonocardia thermophila*-derived nitrile hydratase or the specific sequences (1) to (5) described above. Thus, the mutant nitrile hydratase may include not only the amino acid residue substitutions (a) to (e) but also an amino acid residue substitution at a position other than the amino acid residue substitutions (a) to (e) as compared with the wild-type *Pseudonocardia thermophila*-derived nitrile hydratase or the specific sequences (1) to (5) described above. As described above, the mutant nitrile hydratase including other amino acid residue substitution can also obtain an effect obtained by the amino acid residue substitution group A located at a specific position on the three-dimensional structure.

In an embodiment, the mutant nitrile hydratase according to the disclosure has an improvement not only in the pH stability but also in an initial rate of a reaction for producing the amide compound from the nitrile compound. In other words, by introducing at least one of the amino acid residue substitutions (a) to (e) into wild-type *Pseudonocardia thermophila*-derived nitrile hydratase or the modified nitrile hydratase, a nitrile hydratase showing an initial reaction rate that is higher than the initial reaction rate before the introduction is obtained. The initial reaction rate, for example, may be determined by suspending 40 μL of the culture completion solution of the transformant producing the mutant nitrile hydratase in 740 μL of 54 mM tris-hydrochloric acid aqueous solution (pH 8.0), adding 20 μL of acrylonitrile thereto, reacting the mixture for 15 minutes to 60 minutes while gently stirring at 20° C., and analyzing the reaction solution using HPLC after the reaction is completed. Further, the mutant nitrile hydratase according to the disclosure to preferably exhibit a higher initial reaction rate at pH 8.0, and more preferably, 1.1 times or more the initial reaction rate, more preferably 1.2 times or more the initial reaction rate, more preferably 1.3 times or more the initial reaction rate, and more preferably 1.4 times or more the initial reaction rate as compared with the initial reaction rate of the wild-type *Pseudonocardia thermophila*-derived nitrile hydratase.

The mutant nitrile hydratase can be produced by the following method. For example, an expression vector including DNA encoding the mutant nitrile hydratase may be prepared, an arbitrary host cell may be transformed with the expression vector to obtain a transformant or a cell line, and subsequently, the transformant or the cell line may be cultured to produce the mutant nitrile hydratase.

Here, the gene encoding the wild-type *Pseudonocardia thermophila*-derived nitrile hydratase is composed of a nucleotide sequence shown in SEQ ID NO: 3 and a nucleotide sequence shown in SEQ ID NO: 4. Further, the nucleotide sequence represented by SEQ ID NO: 3 corresponds to an amino acid sequence consisting of SEQ ID NO: 1, and the nucleotide sequence represented by SEQ ID NO: 4 corresponds to an amino acid sequence consisting SEQ ID NO: 2.

In addition, the DNA encoding the mutant nitrile hydratase has, at least, the following nucleotide substitutions in one or more codons corresponding to the amino acid residue substitution positions of the above (a) to (e) (total 5 parts) in the nucleotide sequence represented by SEQ ID NO: 3 or in the nucleotide sequence represented by SEQ ID NO: 4, and a nucleotide substitution corresponding to the modified nitrile hydratase in other positions as well.

Specifically, for example, in the case of producing a mutant in which the Asp residue, which is the 40th amino acid residue from the N terminal of the α subunit of the wild-type *Pseudonocardia thermophila*-derived nitrile hydratase, is substituted with Asn, a DNA in which GAC, which is a nucleotide at positions from 118 to 120 from the 5' end of the nucleotide sequence represented by SEQ ID NO: 3, is substituted with AAC or AAT, is used.

In the case of producing a mutant in which the Ala residue, which is the 43th amino acid residue from the N terminal of the α subunit of the wild-type *Pseudonocardia thermophila*-derived nitrile hydratase, is substituted with Val, a DNA in which GCC, which is a nucleotide at positions from 127 to 129 from the 5' end of the nucleotide sequence represented by SEQ ID NO: 3, is substituted with GTT, GTC, GTA or GTG is used.

In the case of producing a mutant in which the Gly residue, which is the 205th amino acid residue from the N terminal of the β subunit of the wild-type *Pseudonocardia thermophila*-derived nitrile hydratase, is substituted with Val, a DNA in which GGG which is a nucleotide at positions from 613 to 615 from the 5' end of the nucleotide sequence represented by SEQ ID NO: 4, is substituted with GTT, GTC, GTA or GTG is used.

In the case of producing a mutant in which the Pro residue, which is the 206th amino acid residue from the N terminal of the β subunit of the wild-type *Pseudonocardia thermophila*-derived nitrile hydratase, is substituted with Gin, a DNA in which CCG, which is a nucleotide at positions from 616 to 618 from the 5' end of the nucleotide sequence represented by SEQ ID NO: 4, is substituted with CAA or CAG, is used.

In the case of producing a mutant in which the Tyr residue, which is the 215th amino acid residue from the N terminal of the α subunit of the wild-type *Pseudonocardia thermophila*-derived nitrile hydratase, is substituted with Asn, a DNA in which TAC, which is a nucleotide at positions from 643 to 645 from the 5' end of the nucleotide sequence represented by SEQ ID NO: 4, is substituted with AAC or AAT, is used.

Further, with respect to the amino acid residue substitution (f), in the case of producing a mutant in which the Thr residue, which is the 36th amino acid residue from the N terminal of the α subunit of the wild-type *Pseudonocardia thermophila*-derived nitrile hydratase, is substituted with Trp, a DNA in which ACG, which is a nucleotide at positions from 106 to 108 from the 5' end of the nucleotide sequence represented by SEQ ID NO: 3, is substituted with TGG, is used.

The expression vector includes a gene encoding the α subunit of the mutant nitrile hydratase and a gene encoding the β subunit of the mutant nitrile hydratase, and also elements enabling production of the mutant nitrile hydratase by the transformant or the cell line, such as a regulatory region required for the expression of each gene, a region required for autonomous replication, and the like, if necessary. The host cell into which the expression vector is introduced may be any cell, for example, *Escherichia coli*.

The regulatory regions required for expression may include a promoter sequence (including an operator sequence for controlling transcription), a ribosome binding sequence (SD sequence), a transcription termination sequence, and the like. Specific examples of the promoter sequence may include a trp promoter of tryptophan operon derived from *E. coli*, a lac promoter of lactose operon, a PL promoter and a PR promoter derived from lambda phage, and the like. Further, a sequence that is artificially designed and modified such as a tac promoter or a trc promoter can be used.

As the ribosome binding sequence, a sequence having TAAGGAGGT included in SEQ ID NO: 74 is preferable. Regarding the sequence order on the expression vector of the regulatory region, it is preferable that the promoter sequence and the ribosome binding sequence are located at the 5'-end upstream side as compared with a gene encoding the mutant nitrile hydratase, and it is preferable that the transcription termination sequence is located at the 3'-end downstream side as compared with a gene encoding the mutant nitrile hydratase. Further, by the regulatory region, the α subunit gene and the β subunit gene of the mutant nitrile hydratase may be expressed as independent cistrons, respectively, or may be expressed as a polycistron by a common regulatory region.

Examples of the vector that satisfies the above requirements may include pBR322, pUC18, pBluescript, pKK223-3, and pSC101 which include an autonomously replicable region in *E. coli*.

As a method for constructing the expression vector according to the disclosure by inserting a gene encoding the mutant nitrile hydratase into the vector together with a region required for expressing an activity of the mutant nitrile hydratase, a method for transforming the expression vector into a desired host cell, a method of producing nitrile hydratase in the transformant, and the like, general methods or host cells known in the fields of molecular biology, biotechnology, and genetic engineering such as described in "Molecular Cloning 3rd Edition" (J. Sambrook, and the like; Cold Spring Harbor Laboratory Press, 2001), and the like, can be adopted.

The transformant obtained by transforming the above-described expression vector into a desired host cell can be cultured in a medium to produce a mutant nitrile hydratase based on the nitrile hydratase gene included in the expression vector. When the host cell is *E. coli*. LB medium, M9 medium, or the like is generally used as a medium for culturing the transformant. More preferably, the medium contains 0.1 µg/mL or more of Fe ion and Co ion as components in the medium. The transformant may be inoculated in a medium and grown at an appropriate culture temperature (generally, from 20° C. to 50° C.).

When a mutant nitrile hydratase having a desired enzyme activity is produced by expressing the gene encoding the mutant nitrile hydratase, a gene encoding a protein involved in the activation of the nitrile hydratase may also be expressed.

The protein involved in activation of the nitrile hydratase is a protein having a property that whether or not the protein is expressed directly affects the activation of nitrile hydratase, and may include, as a representative example, a protein (nitrile hydratase activating protein) involved in the activation of the *Pseudonocardia thermophila*-derived nitrile hydratase described in JP-A No. H11-253168. The sequence of the nitrile hydratase activating protein is represented by SEQ ID NO: 75.

<Nucleic Acid>

The nucleic acid according to the disclosure has a nucleotide sequence encoding the amino acid sequence of the mutant nitrile hydratase.

As a method of synthesizing a nucleotide sequence encoding the amino acid sequence of the mutant nitrile hydratase, there are a method of introducing a mutation point into a nucleotide sequence encoding a corresponding wild-type *Pseudonocardia thermophila*-derived nitrile hydratase, a method of chemically synthesizing the entire nucleotide sequence including the mutation point, and the like. As a method of generating a mutation in a gene using a nucleotide sequence encoding a wild-type *Pseudonocardia thermophila*-derived nitrile hydratase as a template, for example, a site-specific mutation method (Kramer, W. and frita, H. J., Methods in Enzymology, vol. 154, P. 350(1987)), a recombinant PCR method (PCR Technology, Stockton Press (1989), a method of chemically synthesizing DNA at a specific part, a method of treating the gene with hydroxylamine, a method of irradiating a strain holding a gene with UV light, a method of treating the gene with a chemical agent such as nitrosoguanidine, nitrous acid, or the like, a method of using a commercially available mutagenesis kit, and the like, may be included. The nucleic acid according to the disclosure may) be DNA or RNA.

<Vector>

The vector according to the disclosure is not particularly limited as long as it is a vector including a nucleic acid represented by a nucleotide sequence encoding the amino acid sequence of the mutant nitrile hydratase, and may include a vector obtained by introducing the mutant nitrile hydratase into a known vector, as an example. In addition, the vector may be a phage vector or a plasmid vector.

<Expression Vector>

The expression vector according to the disclosure is not particularly limited as long as it is an expression vector including a nucleic acid represented by a nucleotide sequence encoding the amino acid sequence of the mutant nitrile hydratase, but the plasmid vector or the phage vector showing a constitution as shown below is more preferable from the viewpoint of improving a transformation efficiency, a translation efficiency, or the like.

[Basic Structure of Expression Vector]

The expression vector includes a nucleotide sequence encoding the mutant nitrile hydratase and is not particularly limited as long as the expression vector is capable of transforming the host cell. If necessary, the expression vector may include a nucleotide sequence constituting another region (hereinafter simply referred to as "another region") in addition to the nucleotide sequence. Examples of another region may include a regulatory region required for the transformant to produce the mutant nitrile hydratase, a region required for autonomous replication, and the like.

In addition, from the viewpoint of facilitating selection of the transformant, the expression vector may further include a nucleotide sequence encoding a selection gene that can be a selective marker.

The regulatory regions required to produce the mutant nitrile hydratase may include a promoter sequence (including an operator sequence for controlling transcription), a ribosome binding sequence (SD sequence), a transcription termination sequence, and the like.

[Expression Vector when Yeast is Used as Host Cell]

When yeast is used as a host cell, it is preferable that the expression vector includes a promoter sequence in addition to the nucleotide sequence encoding the mutant nitrile hydratase. As the promoter sequence, any promoter sequence may be used as long as it can express the mutant nitrile hydratase in a transformant using yeast as a host cell.

For example, promoter sequences such as an alcohol dehydrogenase (ADH1) promoter, a phosphoglycerate kinase (PGK1) promoter, a peptide chain elongation factor (TEF) promoter, a glycerol 3-phosphate dehydrogenase (GPD) promoter, a galactokinase (GAL1) promoter, a metallothionein (CUP1) promoter, an inhibitory acid phosphatase (PHO5) promoter, a glyceraldehyde-3-phosphate dehydrogenase (GAPDH) promoter, and the like, are used.

It should be noted that the origin of the promoter sequence is not limited to yeast becoming as a host cell.

An exogenous promoter such as a cytomegalovirus (CMV) promoter, or the like, may be used. These can be appropriately selected depending on the origin and type of enzyme to be used.

In addition, the expression vector may include a secretion signal. As a result, when the transformant produces the mutant nitrile hydratase, it is possible to secrete the mutant nitrile hydratase outside the cell.

The secretion signal is not particularly limited as long as the mutant nitrile hydratase is capable of being secreted from the yeast that becomes a host cell. From the viewpoint of secretion efficiency, it is preferable to use an α factor signal sequence, an invertase signal sequence, an acid phosphatase signal sequence, a glucoamylase signal sequence, and the like.

Specific examples of expression vectors including the promoter sequence or the secretion signal as described above may include pRS423, pRS424, YEplac195, and the like.

[Expression Vector when Filamentous Fungus is Used as Host Cell]

When the filamentous fungus is used as a host cell, it is preferable that the expression vector includes a promoter sequence in addition to the nucleotide sequence encoding the mutant nitrile hydratase. As the promoter sequence, any promoter sequence may be used as long as it can express the mutant nitrile hydratase in a transformant using the filamentous fungus as a host cell.

Appropriate expression vectors with respect to the filamentous fungus are described in van den Hondel, C. A. M. J. J. et al. (1991) In: Bennett, J. W. and Lasure, L. L. (eds.) More gene Manipulations in Fungi. Academic Press, pp. 396-428.

Further, other commonly used expression vectors such as pUC18, pBR322, pUC100, pSL1180 (manufactured by Pharmacia Inc.), pFB6, and *Aspergillus* pRAX. *Trichoderma* pTEX, and the like, may also be used.

[Expression Vector when Prokaryote is Used as Host Cell]

When the prokaryote such as *E. coli, Bacillus subtilis*, actinomycetes, or the like, is used as the host cell, it is preferable that the expression vector includes a promoter sequence in addition to the nucleotide sequence encoding the mutant nitrile hydratase. Further, the expression vector may include a ribosome binding sequence, a transcription termination sequence, or the like, in addition to the promoter sequence.

Examples of the promoter sequence may include a trp promoter of tryptophan operon derived from *E. coli*, a lac promoter of lactose operon, a PL promoter and a PR promoter derived from lambda phage, a gluconate synthase promoter (gnt) derived from *Bacillus subtilis*, an alkaline protease promoter (apr), a neutral protease promoter (npr), an α-amylase promoter (amy), and the like.

Further, a promoter sequence that is independently modified or designed, such as the tac promoter, can also be used.

As the ribosome binding sequence, sequences derived from *Escherichia coli* or *Bacillus subtilis* may be included, but there is no particular limitation as long as the ribosome binding sequence is a sequence functioning in a desired host cell such as *Escherichia coli, Bacillus subtilis*, or the like.

As the ribosome binding sequence, for example, a sequence produced by DNA synthesis of a consensus sequence continuous with 4 nucleotides or more, and the like, among the sequences complementary to the 3' end region of 16S ribosomal RNA, may be included.

The transcription termination sequence is not necessarily required, but sequences that are independent of ρ factors, such as a lipoprotein terminator, a trp operon terminator, and the like, may be used.

The sequence order of these regulatory regions on the expression vector is not particularly limited, but considering the transcription efficiency, it is preferable to sequentially arrange a promoter sequence from the 5' end upstream side, a ribosome binding sequence, a gene encoding a target protein, and a transcription termination sequence.

Specific examples of the expression vector may include pBR322, pUC18, Bluescript II SK(+), pKK223-3, pSC101 that include an autonomously replicable region in *E. coli*, and pUB110, pTZ4, pC194, ρ11, φ1, φ105, and the like, that include an autonomously replicable in *Bacillus subtilis*, can be used as the expression vector.

Further, as an example of the expression vector capable of autonomous replication in two or more kinds of hosts, pHV14, TRp7, YEp7, and pBS7, and the like, can be used as the expression vector.

[Method for Producing Transformant]

The transformant according to the disclosure can be produced by a known method. For example, a method in which the expression vector including the nucleotide sequence encoding the mutant nitrile hydratase according to the disclosure and the other region if necessary is constructed and the expression vector is transformed into a desired host cell, and the like, can be included. Specifically, common methods known in the field of molecular biology, bioengineering, and genetic engineering described in Sambrook, J., et. al., "Molecular Cloning A Laboratory Manual, 3rd Edition", Cold Spring Harbor Laboratory Press, (2001), and the like, can be used.

The transformant according to the disclosure can be constructed by not only incorporating the expression vector into the host cell but also introducing a silent mutation so that a codon having a low frequency of use in the host cell is made into a codon having a high frequency of use, and the like, if necessary.

This may increase a production amount of protein derived from the mutant nitrile hydratase incorporated in the expression vector.

Regarding the introduction of the silent mutation, in a case in which the introduction is a method for adjusting the nitrile hydratase gene on the expression vector and the codon of the signal sequence for secretion of the nitrile hydratase gene extracellularly according to the frequency of use of the codon in the host cell, a method of silent mutagenesis, a mutation point, the type of nucleotide to be changed, and the like, are not particularly limited.

<Method for Producing Mutant Nitrile Hydratase>

A method for producing a mutant nitrile hydratase according to the disclosure includes culturing the transformant in a medium, and recovering the mutant nitrile hydratase from at least one of the cultured transformant and medium.

[Method for Culturing Transformant]

Conditions for culturing the transformant obtained by transformation with the expression vector are the same as those for the host cell before transformation, and known conditions can be used.

As a medium, any of a synthetic medium and a natural medium can be used as long as the medium contains an appropriate amount of a carbon source, a nitrogen source, inorganic matter, and other nutrients. Known components can be used as components used in the medium. For example, organic nutrients such as meat extract, yeast extract, malt extract, peptone, NZ amine, and potato, and the like, carbon sources such as glucose, maltose, sucrose, starch, and organic acid, and the like, nitrogen sources such as ammonium sulfate, urea, and ammonium chloride, and the like, inorganic nutrients such as phosphoric acid salts, magnesium, potassium, and iron, and the like, and vitamins can be used in appropriate combination.

In addition, in culturing the transformant transformed with the expression vector including the selective marker, for example, in a case in which the selective marker is drug-resistant, a medium including a corresponding drug is used, and in a case in which the selective marker is nutritionally required, a medium not including the corresponding nutrient is used. The pH of the medium can be selected within the range of from pH 4 to pH 8.

The culturing may be performed in a liquid medium containing the above medium by conventional culture methods such as shaking culture, aeration stirring culture, continuous culture, fed-batch culture, and the like, of the transformant.

Culture conditions may be appropriately selected according to the type of the transformant, the culture medium, and the culture method, and there is no particular limitation as long as the transformant grows and the mutant nitrile hydratase according to the disclosure is capable of being produced.

The culturing is performed aerobically at a culture temperature of from 20° C. to 45° C., and preferably from 24° C. to 37° C.

The culture period may have a range of from 1 day to 7 days until the content of protein having the desired mutant nitrile hydratase activity is maximum.

Step of Recovering Mutant Nitrile Hydratase

A step of recovering a mutant nitrile hydratase is a step of recovering the mutant nitrile hydratase from at least one of the cultured transformant and the medium after the culturing.

As a method for recovering the mutant nitrile hydratase according to the disclosure after culturing the transformed transformant, a method commonly used in this field can be used.

In a case in which the mutant nitrile hydratase according to the disclosure is secreted outside the transformed transformant, a crude enzyme solution can be easily obtained by performing centrifugation, filtration, or the like, on the culture of the transformant. Further, in a case in which the mutant nitrile hydratase according to the disclosure is accumulated in the transformed transformant, the cultured transformant is recovered by means such as centrifugation, or the like, the recovered transformant is suspended in a buffer, and a cell membrane of the transformant is disrupted according to a known method such as lysozyme treatment, freeze-thawing, ultrasonic disruption, or the like, thereby recovering the crude enzyme solution.

The crude enzyme solution can be used as a concentrated enzyme by concentrating the crude enzyme solution by ultrafiltration, or the like, and adding a preservative, or the like, to the crude enzyme solution. In addition, after concentrating, a powder enzyme of the mutant nitrile hydratase can be obtained by a spray drying method, or the like.

In a case in which the crude enzyme solution having the recovered nitrile hydratase activity requires separation and purification, for example, salting out with ammonium sulfate or the like, organic solvent precipitation method with alcohol or the like, membrane separation method such as dialysis, ultrafiltration, or the like, or a known chromatographic separation method such as ion exchange chromatography, reversed phase high speed chromatography, affinity chromatography, gel filtration chromatography, or the like, can be performed in appropriate combination.

The method for producing an amide compound according to the disclosure includes bringing the mutant nitrile hydratase into contact with a nitrile compound. The mutant nitrile hydratase catalyzes a reaction for synthesizing an amide compound from a nitrile compound. A method for producing an amide compound is described in more detail below.

First, a transformant or a cell line that produces the mutant nitrile hydratase is cultured, and the obtained culture solution, cells, or cell-treated products are brought into contact with the nitrile compound in the medium. Thus, the mutant nitrile hydratase is brought into contact with the nitrile compound and the mutant nitrile hydratase converts the nitrile compound to the corresponding amide compound. The term "cell-treated product" as used herein refers to an extract or a ground product from the transformant, a post-isolate of a crude enzyme preparation that is obtained by separating nitrile hydratase active fractions of the extract or the ground product, or a purified enzyme product obtained by further purification, or the like, or an immobilized product obtained by immobilizing the transformant, or the extract, the ground product, or the post-isolate of the transformant using an appropriate means.

A temperature for bringing the mutant nitrile hydratase into contact with the nitrile compound described above is preferably within a temperature range in which the mutant nitrile hydratase is not inactivated, more preferably from 0° C. to 60° C., and more preferably from 15° C. to 35° C. For example, a culture solution obtained by culturing a transformant or a cell line producing the mutant nitrile hydratase may be directly added to an aqueous solution including a nitrile compound, or the culture solution may be centrifuged to separate the bacterial cells and the bacterial cells may be added to an aqueous solution including the nitrile compound. The pH of the aqueous solution at the time of reaction is preferably from 7 to 9, and more preferably from 7.5 to 8.5. The nitrile compound may be present in the aqueous solution at a concentration of, for example, from 0.25% to 20.0% by volume, and more preferably from 2.0% to 5.0% by volume. Details of the culturing of the transformant are the same as described in the section on the method for producing a mutant nitrile hydratase.

Specific examples of the nitrile compound are not particularly limited as long as the mutant nitrile hydratase is a compound capable of acting as a substrate. Preferably, as a representative example, the nitrile compound may include a nitrile compound having from 2 to 4 carbon atoms such as acetonitrile, propionitrile, acrylonitrile, methacrylonitrile, n-butyronitrile, isobutyronitrile, crotononitrile, α-hydroxyisobutyronitrile, or the like. Since a nitrile group in the nitrile compound is converted into an amide group by hydration, for example, acrylonitrile can be converted to acrylamide.

Then, by adding activated carbon to the medium without deactivating the mutant nitrile hydratase, the produced amide compound is purified from the nitrile compound using the mutant nitrile hydratase as a catalyst, without completing the synthesis reaction of the amide compound.

In addition, a reaction for producing the amide compound from the nitrile compound by the contact with the mutant nitrile hydratase is performed under conditions according to the optimum pH of the nitrile hydratase, for example neutral to basic conditions such as pH from 7 to 9. The pH can be adjusted, for example, by using a basic material such as ammonia or sodium hydroxide in a buffer if necessary. Meanwhile, purification of the amide compound is preferably performed under acidic conditions such as, for example, pH from 3.5 to 6.5. This is to efficiently remove impurities, particularly proteins, included in a amide compound-containing liquid. The change into acidic pH can be performed by using an acid such as acetic acid, propionic acid, octanoic acid, valeric acid, hydrochloric acid, acrylic acid, methacrylic acid, or the like. Thus, the method for producing the amide compound preferably includes a purification step of removing impurities from a solution including the produced amide compound under the condition of pH from 3.5 to 6.5. In this step, it is preferable to use activated carbon to remove impurities. That is, in an embodiment, the method for producing an amide compound according to the disclosure further includes purifying the amide compound with activated carbon. Therefore, it is preferable that the mutant nitrile hydratase has an improved enzyme activity than before the introduction of at least one of the amino acid residue substitutions (a) to (e), preferably, in condition of pH from 3.5 to 6.5. The pH condition may be a pH of 5.0 or less for more efficient removal of unnecessary proteins.

As described above, the mutant nitrile hydratase according to the disclosure can achieve high conversion efficiency throughout the step of producing an amide compound from a nitrile compound, due to the improved pH stability. Although these embodiments have been described above, these are provided as an example, and various configurations other than the above can be adopted.

EXAMPLE

The embodiment is described in more detail by the following Examples, but the present invention is not limited in any way by the following Examples. In addition, in the following Examples, the term "mutation site" refers to a position of a difference in amino acid sequence from the wild-type *Pseudonocardia thermophila*-derived nitrile hydratase that has an α subunit having the amino acid sequence represented by SEQ ID NO: 1; and a β subunit having the amino acid sequence represented by SEQ ID NO: 2.

[Comparative Example 1] Obtainment of Wild-Type *Pseudonocardia thermophila*-Derived Nitrile Hydratase (1)

10 mL of LB liquid medium was prepared in a 30 mL test tube and the liquid medium was sterilized by autoclave at 121° C. for 20 minutes. Ampicillin was added to the liquid medium to have a final concentration of 100 µg/mL, and then one platinum loop of the cell line MT-10822 was inoculated and cultured at 37° C. and 300 rpm for about 20 hours. Thereafter, 1 mL of the obtained culture solution was fractionated into an appropriate centrifuge tube, and the bacterial cells were separated by centrifugation (15000 rpm×5 minutes).

Subsequently, a plasmid pPT-DB1 was prepared from the bacterial cells obtained by separation by an alkaline SDS extraction method. The prepared plasmid was transformed into competent cells of *Escherichia coli* HB101 (Toyobo Co., Ltd.) to obtain a transformant (1). The transformant (1) produces a nitrile hydratase (1) which is the wild-type *Pseudonocardia thermophila*-derived nitrile hydratase.

[Comparative Example 2] Obtainment of Mutant Nitrile Hydratase (2)

In order to obtain a transformant (2) expressing a mutant nitrile hydratase in which Asp, which is the 92nd amino acid residue from the N terminal of the α subunit of the wild-type *Pseudonocardia thermophila*-derived nitrile hydratase, is substituted with Glu, as shown in Table 14, a site-specific mutagenesis using "LA PCR in vitro mutagenesis Kit" (hereinafter referred to as mutagenesis kit) manufactured by Takara Shuzo Co., Ltd., was performed. A PCR reaction was performed using the wild-type *Pseudonocardia thermophila*-derived nitrile hydratase expression plasmid pPT-DB1 as a template.

The PCR reaction No. 1 was performed by repeating a condition of heat denaturation (98° C.) for 15 seconds, annealing (55° C.) for 30 seconds, and elongation reaction (72° C.) for 120 seconds 25 cycles in a system (the composition according to the conditions described in the mutagenesis kit) with a total amount of 50 µL including 50 pmol each of the primer of SEQ ID NO: 5 and the M13 primer M4 (the sequence represented by SEQ ID NO: 12). The PCR reaction No. 2 was performed in the same manner as the PCR reaction No. 1 in a system (the composition according to the conditions described in the mutagenesis kit) with a total amount of 50 µL including 50 pmol each of the MUT4 primer (the sequence represented by SEQ ID NO: 14) and the M13 primer RV (the sequence represented by SEQ ID NO: 13).

As a result obtained by performing analysis of the DNA amplification product by agarose electrophoresis (agarose concentration of 1.0 wt %) using 5 µL of each reaction terminated solution for the PCR reactions No. 1 and No. 2, the presence of the amplified DNA product could be confirmed.

Excess primer and dNTP were removed from each PCR reaction completed solution using Microcon 100 (Takara Shuzo Co., Ltd.), and then TE was added to prepare 50 µL of each solution. A total amount of 47.5 µL of an annealing solution (composition is based on the conditions described in the mutagenesis kit) including 0.5 µL of each TE solution was prepared and subjected to heat denaturation treatment (98° C.) for 10 minutes. Then, the mixture was cooled at a constant rate up to 37° C. over 60 minutes, and continuously maintained at 37° C. for 15 minutes, thereby performing annealing treatment.

0.5 µL of TaKaRa LA Taq was added to the annealing treatment liquid, and heat treatment was performed at 72° C. for 3 minutes to complete hetero double strands.

Next, 50 pmol each of the M13 primer M4 (sequence represented by SEQ ID NO: 12) and the M13 primer RV (sequence represented by SEQ ID NO: 13) was added thereto to prepare a total amount of 50 µL, and then the PCR reaction No. 3 was performed by repeating a condition of heat denaturation (98° C.) for 15 seconds, annealing (55° C.) for 30 seconds, and elongation reaction (72° C.) for 120 seconds 25 cycles.

As a result of performing the analysis of the DNA amplification product by agarose electrophoresis (using Type VII low melting point agarose manufactured by Sigma-Aldrich; 0.8 wt % of agarose concentration) using 5 µL of the reaction completed solution of the PCR reaction No. 3, the presence of amplified DNA product of about 2 kb could be confirmed. Subsequently, only a DNA fragment of about 2 Kb was excised from the agarose gel, the agarose piece (about 0.1 g) was finely pulverized, suspended in 1 mL of TE solution, and incubated at 55° C. for 1 hour to thoroughly melt the agarose.

This molten solution was subjected to phenol/chloroform extraction and ethanol precipitation to purify the DNA fragment, and the DNA fragment was finally dissolved in 10 µL of TE. An amount of about 2 kb of purified amplified DNA fragment was digested with restriction enzymes EcoRI and HindIII, and this restriction enzyme treated solution was subjected to phenol/chloroform extraction and ethanol precipitation to purify the DNA fragment, and the DNA fragment was finally dissolved in 10 µL of TE.

Similarly, nitrile hydratase expression plasmid pPT-DB1 was digested with EcoRI and HindIII, followed by agarose gel electrophoresis (using Type VII low melting point agarose manufactured by Sigma-Aldrich; 0.7% of agarose concentration), and only about 2.7 Kb DNA fragment was excised from the agarose gel.

The excised agarose pieces (about 0.1 g) were finely pulverized, suspended in 1 mL of TE solution, and incubated at 55° C. for 1 hour to thoroughly melt the agarose.

This molten solution was subjected to phenol/chloroform extraction and ethanol precipitation to purify the DNA fragment, and the DNA fragment was finally dissolved in 10 µL of TE. The DNA fragments of about 2 kb and about 2.7 kb thus obtained were ligated using a DNA ligation kit (manufactured by Takara Shuzo Co., Ltd.), and transformed into competent cells of *E. coli* HB101 (manufactured by Toyobo Co., Ltd.) to obtain the transformant (2). Further, a plasmid was prepared from the bacterial cells by an alkaline SDS extraction method, the nucleotide sequence of the nitrile hydratase gene part was determined with a DNA sequencer, and it was confirmed that the plasmid pPT-DB1 described in Example 1 had a mutation in which Asp, which is the 92nd amino acid residue from the N terminal of the α subunit, was substituted with Glu. The transformant (2) produces a nitrile hydratase (2) having the mutation described in Table 14.

<Comparison of pH Stability>

The pH stability in the production of the amide compound using the thus-obtained transformant (2) and the transformant (1) including pPT-DB1 as a base thereof was compared by the following method. As a result, the relative pH stability of the nitrile hydratase (2) as compared with the nitrile hydratase (1) can be evaluated.

5 mL of LB liquid medium including 40 µg/mL ferric sulfate.heptahydrate and 10 µg/mL cobalt chloride.dihydrate were prepared in a test tube and sterilized by autoclave at 121° C. for 20 minutes.

Ampicillin was added to the liquid medium to have a final concentration of 100 µg/mL, and then one platinum loop of each transformant was inoculated and cultured at 37° C. and 200 rpm for about 20 hours.

40 µl of the culture completion solution was taken and suspended in 740 µL of 54 mM tris-hydrochloric acid aqueous solution (pH 8.0), 20 µL of acrylonitrile was added thereto, and the mixture was reacted for 15 minutes to 60 minutes while gently stirring at 20° C. After the reaction was completed, the reaction solution was analyzed using HPLC, and an enzyme activity for producing an amide compound from the nitrile compound was determined. The reaction and the analysis were performed on each transformant three times or more, and variation of data was corrected with dispensing operation, and the like.

Likewise, 1000 μl of the culture completion solution was taken and centrifuged to recover cells, 1000 μL of 50 mM citric acid buffer (pH 4.0) was added to the recovered bacterial cells, and the obtained solution was treated at 30° C. for 30 hours (acid treatment) with stirring. After the treatment, 780 μl of the solution was centrifuged to recover the bacterial cells, suspended in 780 μL of 54 mM tris-hydrochloric acid aqueous solution (pH 8.0), 20 μL of acrylonitrile was added thereto, and the mixture was reacted for 15 minutes to 60 minutes while gently stirring at 20° C. After the reaction was completed, the reaction solution was analyzed using HPLC, and an enzyme activity for producing an amide compound from the nitrile compound was determined. The reaction and the analysis were performed on each transformant three times or more, and variation of data was corrected with dispensing operation, and the like.

<Analysis Conditions>
Analytical Instrument: JASCO Corporation HPLC
Column: YMC Pack ODS-A (150×6.00 mm)
Analysis temperature: 40° C.
Mobile Phase: 3% acetonitrile, 10 mM phosphoric acid A ratio between an activity of bacterial cells treated with 50 mM citric acid buffer (pH 4.0) and an enzyme activity of untreated bacterial cells was taken as pH stability. The pH stability of the transformant (2) was 0.82 times that of the wild-type (1).

The above results show that even if the mutation is thought to raise the initial reaction rate under optimum conditions of nitrile hydratase (see International Publication No. WO 2010/055666), an improvement in pH stability is not necessarily caused.

[Example 1] Obtainment of Mutant Nitrile Hydratase (3)

In order to obtain a transformant (3) expressing a mutant nitrile hydratase having an amino acid residue substitution as shown in Table 14, a plasmid was obtained and the transformant (3) was obtained in the same manner as in Comparative Example 2 above except that a primer of SEQ ID NO: 7 was used in place of the primer of SEQ ID NO: 5. The transformant (3) produces a nitrile hydratase (3) having the mutation described in Table 14.

The pH stability of the nitrile hydratase (3) was evaluated by the method described in "Comparison of pH Stability" described above. The obtained results are shown in Table 14 below.

[Example 2] Obtainment of Mutant Nitrile Hydratase (4)

In order to obtain a transformant (4) expressing a mutant nitrile hydratase having an amino acid residue substitution as shown in Table 14, a plasmid was obtained and the transformant (4) was obtained in the same manner as in Comparative Example 2 above except that a primer of SEQ ID NO: 8 was used in place of the primer of SEQ ID NO: 5. The transformant (4) produces a nitrile hydratase (4) having the mutation described in Table 14.

The pH stability of the nitrile hydratase (4) was evaluated by the method described in "Comparison of pH Stability" described above. The obtained results are shown in Table 14 below.

[Example 3] Obtainment of Mutant Nitrile Hydratase (5)

In order to obtain a transformant (5) expressing a mutant nitrile hydratase having an amino acid residue substitution as shown in Table 14, a plasmid was obtained and the transformant (5) was obtained in the same manner as in Comparative Example 2 above except that a primer of SEQ ID NO: 9 was used in place of the primer of SEQ ID NO: 5. The transformant (5) produces a nitrile hydratase (5) having the mutation described in Table 14.

The pH stability of the nitrile hydratase (5) was evaluated by the method described in "Comparison of pH Stability" described above. The obtained results are shown in Table 14 below.

[Example 4] Obtainment of Mutant Nitrile Hydratase (6)

In order to obtain a transformant (6) expressing a mutant nitrile hydratase having an amino acid residue substitution as shown in Table 14, a plasmid was obtained and the transformant (6) was obtained in the same manner as in Comparative Example 2 above except that a primer of SEQ ID NO: 10 was used in place of the primer of SEQ ID NO: 5. The transformant (6) produces a nitrile hydratase (6) having the mutation described in Table 14.

The pH stability of the nitrile hydratase (6) was evaluated by the method described in "Comparison of pH Stability" described above. The obtained results are shown in Table 14 below.

[Example 5] Obtainment of Mutant Nitrile Hydratase (7)

In order to obtain a transformant (7) expressing a mutant nitrile hydratase having an amino acid residue substitution as shown in Table 14, a plasmid was obtained and the transformant (7) was obtained in the same manner as in Comparative Example 2 above except that a primer of SEQ ID NO: 11 was used in place of the primer of SEQ ID NO: 5. The transformant (7) produces a nitrile hydratase (7) having the mutation described in Table 14.

The pH stability of the nitrile hydratase (7) was evaluated by the method described in "Comparison of pH Stability" described above. The obtained results are shown in Table 14 below.

TABLE 14

| Nitrile Hydratase No. | Mutation Site | Before Mutation | After Mutation | pH Stability Relative Value For Wild-type | Note |
|---|---|---|---|---|---|
| (1) | Wild-type | None | None | 1.00 | Comparative Example 1 |
| (2) | α92 | Asp | Glu | 0.82 | Comparative Example 2 |
| (3) | α40 | Asp | Asn | 1.16 | Example 1 |
| (4) | α43 | Ala | Val | 1.17 | Example 2 |
| (5) | β205 | Gly | Val | 1.14 | Example 3 |

TABLE 14-continued

| Nitrile Hydratase No. | Mutation Site | Before Mutation | After Mutation | pH Stability Relative Value For Wild-type | Note |
|---|---|---|---|---|---|
| (6) | β206 | Pro | Gln | 1.15 | Example 4 |
| (7) | β215 | Tyr | Asn | 1.15 | Example 5 |

From the results shown in Table 14, it could be appreciated that each amino acid residue substitution belonging to the amino acid residue substitution group A alone resulted in an improvement in the pH stability of a nitrile hydratase. Meanwhile, the substitution of the Asp residue at the 92nd position from the N terminal of the α subunit with Glu, which does not belong to the amino acid residue substitution group A, did not improve the pH stability as compared with the wild-type *Pseudonocardia thermophila*-derived nitrile hydratase.

[Example 6] Obtainment of Mutant Nitrile Hydratase (8)

In order to obtain a transformant (8) expressing a mutant nitrile hydratase having an amino acid residue substitution as shown in Table 15, the transformant (8) was obtained in the same manner as in Comparative Example 2 above except that the plasmid of Example 1 was used as a template and a primer of SEQ ID NO: 6 was used in place of the primer of SEQ ID NO: 5. The transformant (8) produces a nitrile hydratase (8) having the mutation described in Table 15.

The pH stability of the nitrile hydratase (8) was evaluated by the method described in "Comparison of pH Stability" described above. The obtained results are shown in Table 15 below.

[Example 7] Obtainment of Mutant Nitrile Hydratase (9)

In order to obtain a transformant (9) expressing a mutant nitrile hydratase having an amino acid residue substitution as shown in Table 15, the transformant (9) was obtained in the same manner as in Comparative Example 2 above except that the plasmid of Example 2 was used as a template and a primer of SEQ ID NO: 6 was used in place of the primer of SEQ ID NO: 5. The transformant (9) produces a nitrile hydratase (9) having the mutation described in Table 15.

The pH stability of the nitrile hydratase (9) was evaluated by the method described in "Comparison of pH Stability" described above. The obtained results are shown in Table 15 below.

[Example 8] Obtainment of Mutant Nitrile Hydratase (10)

In order to obtain a transformant (10) expressing a mutant nitrile hydratase having an amino acid residue substitution as shown in Table 15, the transformant (10) was obtained in the same manner as in Comparative Example 2 above except that the plasmid of Example 3 was used as a template and a primer of SEQ ID NO: 6 was used in place of the primer of SEQ ID NO: 5. The transformant (10) produces a nitrile hydratase (10) having the mutation described in Table 15.

The pH stability of the nitrile hydratase (10) was evaluated by the method described in "Comparison of pH Stability" described above. The obtained results are shown in Table 15 below.

[Example 9] Obtainment of Mutant Nitrile Hydratase (11)

In order to obtain a transformant (11) expressing a mutant nitrile hydratase having an amino acid residue substitution as shown in Table 15, the transformant (11) was obtained in the same manner as in Comparative Example 2 above except that the plasmid of Example 4 was used as a template and a primer of SEQ ID NO: 6 was used in place of the primer of SEQ ID NO: 5. The transformant (11) produces a nitrile hydratase (11) having the mutation described in Table 15.

The pH stability of the nitrile hydratase (11) was evaluated by the method described in "Comparison of pH Stability" described above. The obtained results are shown in Table 15 below.

[Example 10] Obtainment of Mutant Nitrile Hydratase (12)

In order to obtain a transformant (12) expressing a mutant nitrile hydratase having an amino acid residue substitution as shown in Table 15, the transformant (12) was obtained in the same manner as in Comparative Example 2 above except that the plasmid of Example 5 was used as a template and a primer of SEQ ID NO: 6 was used in place of the primer of SEQ ID NO: 5. The transformant (12) produces a nitrile hydratase (12) having the mutation described in Table 15.

The pH stability of the nitrile hydratase (12) was evaluated by the method described in "Comparison of pH Stability" described above. The obtained results are shown in Table 15 below.

[Example 11] Obtainment of Mutant Nitrile Hydratase (13)

In order to obtain a transformant (13) expressing a mutant nitrile hydratase having an amino acid residue substitution as shown in Table 15, the transformant (13) was obtained in the same manner as in Comparative Example 2 above except that the plasmid of Example 1 was used as a template and a primer of SEQ ID NO: 8 was used in place of the primer of SEQ ID NO: 5. The transformant (13) produces a nitrile hydratase (13) having the mutation described in Table 15.

The pH stability of the nitrile hydratase (13) was evaluated by the method described in "Comparison of pH Stability" described above. The obtained results are shown in Table 15 below.

[Example 12] Obtainment of Mutant Nitrile Hydratase (14)

In order to obtain a transformant (14) expressing a mutant nitrile hydratase having an amino acid residue substitution as shown in Table 15, the transformant (14) was obtained in the same manner as in Comparative Example 2 above except that the plasmid of Example 1 was used as a template and a primer of SEQ ID NO: 9 was used in place of the primer of SEQ ID NO: 5. The transformant (14) produces a nitrile hydratase (14) having the mutation described in Table 15.

The pH stability of the nitrile hydratase (14) was evaluated by the method described in "Comparison of pH Stability" described above. The obtained results are shown in Table 15 below.

[Example 13] Obtainment of Mutant Nitrile Hydratase (15)

In order to obtain a transformant (15) expressing a mutant nitrile hydratase having an amino acid residue substitution as shown in Table 15, the transformant (15) was obtained in the same manner as in Comparative Example 2 above except that the plasmid of Example 2 was used as a template and a primer of SEQ ID NO: 9 was used in place of the primer of SEQ ID NO: 5. The transformant (15) produces a nitrile hydratase (15) having the mutation described in Table 15.

The pH stability of the nitrile hydratase (15) was evaluated by the method described in "Comparison of pH Stability" described above. The obtained results are shown in Table 15 below.

[Example 14] Obtainment of Mutant Nitrile Hydratase (16)

In order to obtain a transformant (16) expressing a mutant nitrile hydratase having an amino acid residue substitution as shown in Table 15, the transformant (16) was obtained in the same manner as in Comparative Example 2 above except that the plasmid of Example 2 was used as a template and a primer of SEQ ID NO: 10 was used in place of the primer of SEQ ID NO: 5. The transformant (16) produces a nitrile hydratase (16) having the mutation described in Table 15.

The pH stability of the nitrile hydratase (16) was evaluated by the method described in "Comparison of pH Stability" described above. The obtained results are shown in Table 15 below.

[Example 15] Obtainment of Mutant Nitrile Hydratase (17)

In order to obtain a transformant (17) expressing a mutant nitrile hydratase having an amino acid residue substitution as shown in Table 15, the transformant (17) was obtained in the same manner as in Comparative Example 2 above except that the plasmid of Example 2 was used as a template and a primer of SEQ ID NO: 11 was used in place of the primer of SEQ ID NO: 5. The transformant (17) produces a nitrile hydratase (17) having the mutation described in Table 15.

The pH stability of the nitrile hydratase (17) was evaluated by the method described in "Comparison of pH Stability" described above. The obtained results are shown in Table 15 below.

[Example 16] Obtainment of Mutant Nitrile Hydratase (18)

In order to obtain a transformant (18) expressing a mutant nitrile hydratase having an amino acid residue substitution as shown in Table 15, the transformant (18) was obtained in the same manner as in Comparative Example 2 above except that the plasmid of Comparative Example 1 was used as a template and a primer of SEQ ID NO: 15 was used in place of the primer of SEQ ID NO: 5. The transformant (18) produces a nitrile hydratase (18) having the mutation described in Table 15.

The pH stability of the nitrile hydratase (18) was evaluated by the method described in "Comparison of pH Stability" described above. The obtained results are shown in Table 15 below.

[Example 17] Obtainment of Mutant Nitrile Hydratase (19)

In order to obtain a transformant (19) expressing a mutant nitrile hydratase having an amino acid residue substitution as shown in Table 15, the transformant (19) was obtained in the same manner as in Comparative Example 2 above except that the plasmid of Example 3 was used as a template and a primer of SEQ ID NO: 11 was used in place of the primer of SEQ ID NO: 5. The transformant (19) produces a nitrile hydratase (19) having the mutation described in Table 15.

The pH stability of the nitrile hydratase (19) was evaluated by the method described in "Comparison of pH Stability" described above. The obtained results are shown in Table 15 below.

[Example 18] Obtainment of Mutant Nitrile Hydratase (20)

In order to obtain a transformant (20) expressing a mutant nitrile hydratase having an amino acid residue substitution as shown in Table 15, the transformant (20) was obtained in the same manner as in Comparative Example 2 above except that the plasmid of Example 4 was used as a template and a primer of SEQ ID NO: 11 was used in place of the primer of SEQ ID NO: 5. The transformant (20) produces a nitrile hydratase (20) having the mutation described in Table 15.

The pH stability of the nitrile hydratase (20) was evaluated by the method described in "Comparison of pH Stability" described above. The obtained results are shown in Table 15 below.

TABLE 15

| Nitrile Hydratase No. | Mutation Site | Before Mutation | After Mutation | pH Stability Relative Value For Wild-type | Note |
|---|---|---|---|---|---|
| (8)  | α36  | Thr | Trp | 1.22 | Example 6 |
|      | α40  | Asp | Asn |      |            |
| (9)  | α36  | Thr | Trp | 1.24 | Example 7 |
|      | α43  | Ala | Val |      |            |
| (10) | α36  | Thr | Trp | 1.25 | Example 8 |
|      | β205 | Gly | Val |      |            |
| (11) | α36  | Thr | Trp | 1.24 | Example 9 |
|      | β206 | Pro | Gln |      |            |
| (12) | α36  | Thr | Trp | 1.28 | Example 10 |
|      | β215 | Tyr | Asn |      |            |
| (13) | α40  | Asp | Asn | 1.31 | Example 11 |
|      | α43  | Ala | Val |      |            |
| (14) | α40  | Asp | Asn | 1.23 | Example 12 |
|      | β205 | Gly | Val |      |            |
| (15) | α43  | Ala | Val | 1.32 | Example 13 |
|      | β205 | Gly | Val |      |            |
| (16) | α43  | Ala | Val | 1.24 | Example 14 |
|      | β206 | Pro | Gln |      |            |
| (17) | α43  | Ala | Val | 1.22 | Example 15 |
|      | β215 | Tyr | Asn |      |            |
| (18) | β205 | Gly | Val | 1.32 | Example 16 |
|      | β206 | Pro | Gln |      |            |
| (19) | β205 | Gly | Val | 1.24 | Example 17 |
|      | β215 | Tyr | Asn |      |            |
| (20) | β206 | Pro | Gln | 1.24 | Example 18 |
|      | β215 | Tyr | Asn |      |            |

From the results shown in Table 15, it could be appreciated that each amino acid residue substitution belonging to the amino acid residue substitution group A resulted in an improvement in the pH stability of the nitrile hydratase even in a case in which the amino acid residue substitutions were combined with each other. In addition, it could be appreciated that in a case in which the amino acid residue substitutions belonging to the amino acid residue substitution group A were combined with each other or in a case in which the amino acid residue substitution was combined with the amino acid residue substitution (f), the pH stability tended to be further improved.

[Example 19] Obtainment of Mutant Nitrile Hydratase (21)

In order to obtain a transformant (21) expressing a mutant nitrile hydratase having an amino acid residue substitution as shown in Table 16, the transformant (21) was obtained in the same manner as in Comparative Example 2 above except that the plasmid of Example 7 was used as a template and a primer of SEQ ID NO: 9 was used in place of the primer of SEQ ID NO: 5. The transformant (21) produces a nitrile hydratase (21) having the mutation described in Table 16.

The pH stability of the nitrile hydratase (21) was evaluated by the method described in "Comparison of pH Stability" described above. The obtained results are shown in Table 16 below.

[Example 20] Obtainment of Mutant Nitrile Hydratase (22)

In order to obtain a transformant (22) expressing a mutant nitrile hydratase having an amino acid residue substitution as shown in Table 16, the transformant (22) was obtained in the same manner as in Comparative Example 2 above except that the plasmid of Example 11 was used as a template and a primer of SEQ ID NO: 9 was used in place of the primer of SEQ ID NO: 5. The transformant (22) produces a nitrile hydratase (22) having the mutation described in Table 16.

The pH stability of the nitrile hydratase (22) was evaluated by the method described in "Comparison of pH Stability" described above. The obtained results are shown in Table 16 below.

[Example 21] Obtainment of Mutant Nitrile Hydratase (23)

In order to obtain a transformant (23) expressing a mutant nitrile hydratase having an amino acid residue substitution as shown in Table 16, the transformant (23) was obtained in the same manner as in Comparative Example 2 above except that the plasmid of Example 7 was used as a template and a primer of SEQ ID NO: 11 was used in place of the primer of SEQ ID NO: 5. The transformant (23) produces a nitrile hydratase (23) having the mutation described in Table 16.

The pH stability of the nitrile hydratase (23) was evaluated by the method described in "Comparison of pH Stability" described above. The obtained results are shown in Table 16 below.

TABLE 16

| Nitrile Hydratase No. | Mutation Site | Before Mutation | After Mutation | pH Stability Relative Value For Wild-type | Note |
|---|---|---|---|---|---|
| (21) | α36 | Thr | Trp | 1.36 | Example 19 |
|  | α43 | Ala | Val |  |  |
|  | β205 | Gly | Val |  |  |
| (22) | α40 | Thr | Trp | 1.38 | Example 20 |
|  | α43 | Ala | Val |  |  |
|  | β205 | Gly | Val |  |  |
| (23) | α36 | Thr | Trp | 1.34 | Example 21 |
|  | α43 | Ala | Val |  |  |
|  | β215 | Tyr | Asn |  |  |

From the results shown in Table 16, it could be appreciated that each amino acid residue substitution belonging to the amino acid residue substitution group A resulted in an improvement in the pH stability of the nitrile hydratase in a case in which two or more amino acid residue substitutions were combined with each other and even in a case in which the amino acid residue substitution (f) was further combined. Further, it could be appreciated that the degree of stabilization tended to be improved depending on the combinations.

[Example 22] Obtainment of Mutant Nitrile Hydratase (24)

In order to obtain a transformant (24) expressing a mutant nitrile hydratase having an amino acid residue substitution as shown in Table 17, the transformant (24) was obtained in the same manner as in Comparative Example 2 above except that the plasmid of Example 7 was used as a template and a primer of SEQ ID NO: 15 was used in place of the primer of SEQ ID NO: 5. The transformant (24) produces a nitrile hydratase (24) having the mutation described in Table 17.

The pH stability of the nitrile hydratase (24) was evaluated by the method described in "Comparison of pH Stability" described above. The obtained results are shown in Table 17 below.

TABLE 17

| Nitrile Hydratase No. | Mutation Site | Before Mutation | After Mutation | pH Stability Relative Value For Wild-type | Note |
|---|---|---|---|---|---|
| (24) | α36 | Thr | Trp | 1.41 | Example 22 |
|  | α43 | Ala | Val |  |  |
|  | β205 | Gly | Val |  |  |
|  | β206 | Pro | Gln |  |  |

From the results shown in Table 17, it could be appreciated that each amino acid residue substitution belonging to the amino acid residue substitution group A resulted in an improvement in the pH stability of the nitrile hydratase even in a case in which three or more amino acid residue substitutions were combined with each other. In addition, the degree of improvement tends to be much higher.

[Example 23] Initial Reaction Rate of Mutant Nitrile Hydratase

Initial reaction rates of the wild-type *Pseudonocardia thermophila*-derived nitrile hydratase and nitrile hydratases having the amino acid residue substitutions shown in Table 18 are shown in Table 18 as examination results obtained by measuring initial reaction rates in measurement of amide compound production before the acid treatment described in "Comparison of pH Stability". The value of the initial reaction rate is shown as a relative value with respect to the initial reaction rate value in the wild-type *Pseudonocardia thermophila*-derived nitrile hydratase.

TABLE 18

| Nitrile Hydratase No. | Mutation Site | Before Mutation | After Mutation | Initial Reaction Rate Relative Value For Wild-type | Note |
|---|---|---|---|---|---|
| (1) | Wild-type | None | None | 1.00 | Comparative Example 1 |
| (2) | α92 | Asp | Glu | 1.22 | Comparative Example 2 |
| (5) | β205 | Gly | Val | 1.15 | Example 3 |

TABLE 18-continued

| Nitrile Hydratase No. | Mutation Site | Before Mutation | After Mutation | Initial Reaction Rate Relative Value For Wild-type | Note |
|---|---|---|---|---|---|
| (8) | α36 | Thr | Trp | 1.24 | Example 6 |
|  | α40 | Asp | Asn |  |  |
| (21) | α36 | Thr | Trp | 1.27 | Example 19 |
|  | α43 | Ala | Val |  |  |
|  | β205 | Gly | Val |  |  |
| (24) | α36 | Thr | Trp | 1.36 | Example 22 |
|  | α43 | Ala | Val |  |  |
|  | β205 | Gly | Val |  |  |
|  | β206 | Pro | Gln |  |  |

From the results shown in Table 18, it could be appreciated that each amino acid residue substitution belonging to the amino acid residue substitution group A also resulted in an improvement in the initial reaction rate of nitrile hydratase.

[Comparative Example 3] Obtainment of Nitrile Hydratase Mutant (25)

A transformant (25) was obtained in the same manner as in the transformation described in Comparative Example 2 using a plasmid including the nitrile hydratase mutant which was mutated at the amino acid substitution position as shown in Table 19 (see Japanese Patent No. 5551081, Transformant No. 92). The transformant (25) produces a nitrile hydratase (25) having the mutation described in Table 19.

The pH stability of the nitrile hydratase (25) was evaluated by the method described in "Comparison of pH Stability" described above. The obtained results are shown in Table 19 below.

[Example 24] Obtainment of Nitrile Hydratase Mutant (26)

In order to obtain a transformant (26) expressing a mutant nitrile hydratase having an amino acid residue substitution as shown in Table 19, a plasmid was obtained and the transformant (26) was obtained in the same manner as in Comparative Example 2 above except that the plasmid of Comparative Example 3 was used as a template and a primer of SEQ ID NO: 8 was used in place of the primer of SEQ ID NO: 5. The transformant (26) produces a nitrile hydratase (26) having the mutation described in Table 19.

The pH stability of the nitrile hydratase (26) was evaluated by the method described in "Comparison of pH Stability" described above. The obtained results are shown in Table 19 below.

TABLE 19

| Nitrile Hydratase No. | Mutation Site | Before Mutation | After Mutation | pH Stability Relative Value for Nitrile Hydratase (25) | Note |
|---|---|---|---|---|---|
| (25) | α6 | Leu | Thr | 1.00 | Comparative Example 3 |
|  | α36 | Thr | Met |  |  |
|  | α126 | Phe | Tyr |  |  |
|  | β10 | Thr | Asp |  |  |
|  | β118 | Phe | Val |  |  |
|  | β200 | Ala | Glu |  |  |
|  | β206 | Pro | Leu |  |  |
|  | β230 | Ala | Glu |  |  |
| (26) | α6 | Leu | Thr | 1.15 | Example 24 |
|  | α36 | Thr | Met |  |  |
|  | α43 | Ala | Val |  |  |
|  | α126 | Phe | Tyr |  |  |
|  | β10 | Thr | Asp |  |  |
|  | β118 | Phe | Val |  |  |
|  | β200 | Ala | Glu |  |  |
|  | β206 | Pro | Leu |  |  |
|  | β230 | Ala | Glu |  |  |

From the results shown in Table 19, it could be appreciated that the amino acid residue substitution belonging to the amino acid residue substitution group A resulted in not only an improvement of pH stability of the wild-type *Pseudonocardia thermophila*-derived nitrile hydratase but also an improvement of pH stability of the nitrile hydratase having the modified amino acid sequence from the wild-type *Pseudonocardia thermophila*-derived nitrile hydratase.

[Example 25] Initial Reaction Rate of Nitrile Hydratase Mutant

Initial reaction rates of the nitrile hydratase mutants which were mutated at the amino acid substitution positions shown in Table 20 are shown in Table 20 as examination results obtained by measuring initial reaction rates in measurement of amide compound production before the acid treatment described in "Comparison of pH Stability". The value of the initial reaction rate is shown as a relative value with respect to the initial reaction rate value in the nitrile hydratase (25).

TABLE 20

| Nitrile Hydratase No. | Mutation Site | Before Mutation | After Mutation | Initial Reaction Rate Relative Value for Nitrile Hydratase (25) | Note |
|---|---|---|---|---|---|
| (25) | α6 | Leu | Thr | 1.00 | Comparative Example 3 |
|  | α36 | Thr | Met |  |  |
|  | α126 | Phe | Tyr |  |  |
|  | β10 | Thr | Asp |  |  |
|  | β118 | Phe | Val |  |  |
|  | β200 | Ala | Glu |  |  |
|  | β206 | Pro | Leu |  |  |
|  | β230 | Ala | Glu |  |  |
| (26) | α6 | Leu | Thr | 1.11 | Example 24 |
|  | α36 | Thr | Met |  |  |
|  | α43 | Ala | Val |  |  |
|  | α126 | Phe | Tyr |  |  |
|  | β10 | Thr | Asp |  |  |
|  | β118 | Phe | Val |  |  |
|  | β200 | Ala | Glu |  |  |
|  | β206 | Pro | Leu |  |  |
|  | β230 | Ala | Glu |  |  |

From the results shown in Table 20, it could be appreciated that the amino acid residue substitution belonging to the amino acid residue substitution group A resulted in not only an improvement of initial reaction rate of the wild-type *Pseudonocardia thermophila*-derived nitrile hydratase but also an improvement of initial reaction rate of the nitrile hydratase having the modified amino acid sequence from the wild-type *Pseudonocardia thermophila*-derived nitrile hydratase.

[Comparative Example 4] Obtainment of Nitrile Hydratase Mutant (27)

A transformant (27) was obtained in the same manner as in the transformation described in Comparative Example 2 using a plasmid including the nitrile hydratase mutant which was mutated at the amino acid substitution position as shown in Table 21 (see Japanese Patent No. 5551081, Transformant No. 114). The transformant (27) produces a nitrile hydratase (27) having the mutation described in Table 21.

The pH stability of the nitrile hydratase (27) was evaluated by the method described in "Comparison of pH Stability" described above. The obtained results are shown in Table 21 below.

[Comparative Example 26] Obtainment of Nitrile Hydratase Mutant (28)

In order to obtain a transformant (28) expressing a mutant nitrile hydratase having an amino acid residue substitution as shown in Table 21, a plasmid was obtained and a transformant (28) was obtained in the same manner as in Comparative Example 2 above except that the plasmid of Example 4 was used as a template and a primer of SEQ ID NO: 8 was used in place of the primer of SEQ ID NO: 5. The transformant (28) produces a nitrile hydratase (28) having the mutation described in Table 21.

The pH stability of the nitrile hydratase (28) was evaluated by the method described in "Comparison of pH Stability" described above. The obtained results are shown in Table 21 below.

TABLE 21

| Nitrile Hydratase No. | Mutation Site | Before Mutation | After Mutation | pH Stability Relative Value for Nitrile Hydratase (27) | Note |
|---|---|---|---|---|---|
| (27) | α92 | Asp | Glu | 1.00 | Comparative Example 4 |
|  | β24 | Val | Ile |  |  |
|  | β41 | Phe | Ile |  |  |
|  | β51 | Phe | Val |  |  |
|  | β108 | Glu | Asp |  |  |
|  | β223 | Val | Ile |  |  |
| (28) | α43 | Ala | Val | 1.19 | Example 26 |
|  | α92 | Asp | Glu |  |  |
|  | β24 | Val | Ile |  |  |
|  | β41 | Phe | Ile |  |  |
|  | β51 | Phe | Val |  |  |
|  | β108 | Glu | Asp |  |  |
|  | β223 | Val | Ile |  |  |

From the results shown in Table 21, it could be appreciated that the amino acid residue substitution belonging to the amino acid residue substitution group A resulted in not only an improvement of pH stability of the wild-type *Pseudonocardia thermophila*-derived nitrile hydratase but also an improvement of pH stability of the nitrile hydratase having the modified amino acid sequence from the wild-type *Pseudonocardia thermophila*-derived nitrile hydratase.

[Example 27] Initial Reaction Rate of Nitrile Hydratase Mutant

Initial reaction rates of the nitrile hydratase mutants which were mutated at the amino acid substitution positions shown in Table 21 are shown in Table 22 as examination results obtained by measuring initial reaction rates in measurement of amide compound production before the acid treatment described in "Comparison of pH Stability". The value of the initial reaction rate is shown as a relative value with respect to the initial reaction rate value in the nitrile hydratase (27).

TABLE 22

| Nitrile Hydratase No. | Mutation Site | Before Mutation | After Mutation | pH Initial Reaction Rate Relative Value for Nitrile Hydratase (27) | Note |
|---|---|---|---|---|---|
| (27) | α92 | Asp | Glu | 1.00 | Comparative Example 4 |
|  | β24 | Val | Ile |  |  |
|  | β41 | Phe | Ile |  |  |
|  | β51 | Phe | Val |  |  |
|  | β108 | Glu | Asp |  |  |
|  | β223 | Val | Ile |  |  |
| (28) | α43 | Ala | Val | 1.05 | Example 26 |
|  | α92 | Asp | Glu |  |  |
|  | β24 | Val | Ile |  |  |
|  | β41 | Phe | Ile |  |  |
|  | β51 | Phe | Val |  |  |
|  | β108 | Glu | Asp |  |  |
|  | β223 | Val | Ile |  |  |

From the results shown in Table 22, it could be appreciated that the amino acid residue substitution belonging to the amino acid residue substitution group A resulted in not only an improvement of initial reaction rate of the wild-type *Pseudonocardia thermophila*-derived nitrile hydratase but also an improvement of initial reaction rate of the nitrile hydratase having the modified amino acid sequence from the wild-type *Pseudonocardia thermophila*-derived nitrile hydratase.

[Comparative Example 5] Obtainment of Nitrile Hydratase Mutant (29)

A transformant (29) was obtained in the same manner as in the transformation described in Comparative Example 2 using a plasmid including the nitrile hydratase mutant which was mutated at the amino acid substitution position as shown in Table 23 (see Japanese Patent No. 5551081, Transformant No. 33). The transformant (29) produces a nitrile hydratase (29) having the mutation described in Table 23.

The pH stability of the nitrile hydratase (29) was evaluated by the method described in "Comparison of pH Stability" described above. The obtained results are shown in Table 23 below.

[Example 28] Obtainment of Nitrile Hydratase Mutant (30)

In order to obtain a transformant (30) expressing a mutant nitrile hydratase having an amino acid residue substitution as shown in Table 23, a plasmid was obtained and the transformant (30) was obtained in the same manner as in Comparative Example 2 above except that the plasmid of Comparative Example 5 was used as a template and a primer of SEQ ID NO: 8 was used in place of the primer of SEQ ID NO: 5. The transformant (30) produces a nitrile hydratase (30) having the mutation described in Table 23.

The pH stability of the nitrile hydratase (30) was evaluated by the method described in "Comparison of pH Stability" described above. The obtained results are shown in Table 23 below.

TABLE 23

| Nitrile Hydratase No. | Mutation Site | Before Mutation | After Mutation | pH Stability Relative Value for Nitrile Hydratase (29) | Note |
|---|---|---|---|---|---|
| (29) | α19 | Ala | Val | 1.00 | Comparative Example 5 |
| | α71 | Arg | His | | |
| | α126 | Phe | Try | | |
| | β37 | Phe | Val | | |
| | β79 | His | Asn | | |
| | β108 | Glu | Asp | | |
| | β200 | Ala | Glu | | |
| (30) | α19 | Ala | Val | 1.16 | Example 28 |
| | α43 | Ala | Val | | |
| | α71 | Arg | His | | |
| | α126 | Phe | Try | | |
| | β37 | Phe | Val | | |
| | β79 | His | Asn | | |
| | β108 | Glu | Asp | | |
| | β200 | Ala | Glu | | |

From the results shown in Table 23, it could be appreciated that the amino acid residue substitution belonging to the amino acid residue substitution group A resulted in not only an improvement of pH stability of the wild-type *Pseudonocardia thermophila*-derived nitrile hydratase but also an improvement of pH stability of the nitrile hydratase having the modified amino acid sequence from the wild-type *Pseudonocardia thermophila*-derived nitrile hydratase.

[Example 29] Initial Reaction Rate of Nitrile Hydratase Mutant

Reaction initial rates of the nitrile hydratase mutants which were mutated at the amino acid substitution positions shown in Table 23 are shown in Table 24 as examination results obtained by measuring initial reaction rates in measurement of amide compound production before the acid treatment described in "Comparison of pH Stability". The value of the initial reaction rate is shown as a relative value with respect to the initial reaction rate value in the nitrile hydratase (29).

TABLE 24

| Nitrile Hydratase No. | Mutation Site | Before Mutation | After Mutation | Initial Reaction Rate Relative Value for Nitrile Hydratase (29) | Note |
|---|---|---|---|---|---|
| (29) | α19 | Ala | Val | 1.00 | Comparative Example 5 |
| | α71 | Arg | His | | |
| | α126 | Phe | Try | | |
| | β37 | Phe | Val | | |
| | β79 | His | Asn | | |
| | β108 | Glu | Asp | | |
| | β200 | Ala | Glu | | |
| (30) | α19 | Ala | Val | 1.10 | Example 28 |
| | α43 | Ala | Val | | |
| | α71 | Arg | His | | |
| | α126 | Phe | Try | | |
| | β37 | Phe | Val | | |
| | β79 | His | Asn | | |
| | β108 | Glu | Asp | | |
| | β200 | Ala | Glu | | |

From the results shown in Table 24, it could be appreciated that the amino acid residue substitution belonging to the amino acid residue substitution group A resulted in not only an improvement of initial reaction rate of the wild-type *Pseudonocardia thermophila*-derived nitrile hydratase but also an improvement of initial reaction rate of the nitrile hydratase having the modified amino acid sequence from the wild-type *Pseudonocardia thermophila*-derived nitrile hydratase.

The disclosure of Japanese Patent Application No. 2016-256050 filed on Dec. 28, 2016 is hereby incorporated by reference in its entirety.

All documents, patent applications, and technical standards described in this specification are hereby incorporated by reference in their entirety to the same extent as a case in which each document, patent application, and technical specification are specifically and individually described to be incorporated by reference.

SEQUENCE LIST

International application under the International Patent Cooperation Treaty MT-F03210-JP 17047127_24.app

The invention claimed is:

1. A mutant nitrile hydratase that is derived from *Pseudonocardia thermophila* and has an α subunit and a β subunit, the mutant nitrile hydratase comprising at least one amino acid residue substitution selected from the group consisting of the following amino acid residue substitutions (a) to (d), wherein the α subunit has at least 90% amino acid sequence identity to the amino acid sequence represented by SEQ ID NO: 1, and the β subunit has at least 90% amino acid sequence identity to the amino acid sequence represented by SEQ ID NO: 2:
   (a) a substitution of an amino acid corresponding to the 40th amino acid residue from an N terminal of SEQ ID NO: 1 with Asn, in the α subunit,
   (b) a substitution of an amino acid corresponding to the 43rd amino acid residue from the N terminal of SEQ ID NO: 1 with Val, in the α subunit,
   (c) a substitution of an amino acid corresponding to the 205th amino acid residue from an N terminal of SEQ ID NO: 2 with Val, in the β subunit, and
   (d) a substitution of an amino acid corresponding to the 215th amino acid residue from the N terminal of SEQ ID NO: 2 with Asn, in the β subunit.

2. The mutant nitrile hydratase according to claim 1, comprising two or more amino acid residue substitutions selected from the group consisting of the amino acid residue substitutions (a) to (d).

3. The mutant nitrile hydratase according to claim 1, comprising the amino acid residue substitution (b), and at least one selected from the group consisting of the amino acid residue substitutions (a), (c), and (d).

4. The mutant nitrile hydratase according to claim 1, wherein an amino acid corresponding to the 36th amino acid from the N terminal of SEQ ID NO: 1 is Trp in the amino acid sequence of the α subunit.

5. The mutant nitrile hydratase according to claim 1, wherein an amino acid corresponding to the 36th amino acid from the N terminal of SEQ ID NO: 1 is Met, Ser, Gly, or Ala, in the amino acid sequence of the α subunit.

6. The mutant nitrile hydratase according to claim 1, wherein the amino acid sequence of the α subunit further satisfies one or more of the following conditions (1) to (13):
   (1) an amino acid corresponding to the 6th amino acid residue from the N terminal of SEQ ID NO: 1 is Thr or Ala,
   (2) an amino acid corresponding to the 13th amino acid residue from the N terminal of SEQ ID NO: 1 is Leu,
   (3) an amino acid corresponding to the 19th amino acid residue from the N terminal of SEQ ID NO: 1 is Val,
   (4) an amino acid corresponding to the 27th amino acid residue from the N terminal of SEQ ID NO: 1 is Ile,
   (5) an amino acid corresponding to the 48th amino acid residue from the N terminal of SEQ ID NO: 1 is Gln,
   (6) an amino acid corresponding to the 71st amino acid residue from the N terminal of SEQ ID NO: 1 is His,
   (7) an amino acid corresponding to the 92nd amino acid residue from the N terminal of SEQ ID NO: 1 is Glu,
   (8) an amino acid corresponding to the 94th amino acid residue from the N terminal of SEQ ID NO: 1 is Ile,
   (9) an amino acid corresponding to the 126th amino acid residue from the N terminal of SEQ ID NO: 1 is Tyr,
   (10) an amino acid corresponding to the 148th amino acid residue from the N terminal of SEQ ID NO: 1 is Asp,
   (11) an amino acid corresponding to the 188th amino acid residue from the N terminal of SEQ ID NO: 1 is Gly,
   (12) an amino acid corresponding to the 197th amino acid residue from the N terminal of SEQ ID NO: 1 is Cys, and
   (13) an amino acid corresponding to the 204th amino acid residue from the N terminal of SEQ ID NO: 1 is Arg.

7. The mutant nitrile hydratase according to claim 1, wherein the amino acid sequence of the β subunit further satisfies at least one of the following conditions (15) to (47):
   (15) an amino acid corresponding to the 4th amino acid residue from the N terminal of SEQ ID NO: 2 is Met,
   (16) an amino acid corresponding to the 8th amino acid residue from the N terminal of SEQ ID NO: 2 is Ala,
   (17) an amino acid corresponding to the 10th amino acid residue from the N terminal of SEQ ID NO: 2 is Asp,
   (18) an amino acid corresponding to the 24th amino acid residue from the N terminal of SEQ ID NO: 2 is Ile,
   (19) an amino acid corresponding to the 33rd amino acid residue from the N terminal of SEQ ID NO: 2 is Val, or Met,
   (20) an amino acid corresponding to the 37th amino acid residue from the N terminal of SEQ ID NO: 2 is Val, or Leu,
   (21) an amino acid corresponding to the 40th amino acid residue from the N terminal of SEQ ID NO: 2 is Ile, Val, or Leu,
   (22) an amino acid corresponding to the 41st amino acid residue from the N terminal of SEQ ID NO: 2 is Ile,
   (23) an amino acid corresponding to the 46th amino acid residue from the N terminal of SEQ ID NO: 2 is Lys,
   (24) an amino acid corresponding to the 48th amino acid residue from the N terminal of SEQ ID NO: 2 is Val,
   (25) an amino acid corresponding to the 51st amino acid residue from the N terminal of SEQ ID NO: 2 is Val,
   (26) an amino acid corresponding to the 61st amino acid residue from the N terminal of SEQ ID NO: 2 is Val, Gly, Trp, Ser, Leu, or Thr,
   (27) an amino acid corresponding to the 79th amino acid residue from the N terminal of SEQ ID NO: 2 is Asn,
   (28) an amino acid corresponding to the 96th amino acid residue from the N terminal of SEQ ID NO: 2 is Arg,
   (29) an amino acid corresponding to the 107th amino acid residue from the N terminal of SEQ ID NO: 2 is Met,
   (30) an amino acid corresponding to the 108th amino acid residue from the N terminal of SEQ ID NO: 2 is Asp or Arg,
   (31) an amino acid corresponding to the 110th amino acid residue from the N terminal of SEQ ID NO: 2 is Asn,

(32) an amino acid corresponding to the 112th amino acid residue from the N terminal of SEQ ID NO: 2 is Val, or Ile,
(33) an amino acid corresponding to the 118th amino acid residue from the N terminal of SEQ ID NO: 2 is Val,
(34) an amino acid corresponding to the 127th amino acid residue from the N terminal of SEQ ID NO: 2 is Ser,
(35) an amino acid corresponding to the 146th amino acid residue from the N terminal of SEQ ID NO: 2 is Gly,
(36) an amino acid corresponding to the 150th amino acid residue from the N terminal of SEQ ID NO: 2 is Asn or Ser,
(37) an amino acid corresponding to the 160th amino acid residue from the N terminal of SEQ ID NO: 2 is Cys, Trp, or Met,
(38) an amino acid corresponding to the 168th amino acid residue from the N terminal of SEQ ID NO: 2 is Glu,
(39) an amino acid corresponding to the 176th amino acid residue from the N terminal of SEQ ID NO: 2 is Ala, Thr, Met, or Cys,
(40) an amino acid corresponding to the 186th amino acid residue from the N terminal of SEQ ID NO: 2 is Arg,
(41) an amino acid corresponding to the 200th amino acid residue from the N terminal of SEQ ID NO: 2 is Glu,
(42) an amino acid corresponding to the 212th amino acid residue from the N terminal of SEQ ID NO: 2 is Tyr,
(43) an amino acid corresponding to the 217th amino acid residue from the N terminal of SEQ ID NO: 2 is Val, His, Met, Gly, Ser, Leu, or Cys,
(44) an amino acid corresponding to the 218th amino acid residue from the N terminal of SEQ ID NO: 2 is Met, or Ser,
(45) an amino acid corresponding to the 226th amino acid residue from the N terminal of SEQ ID NO: 2 is Ile,
(46) an amino acid corresponding to the 230th amino acid residue from the N terminal of SEQ ID NO: 2 is Glu, and
(47) an amino acid corresponding to the 231st amino acid residue from the N terminal of SEQ ID NO: 2 is Val.

8. The mutant nitrile hydratase according to claim 1, comprising at least one amino acid residue substitution selected from the group consisting of the amino acid residue substitutions (a) to (d) in any one of the following *Pseudonocardia thermophila*-derived nitrile hydratases [1] to [48]:

[1] a nitrile hydratase that has an α-subunit having the amino acid sequence of SEQ ID NO: 1 and a β-subunit having the amino acid sequence of SEQ ID NO: 2,
[2] a nitrile hydratase that has an α-subunit having the amino acid sequence of SEQ ID NO: 16 and a β-subunit having the amino acid sequence of SEQ ID NO: 33,
[3] a nitrile hydratase that has an α-subunit having the amino acid sequence of SEQ ID NO: 17 and a β-subunit having the amino acid sequence of SEQ ID NO: 33,
[4] a nitrile hydratase that has the α-subunit having an amino acid sequence of SEQ ID NO: 18 and a β-subunit having the amino acid sequence of SEQ ID NO: 34,
[5] a nitrile hydratase that has an α-subunit having the amino acid sequence of SEQ ID NO: 19 and a β-subunit having the amino acid sequence of SEQ ID NO: 34,
[6] a nitrile hydratase that has an α-subunit having the amino acid sequence of SEQ ID NO: 20 and a β-subunit having the amino acid sequence of SEQ ID NO: 35,
[7] a nitrile hydratase that has an α-subunit having the amino acid sequence of SEQ ID NO: 20 and a β-subunit having the amino acid sequence of SEQ ID NO: 36,
[8] a nitrile hydratase that has an α-subunit having the amino acid sequence of SEQ ID NO: 21 and a β-subunit having the amino acid sequence of SEQ ID NO: 37,
[9] a nitrile hydratase that has an α-subunit having the amino acid sequence of SEQ ID NO: 21 and a β-subunit having the amino acid sequence of SEQ ID NO: 38,
[10] a nitrile hydratase that has an α-subunit having the amino acid sequence of SEQ ID NO: 21 and a β-subunit having the amino acid sequence of SEQ ID NO: 39,
[11] a nitrile hydratase that has an α-subunit having the amino acid sequence of SEQ ID NO: 21 and a β-subunit having the amino acid sequence of SEQ ID NO: 40,
[12] a nitrile hydratase that has an α-subunit having the amino acid sequence of SEQ ID NO: 18 and a β-subunit having the amino acid sequence of SEQ ID NO: 41,
[13] a nitrile hydratase that has an α-subunit having the amino acid sequence of SEQ ID NO: 18 and a β-subunit having the amino acid sequence of SEQ ID NO: 42,
[14] a nitrile hydratase that has an α-subunit having the amino acid sequence of SEQ ID NO: 21 and a β-subunit having the amino acid sequence of SEQ ID NO: 43,
[15] a nitrile hydratase that has an α-subunit having the amino acid sequence of SEQ ID NO: 22 and a β-subunit having the amino acid sequence of SEQ ID NO: 44,
[16] a nitrile hydratase that has an α-subunit having the amino acid sequence of SEQ ID NO: 23 and a β-subunit having the amino acid sequence of SEQ ID NO: 45,
[17] a nitrile hydratase that has an α-subunit having the amino acid sequence of SEQ ID NO: 24 and a β-subunit having the amino acid sequence of SEQ ID NO: 46,
[18] a nitrile hydratase that has an α-subunit having the amino acid sequence of SEQ ID NO: 25 and a β-subunit having the amino acid sequence of SEQ ID NO: 47,
[19] a nitrile hydratase that has an α-subunit having the amino acid sequence of SEQ ID NO: 18 and a β-subunit having the amino acid sequence of SEQ ID NO: 48,
[20] a nitrile hydratase that has an α-subunit having the amino acid sequence of SEQ ID NO: 23 and a β-subunit having the amino acid sequence of SEQ ID NO: 49,
[21] a nitrile hydratase that has an α-subunit having the amino acid sequence of SEQ ID NO: 16 and a β-subunit having the amino acid sequence of SEQ ID NO: 50,
[22] a nitrile hydratase that has an α-subunit having the amino acid sequence of SEQ ID NO: 26 and a β-subunit having the amino acid sequence of SEQ ID NO: 51,

[23] a nitrile hydratase that has an α-subunit having the amino acid sequence of SEQ ID NO: 27 and a β-subunit having the amino acid sequence of SEQ ID NO: 52,

[24] a nitrile hydratase that has an α-subunit having the amino acid sequence of SEQ ID NO: 28 and a β-subunit having the amino acid sequence of SEQ ID NO: 53,

[25] a nitrile hydratase that has an α-subunit having the amino acid sequence of SEQ ID NO: 17 and a β-subunit having the amino acid sequence of SEQ ID NO: 54,

[26] a nitrile hydratase that has an α-subunit having the amino acid sequence of SEQ ID NO: 29 and a β-subunit having the amino acid sequence of SEQ ID NO: 55,

[27] a nitrile hydratase that has an α-subunit having the amino acid sequence of SEQ ID NO: 18 and a β-subunit having the amino acid sequence of SEQ ID NO: 56,

[28] a nitrile hydratase that has an α-subunit having the amino acid sequence of SEQ ID NO: 18 and a β-subunit having the amino acid sequence of SEQ ID NO: 57,

[29] a nitrile hydratase that has an α-subunit having the amino acid sequence of SEQ ID NO: 30 and a β-subunit having the amino acid sequence of SEQ ID NO: 58,

[30] a nitrile hydratase that has an α-subunit having the amino acid sequence of SEQ ID NO: 29 and a β-subunit having the amino acid sequence of SEQ ID NO: 59,

[31] a nitrile hydratase that has an α-subunit having the amino acid sequence of SEQ ID NO: 31 and a β-subunit having the amino acid sequence of SEQ ID NO: 60,

[32] a nitrile hydratase that has an α-subunit having the amino acid sequence of SEQ ID NO: 18 and a β-subunit having the amino acid sequence of SEQ ID NO: 61,

[33] a nitrile hydratase that has an α-subunit having the amino acid sequence of SEQ ID NO: 32 and a β-subunit having the amino acid sequence of SEQ ID NO: 62,

[34] a nitrile hydratase that has an α-subunit having the amino acid sequence of SEQ ID NO: 30 and a β-subunit having the amino acid sequence of SEQ ID NO: 63,

[35] a nitrile hydratase that has an α-subunit having the amino acid sequence of SEQ ID NO: 30 and a β-subunit having the amino acid sequence of SEQ ID NO: 64,

[36] a nitrile hydratase that has an α-subunit having the amino acid sequence of SEQ ID NO: 30 and a β-subunit having the amino acid sequence of SEQ ID NO: 65,

[37] a nitrile hydratase that has an α-subunit having the amino acid sequence of SEQ ID NO: 25 and a β-subunit having the amino acid sequence of SEQ ID NO: 54,

[38] a nitrile hydratase that has an α-subunit having the amino acid sequence of SEQ ID NO: 30 and a β-subunit having the amino acid sequence of SEQ ID NO: 66,

[39] a nitrile hydratase that has an α-subunit having the amino acid sequence of SEQ ID NO: 1 and a β-subunit having the amino acid sequence of SEQ ID NO: 67,

[40] a nitrile hydratase that has an α-subunit having the amino acid sequence of SEQ ID NO: 1 and a β-subunit having the amino acid sequence of SEQ ID NO: 68,

[41] a nitrile hydratase that has an α-subunit having the amino acid sequence of SEQ ID NO: 1 and a β-subunit having the amino acid sequence of SEQ ID NO: 69,

[42] a nitrile hydratase that has an α-subunit having the amino acid sequence of SEQ ID NO: 1 and a β-subunit having the amino acid sequence of SEQ ID NO: 70,

[43] a nitrile hydratase that has an α-subunit having the amino acid sequence of SEQ ID NO: 1 and a β-subunit having the amino acid sequence of SEQ ID NO: 71,

[44] a nitrile hydratase that has an α-subunit having the amino acid sequence of SEQ ID NO: 21 and a β-subunit having the amino acid sequence of SEQ ID NO: 72,

[45] a nitrile hydratase that has an α-subunit having the amino acid sequence of SEQ ID NO: 1 and a β-subunit having the amino acid sequence of SEQ ID NO: 73,

[46] a nitrile hydratase in which the 36th amino acid residue from the N terminal of the α-subunit in any one of the nitrile hydratases [1] to [45] is a Trp residue,

[47] a nitrile hydratase that has the α-subunit of a nitrile hydratase (A) of any one of [1] to [46] or an α-subunit variant consisting of an amino acid sequence having 90% or more sequence identity with the α-subunit; and a β-subunit of the nitrile hydratase (A) or a β-subunit variant consisting of an amino acid sequence having 90% or more sequence identity with the β-subunit, wherein at least one of the α-subunit or the β-subunit is the α-subunit variant or the β-subunit variant, and

[48] a nitrile hydratase in which the total number of amino acid residues added, substituted, deleted, inserted, or any combination thereof, is from 1 to 10 (excluding the amino acid residues to be substituted in (a) and (b)) in the α-subunit of a nitrile hydratase (B) of any one of [1] to [46], and the total number of amino acid residues added, substituted, deleted, inserted, or any combination thereof, is from 1 to 10 (excluding the amino acid residues to be substituted in (c) to (d)) in the β-subunit of the nitrile hydratase (B).

9. A nucleic acid encoding the mutant nitrile hydratase according to claim 1.

10. A vector comprising the nucleic acid according to claim 9.

11. The vector according to claim 10, being an expression vector.

12. A transformant comprising the expression vector according to claim 11.

13. A method of producing a mutant nitrile hydratase, the method comprising:
culturing the transformant according to claim 12 in a medium; and
recovering the mutant nitrile hydratase from at least one of the cultured transformant or the medium.

14. A mutant nitrile hydratase obtained by the method according to claim 13.

15. A method of producing an amide compound, the method comprising bringing the mutant nitrile hydratase according to claim 1 into contact with a nitrile compound.

16. The method of producing an amide compound according to claim 15, further comprising removing impurities from a solution containing an amide compound at from pH 3.5 to pH 6.5.

17. The method of producing an amide compound according to claim 15, further comprising purifying the amide compound with activated carbon.

* * * * *